US012728186B2

(12) United States Patent
Cahyadi et al.

(10) Patent No.: US 12,728,186 B2
(45) Date of Patent: Sep. 8, 2026

(54) METHODS AND KITS FOR PREPARING PATHOGEN-INACTIVATED WHOLE BLOOD

(71) Applicant: Cerus Corporation, Concord, CA (US)

(72) Inventors: Harry Cahyadi, Concord, CA (US); Anne North, Concord, CA (US); Melissa Von Goetz, Concord, CA (US); Anna Erickson, Concord, CA (US)

(73) Assignee: Cerus Corporation, Concord, CA (US)

( * ) Notice: Subject to any disclaimer, the term of this patent is extended or adjusted under 35 U.S.C. 154(b) by 1059 days.

(21) Appl. No.: 17/277,680

(22) PCT Filed: Sep. 20, 2019

(86) PCT No.: PCT/US2019/052286
§ 371 (c)(1),
(2) Date: Mar. 18, 2021

(87) PCT Pub. No.: WO2020/061537
PCT Pub. Date: Mar. 26, 2020

(65) Prior Publication Data

US 2022/0031917 A1 Feb. 3, 2022

Related U.S. Application Data

(60) Provisional application No. 62/734,117, filed on Sep. 20, 2018.

(51) Int. Cl.
*A61M 1/02* (2006.01)
*A61K 31/435* (2006.01)
(Continued)

(52) U.S. Cl.
CPC ......... *A61M 1/0281* (2013.01); *A61K 31/435* (2013.01); *A61K 35/16* (2013.01);
(Continued)

(58) Field of Classification Search
CPC . A61M 1/0209; A61M 1/0281; A61K 31/435; A61K 35/16; A61K 38/06; A61L 2/0088; A61L 2202/22
See application file for complete search history.

(56) References Cited

U.S. PATENT DOCUMENTS 5,288,605 A 2/1994 Lin et al.
5,399,719 A 3/1995 Wollowitz et al.
(Continued)

FOREIGN PATENT DOCUMENTS

CA 2380832 A1 12/2001
EP 1045704 B1 9/2004
(Continued)

OTHER PUBLICATIONS

Henschler, R. et al. (Jan. 1, 2011). "Development of the S-303 Pathogen Inactivation Technology for Red Blood Cell Concentrates," Transfusion Medicine And Hemotherapy 38(1):33-42.
(Continued)

*Primary Examiner* — Rebecca E Eisenberg
*Assistant Examiner* — Timothy L Flynn
(74) *Attorney, Agent, or Firm* — MORRISON & FOERSTER LLP

(57) ABSTRACT

Provided are methods for preparing pathogen-inactivated whole blood and other pathogen-inactivated blood product compositions, as well as kits and compositions related thereto.

43 Claims, 24 Drawing Sheets

(51) Int. Cl.

| | |
|---|---|
| ***A61K 35/16*** | (2015.01) |
| ***A61K 38/06*** | (2006.01) |
| ***A61L 2/18*** | (2026.01) |
| ***A61L 103/05*** | (2026.01) |
| ***A61L 103/09*** | (2026.01) |

(52) U.S. Cl.

CPC ................ *A61K 38/06* (2013.01); *A61L 2/18* (2013.01); *A61M 1/0209* (2013.01); *A61L 2103/05* (2026.01); *A61L 2103/09* (2026.01)

(56) References Cited

U.S. PATENT DOCUMENTS

| | | | |
|---|---|---|---|
| 5,459,030 | A | 10/1995 | Lin et al. |
| 5,482,828 | A | 1/1996 | Lin et al. |
| 5,556,993 | A | 9/1996 | Wollowitz |
| 5,559,250 | A | 9/1996 | Cook |
| 5,564,443 | A | 10/1996 | Cardenas |
| 5,578,736 | A | 11/1996 | Wollowitz |
| 5,585,503 | A | 12/1996 | Wollowitz |
| 5,593,823 | A | 1/1997 | Wollowitz et al. |
| 5,618,662 | A | 4/1997 | Lin et al. |
| 5,625,079 | A | 4/1997 | Wollowitz |
| 5,691,132 | A | 11/1997 | Wollowitz et al. |
| 5,709,991 | A | 1/1998 | Lin et al. |
| 5,712,085 | A | 1/1998 | Wollowitz |
| 5,871,900 | A | 2/1999 | Wollowitz |
| 5,908,742 | A | 6/1999 | Lin et al. |
| 5,965,349 | A | 10/1999 | Lin |
| 5,972,593 | A | 10/1999 | Wollowitz |
| 6,004,741 | A | 12/1999 | Wollowitz |
| 6,004,742 | A | 12/1999 | Wollowitz |
| 6,017,691 | A | 1/2000 | Wollowitz et al. |
| 6,093,725 | A | 7/2000 | Cook et al. |
| 6,099,734 | A | 8/2000 | Mclarty |
| 6,133,460 | A | 10/2000 | Wollowitz |
| 6,136,586 | A | 10/2000 | Budowsky |
| 6,143,490 | A | 11/2000 | Cook et al. |
| 6,171,777 | B1 | 1/2001 | Cook |
| 6,177,441 | B1 | 1/2001 | Cook et al. |
| 6,194,139 | B1 | 2/2001 | Wollowitz |
| 6,218,100 | B1 | 4/2001 | Wollowitz |
| 6,251,580 | B1 | 6/2001 | Lin |
| 6,270,952 | B1 | 8/2001 | Cook et al. |
| 6,281,225 | B1 | 8/2001 | Hearst et al. |
| 6,364,864 | B1 | 4/2002 | Mohiuddin |
| 6,410,219 | B1 | 6/2002 | Cook et al. |
| 6,420,570 | B1 | 7/2002 | Wollowitz |
| 6,433,343 | B1 | 8/2002 | Cimino et al. |
| 6,455,286 | B1 | 9/2002 | Wollowitz |
| 6,469,052 | B2 | 10/2002 | Wollowitz |
| 6,494,753 | B1 | 12/2002 | Tomasino et al. |
| 6,503,699 | B1 | 1/2003 | Wollowitz et al. |
| 6,514,987 | B1 | 2/2003 | Cook et al. |
| 6,544,727 | B1 | 4/2003 | Hei |
| 6,565,802 | B1 | 5/2003 | Hanley |
| 6,586,749 | B2 | 7/2003 | Cimino |
| 6,617,157 | B1 | 9/2003 | Budowsky |
| 6,686,480 | B2 | 2/2004 | Wollowitz |
| 6,709,810 | B2 | 3/2004 | Cook |
| 6,936,413 | B1 | 8/2005 | Bischof |
| 6,949,753 | B2 | 9/2005 | Cimino |
| 6,951,713 | B2 | 10/2005 | Hei et al. |
| 7,025,877 | B1 | 4/2006 | De |
| 7,037,642 | B2 | 5/2006 | Hei et al. |
| 7,068,361 | B2 | 6/2006 | Cimino |
| 7,264,608 | B2 | 9/2007 | Bischof |
| 7,293,985 | B2 | 11/2007 | Cook |
| 7,445,756 | B2 | 11/2008 | Moore |
| 7,534,348 | B2 | 5/2009 | Reitz |
| 7,611,831 | B2 | 11/2009 | Hei |
| 7,655,392 | B2 | 2/2010 | Stassinopoulos |
| 8,900,805 | B2 | 12/2014 | Mufti et al. |
| 9,259,525 | B2 | 2/2016 | Hei |
| 9,713,627 | B2 | 7/2017 | Mufti |
| 10,357,516 | B2 | 7/2019 | Mufti |
| 10,799,533 | B2 | 10/2020 | Corash |
| 10,842,818 | B2 | 11/2020 | Vermeij |
| 11,096,963 | B2 | 8/2021 | Corash et al. |
| 2001/0009756 | A1 | 7/2001 | Hei |
| 2001/0018179 | A1 | 8/2001 | Hei |
| 2002/0006393 | A1 | 1/2002 | Wollowitz |
| 2002/0028432 | A1 | 3/2002 | Cook |
| 2002/0042043 | A1 | 4/2002 | Stassinopoulos |
| 2002/0115585 | A1 | 8/2002 | Hei |
| 2002/0192632 | A1 | 12/2002 | Hei |
| 2003/0062483 | A1 | 4/2003 | Cimino |
| 2003/0105339 | A1 | 6/2003 | Wollowitz |
| 2003/0113704 | A1 | 6/2003 | Stassinopoulos |
| 2003/0185804 | A1 | 10/2003 | Wollowitz et al. |
| 2003/0207247 | A1 | 11/2003 | Stassinopoulos |
| 2004/0021809 | A1 | 2/2004 | Sumiyoshi et al. |
| 2004/0029897 | A1 | 2/2004 | Cook |
| 2004/0180321 | A1 | 9/2004 | Cook |
| 2004/0185544 | A9 | 9/2004 | Hei |
| 2004/0185553 | A9 | 9/2004 | Hei |
| 2004/0197343 | A1 | 10/2004 | Dubensky et al. |
| 2004/0228877 | A1 | 11/2004 | Dubensky et al. |
| 2005/0142542 | A1 | 6/2005 | Hei |
| 2005/0175625 | A1 | 8/2005 | Jaffee et al. |
| 2005/0249748 | A1 | 11/2005 | Dubensky et al. |
| 2005/0281783 | A1 | 12/2005 | Kinch et al. |
| 2006/0093999 | A1 | 5/2006 | Hei |
| 2006/0115466 | A1 | 6/2006 | Stassinopoulos |
| 2007/0031457 | A1 | 2/2007 | Dubensky et al. |
| 2007/0190029 | A1 | 8/2007 | Pardoll et al. |
| 2007/0190063 | A1 | 8/2007 | Bahjat et al. |
| 2007/0207170 | A1 | 9/2007 | Dubensky et al. |
| 2007/0207171 | A1 | 9/2007 | Dubensky et al. |
| 2010/0133160 | A1 | 6/2010 | Hei |
| 2011/0286987 | A1* | 11/2011 | Mufti ........................ A61P 7/00 424/93.73 |
| 2013/0327712 | A1* | 12/2013 | DelGiacco ............ A61M 5/165 210/435 |
| 2015/0111277 | A1* | 4/2015 | Hamman ............ A61M 1/3693 422/534 |
| 2015/0157665 | A1 | 6/2015 | Mufti |
| 2016/0199831 | A1* | 7/2016 | Codisco .................. B01F 31/10 435/325 |
| 2016/0354533 | A1 | 12/2016 | Hei |
| 2017/0027986 | A1 | 2/2017 | Corash et al. |
| 2017/0202882 | A1 | 7/2017 | Vermeij |
| 2017/0304363 | A1 | 10/2017 | Corash |
| 2018/0008639 | A1 | 1/2018 | Mufti |
| 2018/0185484 | A1 | 7/2018 | Greenman |
| 2018/0289873 | A1 | 10/2018 | David |
| 2018/0318348 | A1 | 11/2018 | Corash |
| 2019/0085289 | A1 | 3/2019 | Greenman |
| 2019/0209718 | A1 | 7/2019 | Church |
| 2019/0321407 | A1* | 10/2019 | Erickson .............. A61K 38/063 |
| 2019/0369087 | A1 | 12/2019 | North et al. |
| 2020/0078406 | A1 | 3/2020 | Weiner et al. |
| 2020/0197588 | A1* | 6/2020 | Murata ............... A61M 1/0281 |
| 2020/0397931 | A1 | 12/2020 | Church et al. |
| 2020/0397935 | A1 | 12/2020 | Church et al. |
| 2020/0405891 | A1 | 12/2020 | Church et al. |
| 2021/0187020 | A1 | 6/2021 | Corash et al. |
| 2021/0227827 | A1* | 7/2021 | Tabatadze .............. A01N 25/32 |
| 2021/0260114 | A1 | 8/2021 | Corash et al. |
| 2021/0322479 | A1 | 10/2021 | Vermeij |
| 2022/0118136 | A1 | 4/2022 | Church et al. |

FOREIGN PATENT DOCUMENTS

| | | | |
|---|---|---|---|
| EP | 0804074 | B1 | 1/2005 |
| WO | 199317553 | A1 | 9/1993 |
| WO | 199403054 | A1 | 2/1994 |
| WO | 199427433 | A1 | 12/1994 |
| WO | 199500141 | A1 | 1/1995 |
| WO | 199512973 | A1 | 5/1995 |
| WO | 199519705 | A1 | 7/1995 |
| WO | 199614737 | A1 | 5/1996 |
| WO | 199614739 | A1 | 5/1996 |

(56) References Cited

FOREIGN PATENT DOCUMENTS

| | | | |
|---|---|---|---|
| WO | 199614740 | A1 | 5/1996 |
| WO | 199639818 | A1 | 12/1996 |
| WO | 199721346 | A1 | 6/1997 |
| WO | 199830327 | A1 | 7/1998 |
| WO | 199830545 | A1 | 7/1998 |
| WO | 199903976 | A2 | 1/1999 |
| WO | 199903976 | A3 | 5/1999 |
| WO | 199926476 | A1 | 6/1999 |
| WO | 199934839 | A1 | 7/1999 |
| WO | 199934914 | A1 | 7/1999 |
| WO | 199934915 | A1 | 7/1999 |
| WO | 199963981 | A2 | 12/1999 |
| WO | 199963981 | A3 | 4/2000 |
| WO | 200191775 | A2 | 12/2001 |
| WO | 200191775 | A3 | 6/2002 |
| WO | 200347650 | A2 | 6/2003 |
| WO | 200361379 | A2 | 7/2003 |
| WO | 200365787 | A2 | 8/2003 |
| WO | 2003078023 | A1 | 9/2003 |
| WO | 200361379 | A3 | 10/2003 |
| WO | 200365787 | A3 | 12/2003 |
| WO | 200347650 | A3 | 2/2004 |
| WO | 2004049914 | A2 | 6/2004 |
| WO | 2004050029 | A2 | 6/2004 |
| WO | 2004050848 | A2 | 6/2004 |
| WO | 2004050897 | A2 | 6/2004 |
| WO | 2004050897 | A3 | 8/2004 |
| WO | 2004050029 | A3 | 10/2004 |
| WO | 2004084936 | A2 | 10/2004 |
| WO | 2004050848 | A3 | 12/2004 |
| WO | 2004110481 | A2 | 12/2004 |
| WO | 2004049914 | A3 | 2/2005 |
| WO | 2005009463 | A2 | 2/2005 |
| WO | 2004110481 | A3 | 3/2005 |
| WO | 2005037233 | A2 | 4/2005 |
| WO | 2004084936 | A3 | 6/2005 |
| WO | 2005009463 | A3 | 6/2005 |
| WO | 2005067460 | A2 | 7/2005 |
| WO | 2005071088 | A2 | 8/2005 |
| WO | 2005092372 | A2 | 10/2005 |
| WO | 2005071088 | A3 | 11/2005 |
| WO | 2005037233 | A3 | 1/2006 |
| WO | 2006050328 | A1 | 5/2006 |
| WO | 2005092372 | A3 | 6/2006 |
| WO | 2005067460 | A3 | 10/2006 |
| WO | 2007022511 | A2 | 2/2007 |
| WO | 2007022520 | A2 | 2/2007 |
| WO | 2007022520 | A3 | 5/2007 |
| WO | 2007022511 | A3 | 9/2007 |
| WO | 2007103225 | A2 | 9/2007 |
| WO | 2007103261 | A2 | 9/2007 |
| WO | 2007117371 | A2 | 10/2007 |
| WO | 2007103225 | A3 | 5/2008 |
| WO | 2007103261 | A3 | 12/2008 |
| WO | 2007117371 | A3 | 12/2008 |
| WO | 2009018309 | A2 | 2/2009 |
| WO | 2009026073 | A1 | 2/2009 |
| WO | 2009126786 | A2 | 10/2009 |
| WO | 2009126786 | A3 | 7/2010 |
| WO | 2016014854 | A1 | 1/2016 |
| WO | 2016057965 | A1 | 4/2016 |
| WO | 2016115535 | A1 | 7/2016 |
| WO | 2016210374 | A1 | 12/2016 |
| WO | 2017070619 | A1 | 4/2017 |
| WO | 2017120545 | A2 | 7/2017 |
| WO | 2017120545 | A3 | 8/2017 |
| WO | 2018119462 | A1 | 6/2018 |
| WO | 2018125994 | A1 | 7/2018 |
| WO | 2018161020 | A1 | 9/2018 |
| WO | 2019060610 | A1 | 3/2019 |
| WO | 2019133929 | A1 | 7/2019 |
| WO | 2020023881 | A1 | 1/2020 |
| WO | 2020263745 | A1 | 12/2020 |
| WO | 2020263759 | A2 | 12/2020 |
| WO | 2020264421 | A1 | 12/2020 |
| WO | 2020263759 | A3 | 1/2021 |
| WO | 2022087580 | A1 | 4/2022 |

OTHER PUBLICATIONS

International Preliminary Report on Patentability, issued Mar. 23, 2021, for PCT Application No. PCT/US2019/052286, filed Sep. 20, 2019, 11 pages.

International Search Report and Written Opinion, mailed Mar. 3, 2020, for PCT Application No. PCT/US2019/052286, filed Sep. 20, 2019, 17 pages.

Invitation To Pay Additional Fees, mailed Jan. 10, 2020, for PCT Application No. PCT/US2019/052286, filed Sep. 20, 2019, 17 pages.

U.S. Appl. No. 09/238,355, Greenman, W. et al, filed on Jan. 27, 1999. (Copy not submitted herewith pursuant to the waiver of 37 C.F.R. § 1.98(a)(2)(iii) issued by the Office on Sep. 21, 2004.).

Brixner, V. et al. (Apr. 2018, e-pub. Mar. 1, 2018). "Red Blood Cells Treated with the Amustaline (S-303) Pathogen Reduction System: A Transfusion Study in Cardiac Surgery," Transfusion 58(4):905-916.

Extended European search report dated Jun. 8, 2026, for EP Application No. 26150623.2, ten pages.

* cited by examiner 100
145
Infusion
125
Quencher
140
130
142
115
105
110
120
PIC
135
150
152
WB 100
145
Infusion
Quencher
125
155
140
130
142
115
105
110
150
135
PIC
120
152
WB 100
145
Infusion
155
125
Quencher
130
142
115
105
110
120
PIC
150
152
WB 200
245
Infusion
225
Quencher
240
230
212
215
205
220
PIC
235
210
242
250
WB
252

200
Infusion
245
Quencher
225
255
212
215
205
230
PIC
220
210
265
261
260

300
345
Infusion
307
317
319
316
332
315
325
Quencher
340
330
342
310
305
350
320
PIC
335
352
WB 300
345
Infusion
307
317
319
316
332
315
305
310
342
350
WB
352
330
340
325
Quencher
355
335
PIC
320

300
345
Infusion
307
317
319
316
332
315
325
Quencher
355
330
342
310
305
350
320
PIC
352
WB 400
445
Infusion
407
417
419
416
425
Quencher
432
440
415
412
430
435
PIC
420
442
410
450
405
452
WB 400
445
Infusion
407
417
419
416
425
Quencher
455
440
432
412
415
430
435
410
442
450
405
420
PIC
452
WB 400
445
Infusion
407
417
416
419
432
415
405
425
Quencher
455
412
430
410
PIC
420
442
450
452
WB 400
445
Infusion
407
417
419
416
432
Quencher
425
455
412
415
430
410
405
PIC
420
442
450
452
WB 500
545
Infusion
507
517
519
516
532
525
Quencher
540
512
515
530
535
PIC
520
510
505
565
561
560

500
545
Infusion
507
517
519
516
532
525
Quencher
555
540
512
515
530
535
520
PIC
510
505
565
561
560

500
545
Infusion
507
517
519
516
532
525
Quencher
555
515
512
530
510
505
565
520
PIC
561
560

500
Infusion
Quencher
PIC
545
507
517
519
516
532
525
555
540
512
515
530
535
520
510
505
565
561
560

500
Infusion
545
507
517
519
516
532
525
Quencher
555
512
515
530
510
520
PIC
505
565
560
561

500
Infusion
545
507
517
519
516
532
515
512
PIC
520
530
510
505
565
560
561

METHODS AND KITS FOR PREPARING PATHOGEN-INACTIVATED WHOLE BLOOD

CROSS-REFERENCE TO RELATED APPLICATIONS

This application is a national stage application under 35 U.S.C. § 371 of International Application No. PCT/US2019/052286, filed internationally on Sep. 20, 2019, which claims the priority benefit of U.S. Provisional Application No. 62/734,117, filed Sep. 20, 2018, the disclosures of each of which are incorporated herein by reference in their entirety.

TECHNICAL FIELD

The present disclosure relates to pathogen-inactivated whole blood and improved methods and kits for preparing pathogen-inactivated whole blood and other blood product compositions.

BACKGROUND

Pathogen inactivation (PI) technologies increasingly are being used to treat blood products to help mitigate the risk of transfusion transmitted infection and complications arising from donor leukocytes. At least three PI technologies available commercially in certain countries utilize ultraviolet light, either in the presence or absence of a pathogen inactivation compound (e.g., photosensitizer), for treatment of one or more blood products, such as plasma, platelets, red blood cells and/or whole blood (see e.g., Schubert, 2018; Schlenke, 2014; Prowse 2013). Such PI technologies include, for example, the amotosalen/UV based INTERCEPT® system (Cerus), the riboflavin/UV based Mirasol® system (TerumoBCT) and the UVC light only based Theraflex® system (Macopharma). At least one other PI technology in late stage clinical development for treatment of red blood cells (RBCs) also targets nucleic acids, by utilizing frangible pathogen-inactivation compounds (e.g., S-303), but without the need for ultraviolet light (Henschler 2011).

Exemplary frangible PI compounds are described in more detail in U.S. Pat. Nos. 6,093,725 and 6,514,987. The INTERCEPT® Blood System for RBCs utilizes the frangible nucleic acid targeted alkylator compound S-303 (e.g., amustaline) for pathogen inactivation. Amustaline is a modular compound comprising an acridine anchor (e.g., intercalator that targets nucleic acids), an effector (e.g., bis alkylator group that reacts with nucleophiles such as DNA bases) and a linker (e.g., small flexible carbon chain that contains a labile ester bond that can hydrolyze at neutral pH). The anchor targets nucleic acids of pathogens and cells by intercalating into helical regions, with the effector rapidly (e.g., minutes) reacting with nucleic acid bases to form mono adducts and then cross links that block replication. Within hours, the linker can hydrolyze, resulting in the dissociation of the anchor from the effector. The INTERCEPT® Blood System for RBCs further includes a quencher, such as for example glutathione (GSH), to reduce non-specific binding of amustaline (Henschler 2011; U.S. Pat. No. 8,900,805). Following mixing of a donor RBC unit, amustaline, GSH and a processing solution, the admixture is transferred to an incubation bag, incubated at room temperature for 18-24 hours for pathogen inactivation and amustaline hydrolysis, and then centrifuged, with the solution containing residual non-hydrolyzed amustaline, GSH, processing solution subsequently removed and replaced with a red blood cell additive solution prior to storage.

PI treatment with the pathogen inactivation compound amustaline and GSH also has been demonstrated for whole blood units. However, for whole blood PI treatment, similar post-incubation steps of centrifugation and solution replacement with fresh additive solution as used for treatment of red blood cells cannot be performed, and therefore residual non-hydrolyzed amustaline and GSH is not removed or reduced by such solution replacement step, which may preclude the use of the PI treated whole blood units for infusion into a subject if the residual amustaline remains above certain concentrations in treated units. Additionally, volume limitations for amustaline and GSH addition to whole blood for pathogen inactivation compared to red blood cell treatment processes may affect dosing and benefit from processing kits modifications that better facilitate transfer of compounds. Finally, current pathogen inactivation technologies, including the amustaline/GSH system, may have certain limitations for use, particularly in geographic areas which can lack access to suitable facilities, and in war zones where blood components are not easily available or treatable. PI technologies generally require suitable power sources and equipment for one or more processing steps, including for example an illumination device to provide ultraviolet light exposure during processing (e.g., amotosalen/UV and riboflavin/UV systems) and/or devices for other processing steps, such as for example, the use of sterile docking (e.g., tubing welding) devices to connect blood product containing bags to a PI system (e.g., to a kit, to a processing set) and/or centrifuges, incubators, rockers, agitators or other equipment. Therefore, modifications to PI technologies and related processing kits that could lead to further improvements in the pathogen inactivation of blood products (e.g., whole blood) are desirable, such as by reducing residual levels of PI compounds in treated products, improving dosing of PI compounds and quenchers into blood products, and/or providing an opportunity to conduct PI treatment without the need for equipment that may require a power source, or which require only modest power supply such as from a portable battery source.

SUMMARY

To meet these and other needs, the methods, kits and compositions described herein are useful, inter alia, for preparing pathogen inactivated whole blood and other pathogen inactivated blood product (e.g., RBC, plasma, cryoprecipitate) compositions, including for example, pathogen inactivated whole blood compositions with decreased residual levels of pathogen inactivation compound in the composition, which may be particularly beneficial for subsequent infusion (e.g., infusion of the PI treated whole blood compositions).

In one aspect, the present disclosure provides a method of preparing a pathogen inactivated whole blood composition, comprising: (a) mixing (e.g., combining, adding) in a first container (i) a whole blood composition, (ii) an effective amount of a pathogen inactivation compound (PIC), and optionally (iii) an effective amount of a quencher; (b) incubating in the first container the mixture (e.g., admixture) of the whole blood composition, the PIC and optionally the quencher, under conditions and for a time sufficient to inactivate a pathogen, if present; (c) transferring the mixture under sterile conditions to a second container; and (d) incubating in the second container the mixture under conditions and for a time sufficient such that at least one of (i)-(iii) applies: (i) the concentration of the PIC after incubating in the second container is at least 25% less than the concentration of the PIC in the mixture at the time of transfer step (b); (ii) the concentration of the PIC after incubating in the second container is at least $10^5$ fold less than (e.g., lower than) the concentration (e.g., initial concentration, concentration prior to the incubating step (b)) of the PIC in the mixture of step (a); or (iii) the concentration of the PIC after incubating in the second container is about 1 nM or less, thereby yielding the pathogen inactivated whole blood composition. In some embodiments, the method comprises: (a) mixing (e.g., combining, adding) in a first container (i) a whole blood composition and (ii) an effective amount of a pathogen inactivation compound (PIC); (b) incubating in the first container the mixture of the whole blood composition and the PIC, under conditions and for a time sufficient to inactivate a pathogen, if present; (c) transferring the mixture under sterile conditions to a second container; and (d) incubating in the second container the mixture under conditions and for a time sufficient such that at least one of (i)-(iii) applies: (i) the concentration of the PIC after incubating in the second container is at least 25% less than the concentration of the PIC in the mixture at the time of transfer step (b); (ii) the concentration of the PIC after incubating in the second container is at least $10^5$ fold less than the concentration of the PIC in the mixture of step (a); or (iii) the concentration of the PIC after incubating in the second container is about 1 nM or less, thereby yielding the pathogen inactivated whole blood composition. In some embodiments, the method comprises: (a) mixing (e.g., combining, adding) in a first container (i) a whole blood composition, (ii) an effective amount of a pathogen inactivation compound (PIC), and (iii) an effective amount of a quencher; (b) incubating in the first container the mixture of the whole blood composition, the PIC and the quencher, under conditions and for a time sufficient to inactivate a pathogen, if present; (c) transferring the mixture under sterile conditions to a second container; and (d) incubating in the second container the mixture under conditions and for a time sufficient such that at least one of (i)-(iii) applies: (i) the concentration of the PIC after incubating in the second container is at least 25% less than the concentration of the PIC in the mixture at the time of transfer step (b); (ii) the concentration of the PIC after incubating in the second container is at least $10^5$ fold less than the concentration of the PIC in the mixture of step (a); or (iii) the concentration of the PIC after incubating in the second container is about 1 nM or less, thereby yielding the pathogen inactivated whole blood composition. In some embodiments, the method further comprises (e.g., after incubating step (d)) storing the pathogen inactivated whole blood composition under refrigeration conditions (e.g., storing refrigerated, storing at between about 2° C. and about 6° C.).

In some embodiments, the concentration (e.g., initial concentration, concentration prior to the incubating step (b)) of the PIC in the mixture (e.g., admixture) of step (a) is at least about 0.1 mM. In some embodiments, the concentration of the PIC in the mixture of step (a) is about 0.1 mM to about 10 mM. In some embodiments, the concentration of the PIC in the mixture of step (a) is about 0.1 mM to about 1.0 mM. In some embodiments, the concentration of the PIC in the mixture of step (a) is about 0.2 mM to about 0.5 mM. In some embodiments, the concentration of the PIC in the mixture of step (a) is about 0.2 mM. In some embodiments, the concentration of the PIC after incubating in the second container is at least 25% less than the concentration of the PIC in the mixture at the time of transfer step (b). In some embodiments, the concentration of the PIC after incubating in the second container is at least 50% less than the concentration of the PIC in the mixture at the time of transfer step (b). In some embodiments, the concentration of the PIC after step (d) is at least 25% less than the concentration of the PIC in the mixture at the time of transfer step (b). In some embodiments, the concentration of the PIC after step (d) is at least 50% less than the concentration of the PIC in the mixture at the time of transfer step (b). In some embodiments, the concentration of the PIC after incubating in the second container is at least $10^5$ fold less than the concentration of the PIC in the mixture of step (a). In some embodiments, the concentration of the PIC after step (d) is at least $10^5$ fold less than the concentration of the PIC in the mixture of step (a). In some embodiments, the concentration of the PIC after incubating in the second container is about 1 nM or less. In some embodiments, the concentration of the PIC after incubating in the second container is less than about 1 nM. In some embodiments, the concentration of the PIC after incubating in the second container is about 0.75 nM or less. In some embodiments, the concentration of the PIC after incubating in the second container is less than about 0.75 nM. In some embodiments, the concentration of the PIC after step (d) is less than about 2 nM. In some embodiments, the concentration of the PIC after step (d) is less than about 1 nM. In some embodiments, the concentration of the PIC after step (d) is less than about 0.75 nM. In some embodiments, the PIC comprises a functional group which is, or which forms, a reactive electrophilic group. In some embodiments, the functional group is selected from the group consisting of a mustard, a mustard intermediate, and a mustard equivalent. In some embodiments, the functional group is, or is capable of forming, an aziridinium ion. In some embodiments, the reactive electrophilic group is capable of reacting with nucleic acids. In some embodiments, the PIC comprises a nucleic acid binding ligand. In some embodiments, the nucleic acid binding ligand is an intercalator. In some embodiments, the intercalator is an acridine. In some embodiments, the PIC comprises a frangible linker linking the functional group and the nucleic acid binding ligand. In some embodiments, the PIC is β-alanine, N-(acridin-9-yl), 2-[bis(2-chloroethyl)amino]ethyl ester.

In some embodiments, step (a) comprises mixing (e.g., combining, adding) in the first container a whole blood composition, an effective amount of a PIC, and an effective amount of a quencher. In some embodiments, the concentration (e.g., initial concentration, concentration prior to the incubating step (b)) of the quencher in the mixture (e.g., admixture) of step (a) is at least about 1 mM. In some embodiments, the concentration of the quencher in the mixture of step (a) is about 1 mM to about 10 mM. In some embodiments, the concentration of the quencher in the mixture of step (a) is about 2 mM. In some embodiments, the concentration of the PIC in the mixture of step (a) is about 0.2 mM and the concentration of the quencher in the mixture of step (a) is about 2 mM. In some embodiments, the molar ratio of the concentration of the quencher and the concentration of the PIC in the mixture of step (a) is about 5:1 to about 20:1 quencher to PIC. In some embodiments, the molar ratio of the concentration of the quencher and the concentration of the PIC in the mixture of step (a) is about 5:1, about 6:1, about 7:1, about 8:1, about 9:1, about 10:1, about 11:1, about 12:1, about 13:1, about 14:1, about 15:1, about 16:1, about 17:1, about 18:1, about 19:1 or about 20:1 quencher to PIC. In some embodiments, the molar ratio of the concentration of the quencher and the concentration of the PIC in the mixture of step (a) is about 10:1 quencher to PIC. In some embodiments, the quencher comprises a thiol group, wherein the thiol is capable of reacting with a reactive electrophilic group of the pathogen inactivation compound. In some embodiments, the quencher comprises cysteine or a derivative of cysteine. In some embodiments, the quencher is glutathione or a pharmaceutically acceptable salt thereof. In some embodiments, the quencher is glutathione monosodium salt.

In some embodiments, the mixture of step (a) further comprises an anticoagulant. In some embodiments, the whole blood composition further comprises an anticoagulant (e.g., anticoagulant solution). In some embodiments, the first container contains an anticoagulant and the whole blood composition is mixed with the anticoagulant in the first container (e.g., prior to mixing whole blood composition with the PIC). In some embodiments, the whole blood composition (e.g., including a coagulant) has a volume of about 250 mL to about 700 mL. In some embodiments, the whole blood composition has a volume of about 400 mL to about 600 mL. In some embodiments, the ratio of anticoagulant to whole blood (e.g., in a whole blood composition) is about 1:5 to about 1:9. In some embodiments, the ratio of anticoagulant to whole blood is about 1:7.

In some embodiments, the whole blood composition is added (e.g., introduced, transferred) into the first container through a first inlet of the first container. In some embodiments, the whole blood composition is added into the first container from a donor collection container containing the whole blood composition (e.g., whole blood collection container). In some embodiments, the whole blood composition is added into the first container from a donor collection container containing the whole blood composition that is coupled to the first container (e.g., a first inlet in the first container). In some embodiments, the whole blood composition is added into the first container from a donor collection container containing the whole blood composition through a conduit (e.g., tubing segment(s) extending between, connecting, providing a fluid communication path) between the donor collection container and the first container (e.g., a first inlet of the first container). In some embodiments, the whole blood composition is added into the first container by collecting the whole blood composition from a donor (e.g., whole blood donor) into the first container (e.g., directly into the first container, without first collecting into an intermediate container, without first collecting into a donor collection container).

In some embodiments, the whole blood composition is collected from a whole blood donor into the first container. In some embodiments, the whole blood composition is a whole blood donation collected from a donor into the first container (e.g., directly into the first container, without prior collection into a different container). In some embodiments, the whole blood composition is collected from a donor into the first container through a first conduit (e.g., tubing segment(s)). In some embodiments, the whole blood composition is a whole blood donation collected from a donor into the first container using a vascular access device (e.g., needle, venipuncture needle), such as for example a vascular access device connected to the a container (e.g., first container) by way of a conduit (e.g., tubing, tubing segment(s)) extending between the vascular access device and the first container (e.g., and providing a fluid communication path from or through a vascular access device to the first container). In some embodiments, the whole blood composition is collected from a whole blood donor into the first container through a first conduit extending between a vascular access device (e.g., needle, venipuncture device) and the first container (e.g., a first inlet of the first container) and providing a fluid communication path for transferring the whole blood composition from the donor (e.g., from the vascular access device, through the vascular access device) into the first container. In some embodiments, the vascular access device (e.g., needle) and conduit extending therefrom comprise a needle assembly.

In some embodiments, the PIC and optionally the quencher (e.g., the PIC and the quencher) are added into the first container through an inlet (e.g., a first inlet, a second inlet) of the first container. In some embodiments, the PIC and optionally the quencher (e.g., the PIC and the quencher) are added into the first container after the whole blood composition is added into the first container. In some embodiments, the PIC and the quencher are added into the first container (e.g., added to the whole blood composition) sequentially. In some embodiments, the PIC is added into the first container (e.g., added to the whole blood composition) before the quencher. In some embodiments, the quencher is added into the first container (e.g., added to the whole blood composition) before the PIC. In some embodiments, the PIC and optionally the quencher (e.g., the PIC and the quencher) are added into the first container through a first inlet of the first container after the whole blood composition is added into the first container through a first inlet of the first container. In some embodiments, the PIC and optionally the quencher (e.g., the PIC and the quencher) are added into the first container through a second inlet in the first container. In some embodiments, the PIC and optionally the quencher (e.g., the PIC and the quencher) are added into the first container through a conduit (e.g., tubing segment(s)) extending between a container containing the PIC (PIC container) and optionally a container containing the quencher (quencher container) and an inlet of the first container, and providing a fluid communication path for transferring the PIC from the PIC container, and optionally for transferring the quencher from the optional quencher container, into the first container. In some embodiments, the PIC is added into the first container through a conduit (e.g., tubing, tubing segment(s)) extending between a PIC container and an inlet (e.g., first inlet, second inlet) of the first container (e.g., and providing a fluid communication path for transferring the PIC from the PIC container into the first container). In some embodiments, the conduit comprises at one end (e.g., opposite the first container connection end): (a) a first adaptor for coupling (e.g., connecting) the PIC container to the conduit, and optionally (b) a displacement device (e.g., an air displacement device) suitable for increasing the transfer of the PIC into the first container (e.g., through the conduit and into the first container). In some embodiments, the PIC and the quencher are added into the first container through a conduit (e.g., tubing, tubing segment(s)) extending between a PIC container and a quencher container and an inlet (e.g., first inlet, second inlet) of the first container, and providing a fluid communication path for transferring the PIC from the PIC container and the quencher from the quencher container, into the first container. In some embodiments, the PIC and the quencher are added into the first container through a conduit extending between a PIC container and a quencher container and an inlet of the first container, and wherein the conduit comprises at one end (e.g., opposite the first container connection end): (a) a first adaptor for coupling (e.g., connecting) the PIC container to the conduit, (b) a second adaptor for coupling (e.g., connecting) the quencher container to the conduit, and optionally (c) a displacement device (e.g., an air displacement device) suitable for increasing the transfer of the PIC and the quencher into the first container (e.g., through the conduit and into the first container). In some embodiments, the PIC and the quencher are added into the first container through a conduit extending between a PIC container and a quencher container and an inlet of the first container, and wherein the conduit comprises at one end (e.g., opposite the first container connection end): (a) a first adaptor for coupling (e.g., connecting) the PIC container to the conduit, (b) a second adaptor for coupling (e.g., connecting) the quencher container to the conduit, and (c) a displacement device (e.g., an air displacement device) suitable for increasing the transfer of the PIC and the quencher into the first container (e.g., through the conduit and into the first container). In some embodiments, the PIC container and the quencher container are the same container (e.g., container with separate chambers for the PIC and quencher).

In some embodiments, the incubating step (b) is about 2 hours to about 24 hours. In some embodiments, the incubating step (b) is about 18 hours to about 22 hours. In some embodiments, the incubating step (b) is about 20 hours. In some embodiments, the incubating step (b) is at room temperature (e.g., 20°-25° C., 22° C.). In some embodiments, the transferring step (c) is through a conduit extending between (e.g., connecting) the first container to the second container. In some embodiments, the conduit connects (e.g., provides a fluid communication path between) a first outlet of the first container to a first inlet of the second container. In some embodiments, the incubating step (d) is about 1 hour to about 8 hours. In some embodiments, the incubating step (d) is about 2 hours to about 4 hours. In some embodiments, the incubating step (d) is at substantially the same temperature as the incubating step (b). In some embodiments, the incubating step (d) is at room temperature (e.g., 20°-25° C., 22° C.).

In some embodiments, the method further comprises transferring the pathogen-inactivated whole blood composition from the second container to a third container. In some embodiments, the method further comprises: (e) storing the pathogen inactivated whole blood composition at about 2-6° C. (e.g., in the second container, in the third container, after incubating step (d)). In some embodiments, the pathogen-inactivated whole blood composition is suitable for infusion (e.g., into a subject). In some embodiments, the method further comprises preparing from the pathogen-inactivated whole blood composition (e.g., separating the pathogen-inactivated whole blood composition into) one or more of a red blood cell composition, a plasma composition, or a platelet composition. In some embodiments, the method further comprises preparing a cryoprecipitate composition from the pathogen inactivated whole blood composition. In some embodiments, the method further comprises preparing from the pathogen-inactivated whole blood composition (e.g., separating the pathogen-inactivated whole blood composition into) a plasma composition, and preparing a cryoprecipitate composition from the plasma composition.

In some embodiments, the first container (e.g., container sheeting material) comprises a polyvinyl chloride (e.g., plasticized polyvinyl chloride). In some embodiments, the first container comprises a polyethylene (e.g., ethylene vinyl acetate, ethylene vinyl acetate copolymer). In some embodiments, the first container comprises a polyolefin (e.g., polyolefin blend). In some embodiments, the second container (e.g., container sheeting material) comprises a polyvinyl chloride (e.g., plasticized polyvinyl chloride). In some embodiments, the second container comprises a polyethylene (e.g., ethylene vinyl acetate, ethylene vinyl acetate copolymer). In some embodiments, the second container comprises a polyolefin (e.g., polyolefin blend). In some embodiments, the first container and/or the second container does not comprise di-ethylhexyl phthalate.

In another aspect, the present disclosure provides a pathogen-inactivated whole blood composition prepared by any of the aforementioned methods. In some embodiments, the pathogen-inactivated whole blood composition is suitable for infusion. In some embodiments, the pathogen-inactivated whole blood composition is a pathogen-inactivated whole blood unit suitable for infusion. Another aspect of the present disclosure provides a pathogen-inactivated red blood cell composition (e.g., pathogen inactivated red blood cell composition suitable for infusion) prepared by any of the aforementioned methods. Another aspect of the present disclosure provides a pathogen-inactivated plasma composition (e.g., pathogen inactivated plasma composition suitable for infusion) prepared by any of the aforementioned methods. Another aspect of the present disclosure provides a pathogen-inactivated platelet composition (e.g., pathogen inactivated platelet composition suitable for infusion) prepared by any of the aforementioned methods. Another aspect of the present disclosure provides a pathogen-inactivated cryoprecipitate composition (e.g., pathogen inactivated cryoprecipitate composition suitable for infusion) prepared by any of the aforementioned methods.

In another aspect, the present disclosure provides a method of infusing a pathogen-inactivated whole blood composition into a subject in need thereof, the method comprising infusing into the subject a pathogen-inactivated whole blood composition prepared by any of the aforementioned methods, or an aforementioned pathogen-inactivated whole blood composition. In some embodiments, the method of infusing a pathogen-inactivated whole blood composition is by infusing the pathogen-inactivated whole blood composition through a conduit (e.g., infusion line, infusion line assembly) coupled (e.g., connected) to an outlet (e.g., first outlet, spike port) of the container containing the pathogen-inactivated whole blood composition (e.g., second container, third container). In some embodiments, the method of infusing a pathogen-inactivated whole blood composition comprises infusing the pathogen-inactivated whole blood composition through an infusion line assembly coupled to the second container. In some embodiments, the method of infusing a pathogen-inactivated whole blood composition comprises coupling (e.g., connecting) an infusion line (e.g., infusion line assembly) to an outlet (e.g., a first outlet, spike port) of the second container and infusing the pathogen-inactivated whole blood composition into the subject. In some embodiments, the method of infusing a pathogen-inactivated whole blood composition comprises coupling an infusion line assembly to the second container and infusing the pathogen-inactivated whole blood composition into the subject. In some embodiments, the method of infusing a pathogen-inactivated whole blood composition comprises coupling an infusion line assembly to the third container and infusing the pathogen-inactivated whole blood composition into the subject. In some embodiments, the method of infusing a pathogen-inactivated whole blood composition comprises infusing a pathogen-inactivated whole blood composition prepared by any of the methods and/or any of the kits of the present disclosure into a subject suffering from a trauma (e.g., for trauma resuscitation). In some embodiments, the subject is acutely hemorrhaging due to trauma. In some embodiments, the subject is a trauma patient presenting with systolic blood pressure <100 mmHg, <90 mmHg, or less than 80 mmHg. In some embodiments, the pathogen-inactivated whole blood composition is ABO compatible with the subject. In some embodiments, the pathogen-inactivated whole blood composition is RhD compatible with the subject. In some embodiments, the pathogen-inactivated whole blood composition is from a Group O donor. In some embodiments, the method of infusing comprises administering two or more infusions (e.g., two or more units) of a pathogen-inactivated whole blood composition prepared by any of the methods and/or using any of the kits of the present disclosure. In some embodiments, the pathogen-inactivated whole blood composition is infused into a subject in need thereof at the point of injury, such as for example a soldier in the battlefield.

In another aspect, the present disclosure provides a kit for preparing a pathogen-inactivated whole blood composition, comprising: (a) a vascular access device (e.g., needle) for drawing whole blood from a donor (e.g., by venipuncture), (b) a first container suitable for mixing (e.g., combining, adding) the whole blood and a pathogen inactivation compound (PIC), wherein the first container comprises (e.g., includes) at least a first inlet and a first outlet; (c) a first conduit (e.g., tubing, tubing segment(s)) extending between the vascular access device and the first container (e.g., first inlet of the first container), (e.g., and providing a fluid communication path for transferring the whole blood from the donor (e.g., through the vascular access device) into the first container)); and (d) a container containing a pathogen inactivation compound (PIC container). In some embodiments, the vascular access device is a needle for vascular access in a donor (e.g., venipuncture needle). In some embodiments, the vascular access device and first conduit comprise a needle assembly.

In some embodiments, the PIC container is configured to be coupled (e.g., by a fluid communication path (e.g., conduit, tubing)) to the first container (e.g., first inlet of the first container). In some embodiments, the PIC container is configured to be coupled to the first conduit. In some embodiments, the PIC container is coupled by a fluid communication path (e.g., conduit, tubing) to the first container. In some embodiments, the first container further comprises a second inlet. In some embodiments, the first container further comprises a second inlet and the PIC container is configured to be coupled (e.g., by a fluid communication path) to the second inlet of the first container. In some embodiments, the PIC container is coupled (e.g., by a fluid communication path (e.g., conduit, tubing)) to the second inlet of the first container. In some embodiments, the kit further comprises a second PIC container. In some embodiments, the second PIC container is suitable for storage of a PIC (e.g., lyophilized PIC). In some embodiments, the second PIC container is suitable for reconstitution of a lyophilized PIC. In some embodiments, the PIC container coupled or configured to be coupled to the first container of a kit is suitable for storage of a PIC. In some embodiments, the PIC container coupled or configured to be coupled to the first container of a kit is suitable for reconstitution of a lyophilized PIC. In some embodiments, the second PIC container is suitable for transferring a PIC to the PIC container coupled or configured to be coupled to the first container of a kit provided herein. In some embodiments, the second PIC container is suitable for transferring a PIC to a conduit coupled or configured to be coupled to the first container of a kit provided herein. In some embodiments, the kit further comprises a container containing a quencher (quencher container). In some embodiments, the quencher container is configured to be coupled (e.g., by a fluid communication path) to the first container (e.g., first inlet of the first container). In some embodiments, the quencher container is configured to be coupled to the first conduit. In some embodiments, the quencher container is coupled by a fluid communication path (e.g., conduit, tubing) to the first container. In some embodiments, the quencher container is configured to be coupled (e.g., by a fluid communication path) to the second inlet of the first container. In some embodiments, the quencher container is coupled (e.g., by a fluid communication path (e.g., conduit, tubing)) to the second inlet of the first container. In some embodiments, the kit further comprises a second quencher container. In some embodiments, the second quencher container is suitable for storage of a quencher (e.g., lyophilized quencher). In some embodiments, the second quencher container is suitable for reconstitution of a lyophilized quencher. In some embodiments, the quencher container coupled or configured to be coupled to the first container of a kit is suitable for storage of a quencher. In some embodiments, the quencher container coupled or configured to be coupled to the first container of a kit is suitable for reconstitution of a lyophilized quencher. In some embodiments, the second PIC container is suitable for transferring a quencher to the quencher container coupled or configured to be coupled to the first container of a kit provided herein. In some embodiments, the second quencher container is suitable for transferring a quencher to a conduit coupled or configured to be coupled to the first container of a kit provided herein. In some embodiments, the PIC container and the quencher container are the same container (e.g., portions of the same container, separate chambers of the same container). In some embodiments, the PIC container and the quencher container are separate chambers within the same container.

In some embodiments, the kit further comprises a second conduit wherein the second conduit comprises at one end at least one adaptor for coupling a PIC container and/or a quencher container to the second conduit. In some embodiments, the kit further comprises a second conduit wherein the second conduit comprises at one end at least one adaptor for coupling a PIC container to the second conduit. In some embodiments, the kit further comprises a second conduit wherein the second conduit comprises at one end at least one adaptor for coupling a quencher container to the second conduit. In some embodiments, the second conduit comprises at one end a first adaptor for coupling a PIC container to the second conduit and a second adaptor for coupling a quencher container to the second conduit. In some embodiments, the kit further comprises a second conduit, wherein the second conduit is coupled at one end to a PIC container and/or a quencher container. In some embodiments, the second conduit is configured to be coupled to the first container, (e.g., providing a fluid communication path between the PIC container and/or quencher container and the first container). In some embodiments, the second conduit is configured to be coupled to the first inlet of the first container. In some embodiments, the second conduit is configured to be coupled to the second inlet of the first container. In some embodiments, the second conduit is coupled to the first container, (e.g., providing a fluid communication path between the PIC container and/or quencher container and the first container). In some embodiments, the second conduit is coupled to the first inlet of the first container. In some embodiments, the second conduit is coupled to the second inlet of the first container. In some embodiments, the second conduit is configured to be coupled to the first conduit, (e.g., providing a fluid communication path between the PIC container and/or quencher container and the first container). In some embodiments, the fluid communication path is an openable fluid communication path.

In some embodiments, the kit further comprises a displacement device (e.g., an air displacement device) suitable for increasing the transfer of the PIC and/or the quencher into the first container (e.g., through the second conduit and into the first container). In some embodiments, the kit further comprises a displacement device suitable for increasing the transfer of the PIC into the first container. In some embodiments, the kit further comprises a displacement device suitable for increasing the transfer of the quencher into the first container. In some embodiments, the kit further comprises a displacement device suitable for increasing the transfer of the PIC and the quencher into the first container. In some embodiments, the displacement device is an air displacement device. In some embodiments, the air displacement device is a sample diversion pouch. In some embodiments, the displacement device (e.g., air displacement device) is coupled to the second conduit. In some embodiments, the first container contains an anticoagulant (e.g., anticoagulant solution).

In some embodiments, the PIC comprises a functional group which is, or which forms, a reactive electrophilic group. In some embodiments, the functional group is selected from the group consisting of a mustard, a mustard intermediate, and a mustard equivalent. In some embodiments, the functional group is, or is capable of forming, an aziridinium ion. In some embodiments, the reactive electrophilic group is capable of reacting with nucleic acids. In some embodiments, the PIC comprises a nucleic acid binding ligand. In some embodiments, the nucleic acid binding ligand is an intercalator. In some embodiments, the intercalator is an acridine. In some embodiments, the PIC comprises a frangible linker linking the functional group and the nucleic acid binding ligand. In some embodiments, the PIC is β-alanine, N-(acridin-9-yl), 2-[bis(2-chloroethyl)amino] ethyl ester.

In some embodiments, the quencher comprises a thiol group, wherein the thiol is capable of reacting with a reactive electrophilic group of the pathogen inactivation compound. In some embodiments, the quencher comprises cysteine or a derivative of cysteine. In some embodiments, the quencher is glutathione or a pharmaceutically acceptable salt thereof. In some embodiments, the quencher is glutathione monosodium salt.

In some embodiments, the kit further comprises a second container suitable for storing a pathogen-inactivated whole blood composition. In some embodiments, the kit further comprises a second container suitable for storing a pathogen-inactivated whole blood composition, wherein the second container comprises (e.g., includes) at least a first inlet and a first outlet. In some embodiment, the second container is coupled to the first container. In some embodiments, the kit further comprises a third conduit extending between the first container (e.g., first outlet of the first container) and the second container (e.g., first inlet of the second container) (e.g., and providing a fluid communication path for transferring (e.g., under sterile conditions) a mixture comprising a whole blood composition and a PIC (e.g., pathogen inactivated whole blood composition) from the first container into the second container). In some embodiments, the kit further comprises a third container suitable for storing a pathogen-inactivated whole blood composition. In some embodiments, the kit further comprises a third container suitable for storing a pathogen-inactivated whole blood composition, wherein the third container comprises (e.g., includes) at least a first inlet and a first outlet, and a fourth conduit extending between the second container (e.g., the first outlet of the second container) and the third container (e.g., first inlet of the third container) and providing a fluid communication path for transferring (e.g., under sterile conditions) a mixture comprising a whole blood composition and a PIC (e.g., pathogen inactivated whole blood composition) from the second container into the third container. In some embodiments, the fluid communication path is an openable fluid communication path.

In some embodiments, the kit further comprises an infusion line assembly for infusing the pathogen-inactivated whole blood composition into a subject (e.g., administering the pathogen-inactivated whole blood). In some embodiments, the infusion line assembly is configured to be coupled (e.g., by way of a spike port) to a first container, a second container or a third container. In some embodiments, the kit further comprises an infusion line assembly for infusing the pathogen-inactivated whole blood composition into a subject, wherein the infusion line assembly comprises a second vascular access device (e.g., needle, infusion needle) and an infusion line conduit extending between the first container, the second container or the third container (e.g., outlet of the first container, second container or third container) and the second vascular access device, (e.g., wherein the infusion line conduit provides a fluid communication path for sterilely transferring the pathogen-inactivated whole blood composition from the container (e.g., first container, second container, third container) to the vascular access device). In some embodiments, the kit further comprises an infusion line assembly for infusing the pathogen-inactivated whole blood composition into a subject, wherein the infusion line assembly comprises a second vascular access device and an infusion line conduit extending between the first outlet of the second container and the second vascular access device, (e.g., wherein the infusion line conduit provides a fluid communication path for sterilely transferring the pathogen-inactivated whole blood composition from the second container to the vascular access device). In some embodiments, the infusion line assembly comprises a filter.

In some embodiments, the first container (e.g., container sheeting material) comprises a polyvinyl chloride (e.g., plasticized polyvinyl chloride). In some embodiments, the first container comprises a polyethylene (e.g., ethylene vinyl acetate, ethylene vinyl acetate copolymer). In some embodiments, the first container comprises a polyolefin (e.g., polyolefin blend). In some embodiments, the second container (e.g., container sheeting material) comprises a polyvinyl chloride (e.g., plasticized polyvinyl chloride). In some embodiments, the second container comprises a polyethylene (e.g., ethylene vinyl acetate, ethylene vinyl acetate copolymer). In some embodiments, the second container comprises a polyolefin (e.g., polyolefin blend). In some embodiments, the first container and/or the second container does not comprise di-ethylhexyl phthalate.

In another aspect, the present disclosure provides a kit for preparing a pathogen-inactivated whole blood composition, comprising: (a) a first container suitable for mixing (e.g., combining, adding) a whole blood composition, a pathogen inactivation compound (PIC) and a quencher, wherein the first container comprises (e.g., includes) at least a first inlet and a first outlet, (b) a second container suitable for storing a pathogen-inactivated whole blood composition, wherein the second container comprises (e.g., includes) at least a first inlet and a first outlet, and wherein the second container is coupled to the first container; (c) a container containing a pathogen inactivation compound (PIC container), (d) a container containing a quencher (quencher container), (e) a first conduit, wherein the first conduit at one end is coupled to or configured to be coupled to a PIC container and a quencher container, and wherein the first conduit further comprises a displacement device (e.g., an air displacement device) suitable for increasing the transfer of the PIC and the quencher into the first container (e.g., through the first conduit and into the first container). In some embodiments, the first outlet of the first container is coupled to the first inlet of the second container. In some embodiments, the first container is coupled to the second container by a second conduit (e.g., tubing) providing a fluid communication path for transferring the whole blood composition (e.g., pathogen-inactivated whole blood composition) from the first container to the second container. In some embodiments, the present disclosure provides a kit for preparing a pathogen-inactivated whole blood composition, comprising: (a) a first container suitable for mixing (e.g., combining, adding) a whole blood composition, a pathogen inactivation compound (PIC) and a quencher, wherein the first container comprises (e.g., includes) at least a first inlet and a first outlet, (b) a second container suitable for storing a pathogen-inactivated whole blood composition, wherein the second container comprises (e.g., includes) at least a first inlet and a first outlet, (c) a container containing a pathogen inactivation compound (PIC container), (d) a container containing a quencher (quencher container), (e) a first conduit, wherein the first conduit at one end is coupled to or configured to be coupled to a PIC container and a quencher container, and wherein the first conduit further comprises a displacement device (e.g., an air displacement device) suitable for increasing the transfer of the PIC and the quencher into the first container (e.g., through the first conduit and into the first container); and (f) a second conduit extending between the first container and the second container (e.g., and providing a fluid communication path for transferring the whole blood composition (e.g., pathogen-inactivated whole blood composition) from the first container to the second container). In some embodiments, the first conduit provides a fluid communication path from the PIC contain and the quencher container. In some embodiments, the fluid communication path is an openable fluid communication path. In some embodiments, the first container further comprises (e.g., includes) a second inlet.

In some embodiments, the first conduit further comprises at least one adaptor for coupling the first conduit to a PIC container and a quencher container. In some embodiments, the first conduit comprises a first adaptor for coupling a PIC container to the first conduit and a second adaptor for coupling a quencher container to the first conduit. In some embodiments, the first conduit is coupled to a PIC container and a quencher container. In some embodiments, the PIC container and the quencher container are the same container. In some embodiments, the first conduit is coupled or configured to be coupled to the first container, providing a fluid communication path between the PIC container and quencher container and the first container. In some embodiments, the first conduit is coupled or configured to be coupled to an inlet (e.g., first inlet, second inlet) of the first container. In some embodiments, the kit further comprises a vascular access device (e.g., needle) for drawing whole blood from a donor (e.g., by venipuncture). In some embodiments, the kit further comprises a vascular access device for drawing whole blood from a donor and third conduit extending between (e.g., connecting) the vascular access device and the first container (e.g., first inlet of the first container) and providing a fluid communication path for transferring the whole blood from the donor (e.g., from the vascular access device, through the vascular access device) into the first container.

In some embodiments, the PIC container is configured to be coupled (e.g., by a fluid communication path (e.g., conduit, tubing)) to the first conduit. In some embodiments, the PIC container is configured to be coupled to the first conduit. In some embodiments, the PIC container is coupled by a fluid communication path to the first conduit. In some embodiments, the kit further comprises a second PIC container. In some embodiments, the second PIC container is suitable for storage of a PIC (e.g., lyophilized PIC). In some embodiments, the second PIC container is suitable for reconstitution of a lyophilized PIC. In some embodiments, the PIC container coupled or configured to be coupled to the first conduit is suitable for storage of a PIC. In some embodiments, the PIC container coupled or configured to be coupled to the first conduit is suitable for reconstitution of a lyophilized PIC. In some embodiments, the second PIC container is suitable for transferring a PIC to the PIC container coupled or configured to be coupled to the first conduit. In some embodiments, the second PIC container is suitable for transferring a PIC to a conduit coupled or configured to be coupled to the first container of a kit provided herein. In some embodiments, the kit further comprises a container containing a quencher (quencher container). In some embodiments, the quencher container is configured to be coupled (e.g., by a fluid communication path (e.g., conduit, tubing)) to the first conduit. In some embodiments, the quencher container is configured to be coupled to the first conduit. In some embodiments, the quencher container is coupled by a fluid communication path to the first conduit. In some embodiments, the kit further comprises a second quencher container. In some embodiments, the second quencher container is suitable for storage of a quencher (e.g., lyophilized quencher). In some embodiments, the second quencher container is suitable for reconstitution of a lyophilized quencher. In some embodiments, the quencher container coupled or configured to be coupled to the first conduit is suitable for storage of a quencher. In some embodiments, the quencher container coupled or configured to be coupled to the first conduit is suitable for reconstitution of a lyophilized quencher. In some embodiments, the second PIC container is suitable for transferring a quencher to the quencher container coupled or configured to be coupled to the first conduit. In some embodiments, the second quencher container is suitable for transferring a quencher to a conduit coupled or configured to be coupled to the first container of a kit provided herein. In some embodiments, the PIC container and the quencher container are the same container (e.g., portions of the same container, separate chambers of the same container). In some embodiments, the PIC container and the quencher container are separate chambers within the same container.

In some embodiments, the first container further comprises (e.g., includes) a second inlet, wherein the first conduit is configured to be coupled to the second inlet of the first container. In some embodiments, the first container further comprises (e.g., includes) a second inlet and the first conduit is coupled to the second inlet of the first container. In some embodiments, the first conduit provides fluid communication path from the PIC container and the quencher container to the first container. In some embodiments, the first conduit is configured to be coupled to the third conduit, providing a fluid communication path between the PIC container and quencher container and the first container. In some embodiments, the fluid communication path is an openable fluid communication path. In some embodiments, the first container contains an anticoagulant.

In some embodiments, the PIC comprises a functional group which is, or which forms, a reactive electrophilic group. In some embodiments, the functional group is selected from the group consisting of a mustard, a mustard intermediate, and a mustard equivalent. In some embodiments, the functional group is, or is capable of forming, an aziridinium ion. In some embodiments, the reactive electrophilic group is capable of reacting with nucleic acids. In some embodiments, the PIC comprises a nucleic acid binding ligand. In some embodiments, the nucleic acid binding ligand is an intercalator. In some embodiments, the intercalator is an acridine. In some embodiments, the PIC comprises a frangible linker linking the functional group and the nucleic acid binding ligand. In some embodiments, the PIC is β-alanine, N-(acridin-9-yl), 2-[bis(2-chloroethyl)amino] ethyl ester.

In some embodiments, the quencher comprises a thiol group, wherein the thiol is capable of reacting with a reactive electrophilic group of the pathogen inactivation compound. In some embodiments, the quencher comprises cysteine or a derivative of cysteine. In some embodiments, the quencher is glutathione or a pharmaceutically acceptable salt thereof. In some embodiments, the quencher is glutathione monosodium salt.

In some embodiments, the kit comprises a third container suitable for storing a pathogen-inactivated whole blood composition, wherein the third container comprises (e.g., includes) at a first inlet and a first outlet, and wherein the third container is coupled to the second container. In some embodiments, the kit comprises a third container suitable for storing a pathogen-inactivated whole blood composition, wherein the third container comprises (e.g., includes) at a first inlet and a first outlet, and wherein the kit further comprises a fourth conduit extending between the second container (e.g., first outlet of the second container) and the third container (e.g., first inlet of the third container) (e.g., and providing a fluid communication path for transferring (e.g., under sterile conditions) the whole blood composition (e.g., pathogen-inactivated whole blood composition) from the second container into the third container). In some embodiments, the fluid communication path is an openable fluid communication path. In some embodiments, the kit further comprises an infusion line assembly for infusing the pathogen-inactivated whole blood composition into a subject (e.g., administering the pathogen-inactivated whole blood). In some embodiments, the infusion line assembly is configured to be coupled (e.g., by way of spike port) to a second container or a third container. In some embodiments, the kit further comprises an infusion line assembly for infusing the pathogen-inactivated whole blood composition into a subject, wherein the infusion line assembly is coupled to the second container. In some embodiments, the kit further comprises an infusion line assembly for infusing the pathogen-inactivated whole blood composition into a subject, wherein the infusion line assembly is coupled to the third container. In some embodiments, the kit further comprises an infusion line assembly for infusing the pathogen-inactivated whole blood composition into a subject, wherein the infusion line assembly comprises a second vascular access device (e.g., needle, infusion needle) and an infusion line conduit extending between second container or the third container (e.g., outlet of the first container, second container or third container) and the second vascular access device, (e.g., wherein the infusion line conduit provides a fluid communication path for sterilely transferring the pathogen-inactivated whole blood composition from the container (e.g., second container, third container) to the vascular access device). In some embodiments, the kit further comprises an infusion line assembly for infusing the pathogen-inactivated whole blood composition into a subject, wherein the infusion line assembly comprises a second vascular access device and an infusion line conduit extending between the first outlet (e.g., spike port) of the second container and the second vascular access device, (e.g., wherein the infusion line conduit provides a fluid communication path for sterilely transferring the pathogen-inactivated whole blood composition from the second container to the vascular access device). In some embodiments, the infusion line assembly comprises a filter.

In some embodiments, the first container (e.g., container sheeting material) comprises a polyvinyl chloride (e.g., plasticized polyvinyl chloride). In some embodiments, the first container comprises a polyethylene (e.g., ethylene vinyl acetate, ethylene vinyl acetate copolymer). In some embodiments, the first container comprises a polyolefin (e.g., polyolefin blend). In some embodiments, the second container (e.g., container sheeting material) comprises a polyvinyl chloride (e.g., plasticized polyvinyl chloride). In some embodiments, the second container comprises a polyethylene (e.g., ethylene vinyl acetate, ethylene vinyl acetate copolymer). In some embodiments, the second container comprises a polyolefin (e.g., polyolefin blend). In some embodiments, the first container and/or the second container does not comprise di-ethylhexyl phthalate.

It is to be understood that one, some, or all of the properties of the various embodiments described herein may be combined to form other embodiments. These and other aspects will become apparent to one of skill in the art. These and other embodiments are further described by the detailed description that follows.

DETAILED DESCRIPTION

Figure 1A:
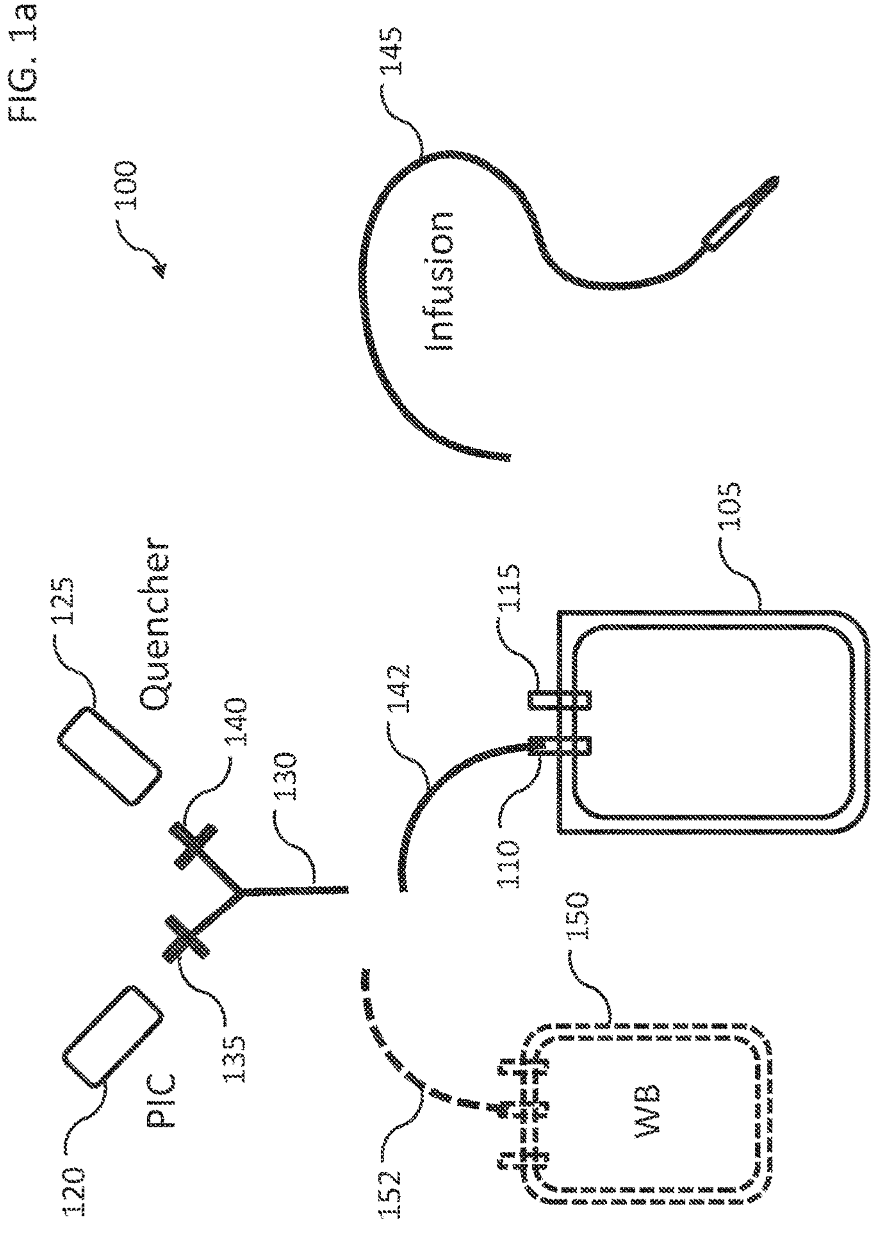
FIG. 1*a* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

The present disclosure provides, in some aspects, improved methods and kits for preparing pathogen inactivated whole blood and other blood product compositions, including pathogen inactivated whole blood and other blood product compositions suitable for infusion. The kits and related methods of using such kits disclosed herein have been found to provide improved pathogen inactivation processes, including for example, processes that yield pathogen inactivated whole blood and other blood product compositions with decreased residual levels of pathogen inactivation compound in the composition, which may be particularly beneficial for subsequent infusion of the whole blood compositions. The improved kits and related methods also provide a new opportunity for preparing pathogen inactivated whole blood compositions under conditions where access to suitable facilities and/or power sources may not be readily available, such as in war zones.

The terms “pathogen inactivation” and “pathogen inactivation process” means a process useful to inactivate pathogens that may be present in a whole blood composition, such as a whole blood donation, where it is understood that the process does not necessarily inactivate completely all pathogens that may be present, but substantially reduces the amount of pathogens to significantly reduce the risk of a transfusion associated disease (e.g., transfusion transmitted infection, TTI). The inactivation of a pathogen may be assayed by measuring the number of infective pathogens (e.g., viral particles, bacteria) in a certain volume, before and after a pathogen inactivation process, and the level of inactivation is typically represented in the log reduction in the infectivity of the pathogen, or log reduction in titer. Methods of assaying log reduction in titer, and measurements thereof for pathogen inactivation are known in the art. When the inactivation process is tested against a variety of pathogens, the reduction in a particular active pathogen is at least about 1 log, at least about 2 log, at least about 3 log, at least about 4 log, or at least about 5 log reduction in titer. A variety of pathogen inactivation processes are known in the art and methods for demonstrating levels of pathogen activation using various commercially available pathogen inactivation processes, such as the INTERCEPT® Blood System (Cerus Corp), are known in the art. In certain embodiments, a pathogen inactivation process may comprise treating with a pathogen inactivation compound.

The term “suitable for infusion” refers to a whole blood composition (e.g., pathogen-inactivated whole blood composition) or other blood product (e.g., blood product prepared from a whole blood composition) able to be used for an infusion (e.g., transfusion) into a subject (e.g., a human patient) according to medical judgement. Non-limiting examples of other blood products include a red blood cell composition, plasma composition, platelet composition, cryoprecipitate composition and cryo-reduced plasma composition. In some embodiments, suitability refers to having sufficient biological activity for its intended use, i.e., for use where an infusion of whole blood or other blood product is indicated, including, without limitation, prophylactic and therapeutic infusion. In some embodiments, suitability refers to having sufficient safety, such as for example, meeting applicable regulatory and/or accreditation requirements for safety of administering the treated whole blood or blood product composition. In some embodiments, suitability refers to a pathogen-inactivated whole blood composition or other blood product having a concentration (e.g., residual concentration) of a pathogen inactivation compound and/or byproduct(s) thereof lower than a certain criteria (e.g., lower than a maximum acceptable concentration). In some embodiments, suitability refers to meeting one or more standards (e.g., having suitable characteristics, having a level of a biological activity or function, having at least a minimum dose) established by an accrediting agency or regulatory body that governs infusion practices, such as for example the AABB.

Pathogen Inactivation Compounds

The term “pathogen inactivation compound” or “pathogen inactivating compound” means any suitable compound that can be used to inactivate a pathogen that may be present in a whole blood composition. The inactivation of a pathogen in the whole blood compositions is effected by contacting the pathogen in the whole blood composition with a pathogen inactivation compound (PIC). In any of the embodiments described herein, the PIC (e.g., amustaline, S-303 described herein) may be present in an effective amount (e.g., an effective amount to inactivate a pathogen, such as an amount sufficient to inactivate, for example, at least about 1 log, at least about 2 log, at least about 3 log, at least about 4 log, at least about 5 log, or at least about 6 log or more of a pathogen in the whole blood composition, if present). Pathogen inactivation compounds that may be used by the methods of the disclosure include for example, compounds that comprise a functional group which is, or which is capable of forming and has formed, e.g. in situ, a reactive group, such as an electrophilic group. In some embodiments, the PICs of the present disclosure do not require photoactivation to be reactive. For example, the functional group may be a mustard group, a mustard group intermediate, a mustard group equivalent, an epoxide, a formaldehyde or a formaldehyde synthon. Such functional groups are capable of forming in situ a reactive group, such as an electrophilic aziridine, aziridinium, thiirane or thiiranium ion. A mustard group may be a mono- or bis-(haloethyl)amine group or a mono (haloethyl)sulfide group. A mustard equivalent is a group that reacts by a mechanism similar to the mustards, for example by forming reactive intermediates such as aziridinium and aziridine groups or thiirane and thiiranium groups. Examples include aziridine derivatives, mono or bis-(mesylethyl)amine groups, mono-(mesylethyl)sulfide groups, mono or bis-(tosylethyl)amine groups and mono-(tosylethyl)sulfide groups. A formaldehyde synthon is any compound that breaks down to a formaldehyde, which includes a hydroxylamine such as hydroxymethylglycine. The reactive group of the PIC is capable of reacting with the nucleic acids of pathogens, for example with nucleophilic groups on the nucleic acid. The reactive group is also capable of reacting with a nucleophilic group of a quencher. PICs may also include a component that targets the compound to nucleic acids, such as an anchor portion. The anchor portion comprises a moiety which is capable of binding non-covalently to a nucleic acid biopolymer, such as DNA or RNA, and is also referred to as a nucleic acid binding ligand, nucleic acid binding group, or nucleic acid binding moiety. Examples of such compounds are described in U.S. Pat. Nos. 5,691,132, 6,410,219, 6,136,586, 6,617,157, and 6,709,810, each of which is incorporated by reference herein. Another class of PICs that may be used in the methods of the present disclosure comprises the above-mentioned reactive groups linked to a nucleic acid binding group via a hydrolysable linker, such as described in U.S. Pat. No. 6,514,987, incorporated by reference herein. The anchor portion of the PICs has an affinity for nucleic acids. This affinity may be due to any of several modes of binding to the nucleic acid non-covalently, including, but not limited to, intercalation, minor groove binding, major groove binding, and electrostatic binding (e.g., phosphate backbone binding). The affinity may also be due to mixed modes of binding (e.g., intercalation and minor groove binding). The binding may be sequence-specific (i.e., increased binding affinity for one or more particular nucleic acid sequences over other nucleic acid sequences) or nonsequence-specific. Detailed examples of such nucleic acid binding moieties can be found in the above-mentioned patents.

In some embodiments of each of the methods, kits and compositions described herein, the PIC may comprise a functional group which is, or which forms, a reactive electrophilic group reactive with the nucleophile of the chosen quencher. In some embodiments, the pathogen-inactivating group comprises a nucleic acid binding ligand and a functional group which is, or which forms an electrophilic group. A specific example of a suitable PIC for use in the present disclosure is β-alanine, N-(acridin-9-yl), 2-[bis(2-chloroethyeamino]ethyl ester (also alternatively referred to herein as "S-303" or "amustaline"), the structure of which is as follows, including salts thereof.

S-303

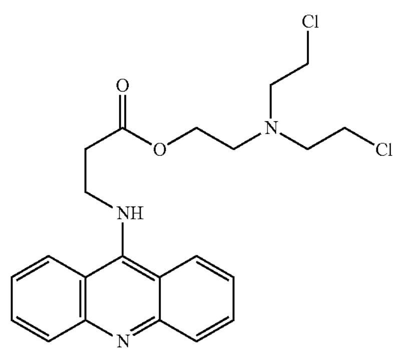

Quenchers

Quenchers for use in methods of the present disclosure are intended to reduce unwanted side-reactions of the reactive electrophilic species used to inactivate pathogens (e.g., binding of the pathogen inactivation compound to RBC surfaces in the whole blood composition which may lead to an undesired immune response). In any of the embodiments described herein, the quencher (e.g., glutathione) may be present in an effective amount (for example, an effective amount to reduce unwanted side reactions, such as the amounts described herein). Suitable quenchers may comprise a nucleophilic group that is capable of reacting with the electrophilic group of the PIC. Non-limiting examples are described in detail in U.S. Pat. No. 6,709,810, incorporated by reference herein in its entirety. In some embodiments, the quenchers are capable of significantly reducing the unwanted side reactions in a whole blood composition while allowing the PIC to sufficiently inactivate a pathogen that may be contaminating the whole blood composition. In some embodiments, the methods of the present disclosure provide an effective amount of quencher in combination with an effective amount of PIC under conditions which provide optimal reduction in unwanted side reactions (e.g., binding of the PIC) combined with sufficient inactivation of pathogens, without significantly altering properties of the whole blood composition or blood components of the whole blood (e.g., without decreasing red blood cell osmotic fragility, without significantly increasing red blood cell dehydration, without significantly decreasing coagulation factor levels required for hemostasis, without significantly decreasing one or more platelet functions). A variety of unwanted side reactions may be reduced, such as reaction of the PIC with proteins and/or red blood cells in the whole blood composition. In some embodiments, the quencher provides optimal reduction in the modification of whole blood compositions or blood components therein, such as the binding of IgG to red blood cells or binding of the PIC to red blood cells. While the methods of the present disclosure involve the ex vivo treatment (e.g., pathogen inactivation) of whole blood compositions, some quenchers may remain in the composition upon introduction into an individual. As such, in some embodiments, the quenchers of the disclosure are suitable for infusion. Suitable quenchers include, but are not limited to, compounds comprising a thiol group, such as quenchers comprising the amino acid cysteine or a suitable derivative of cysteine, such as N-acetyl cysteine. Examples of such quenchers include cysteine and peptides comprising at least one cysteine, such as glutathione. In some embodiments, the suitable quenchers comprise a derivative of cysteine that can form a thiol group in situ, with or without the use of additional chemicals or added enzymes, such as S-acetyl cysteine or other suitable thiol derived prodrugs of cysteine, or peptides comprising S-acetyl cysteine or other suitable thiol derived prodrugs of cysteine. Suitable derivatives of cysteine are those which either comprise, or are capable of forming in situ, a cysteinyl thiol which is capable of reacting with the electrophilic group of the PIC.

In some embodiments, the quencher is a peptide of 2 to 10 amino acids, wherein at least one of the amino acids is cysteine, N-acetyl cysteine, S-acetyl cysteine, or other suitable derivative of cysteine. In some embodiments, the quencher is a peptide of at least 3 amino acids, such as about 3-10 amino acids, also about 3-6 amino acids, wherein at least one of the amino acids is cysteine, N-acetyl cysteine, S-acetyl cysteine, or other suitable derivative of cysteine. In some embodiments, the quencher is a peptide of at least 3 amino acids, such as about 3-10 amino acids, also about 3-6 amino acids, wherein at least one of the amino acids is cysteine, N-acetyl cysteine, S-acetyl cysteine, or other suitable derivative of cysteine, also wherein at least 2 or at least 3 of the amino acids is cysteine, N-acetyl cysteine, S-acetyl cysteine, or other suitable derivative of cysteine.

In a preferred embodiment, the quencher is neutralized glutathione (also known as L-glutathione and γ-L-glutamyl-L-cysteinyl-glycine). Glutathione has many properties that make it particularly useful as a quencher. It is normally present in all cell types. It is not believed to be able to passively penetrate into a pathogen, such as by passing through cell membranes or lipid coats, of bacteria and lipid-enveloped viruses, or by passing through the viral capsid of non-enveloped viruses. At approximately neutral pH glutathione is charged and in the absence of active transport, does not penetrate lipid bilayers to any significant extent. This is consistent with inactivation of lipid enveloped viruses such as HIV and VSV being substantially unaffected by glutathione, including using concentrations of neutralized glutathione greater than 2 mM. The use of glutathione does have some effect on inactivation of e.g., *Yersinia enterocolitica, Staphylococcus epidermidis* and *Serratia marcescens*. However, this can be managed by using effective amounts of neutralized glutathione and PIC. As such, preferred methods of quenching are provided wherein contamination of a whole blood composition by a viral or bacterial pathogen is inactivated by at least about 2 log, by at least about 3 log, by at least about 4 log, by at least about 5 log or by at least 6 log or more. At the appropriate conditions, as described by the present disclosure, glutathione is also compatible with in vitro storage of whole blood and the resulting pathogen inactivated whole blood composition is suitable for introduction in vivo.

In some embodiments, the quencher is glutathione in its reduced form. Glutathione disulfide, the oxidized form of glutathione, may also be used, so long as the glutathione disulfide is sufficiently reduced in solution prior to addition of the solution to the mixture comprising the whole blood composition or sufficiently reduced after addition to the mixture comprising the whole blood composition.

In some embodiments, the quencher is a derivative of glutathione, such as a glutathione monoalkyl ester or dialkyl ester, wherein the alkyl group is a straight or branched group having 1 to 10 carbon atoms. Specific examples of alkyl groups include, but are not limited to methyl group, ethyl group, propyl group, isopropyl group, butyl group, isobutyl group, tert-butyl group, pentyl group, isopentyl group, neopentyl group, tert-pentyl group, 1-methylbutyl group, hexyl group, isohexyl group, 2-methylpentyl group, 1-ethylbutyl group, heptyl group, octyl group, nonyl group, and decyl group. For instance, non-limiting examples of glutathione derivatives include glutathione methyl ester, glutathione monoethyl ester, and glutathione monoisopropyl ester. In some embodiments, glutathione oxidized diethyl ester (GSSG-(glycyl)-diethyl-ester) is used. In some embodiments, a thioester of glutathione is hydrolyzed after addition to the whole blood compositions to form the thiol.

It is understood that in some embodiments, the quencher will be provided in the form of a free acid or base, whereas, in other embodiments, the quencher will be provided in the form of a salt. If the quencher is in the form of a salt, the salt is preferably a pharmaceutically acceptable salt. The pharmaceutically-acceptable salts of compounds (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-napthalenesulfonate, nicotinate, oxalate, pamoate, pectinate, persulfate, 3-phenylpropionate, phosphate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, didbutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

For example, in some embodiments, the quencher is in the form of a pharmaceutically acceptable salt formed from glutathione. In some embodiments, the quencher is in the form of a pharmaceutically acceptable salt formed from glutathione and one or more cations such as sodium, aluminum, calcium, lithium, magnesium, zinc, or tetramethylammonium. In some embodiments, the quencher is glutathione (reduced) and is provided in the form of glutathione monosodium salt (available, e.g., from Biomedica Foscama, Italy). In some other embodiments, the glutathione (reduced) is provided in the form of glutathione hydrochloride salt. In some other embodiments, the glutathione is provided in the form of a glutathione (reduced) disodium salt. In further embodiments, a glutathione monoalkyl ester sulfate is used. In some embodiments, glutathione is provided in the form of glutathione oxidized disodium salt.

Base

In some embodiments, methods of the present disclosure further comprise providing a suitable base, such as for example by mixing (e.g., combining) the base (e.g., step (a)) with the whole blood composition, the PIC and a quencher. In some embodiment, the base is of sufficient amount to reduce the level of an unwanted reaction of the PIC with red blood cells in the mixture, relative to the mixture without the base. In some embodiments, the unwanted reaction of the PIC with red blood cells (RBCs) is modification of the surface of the red blood cells by the PIC (see e.g., U.S. Pat. No. 8,900,805). In some embodiments, step (a) further comprises mixing a suitable base with the whole blood composition, the PIC and a quencher, and the base is of sufficient amount to reduce the level of anti-pathogen inactivation compound antibody binding to the RBCs in the treated whole blood composition in the resulting mixture by at least about 5% (or at least about 10%, at least about 25%, at least about 50%, at least about 75%, or at least about 90%) relative to the mixture without the base. In some embodiments, the base and the quencher are mixed with the whole blood composition prior to, at the same time, or no more than about 30 minutes after mixing the PIC with the whole blood composition. In some embodiments, the base and the quencher are mixed together prior to mixing either the base or the quencher with the whole blood composition. In some embodiments, the base is NaOH. In some embodiments, the base is a basic buffer. In some embodiments, the base comprises about 0.5 to 1.5 equivalents of base, where an equivalent means a molar amount that is equivalent to the molar amount of quencher in the mixture. In some embodiments, the base comprises about 0.75 to 1.25 equivalents of base. In some embodiments, the base comprises about 1 equivalent of base. In some embodiments, the resulting mixture of step (a) has a pH at 37° C. of about 6.0 to 7.5. In some embodiments, the pH is about 6.5 to 7.1. In some embodiments, the pH is about 6.8 or 6.9.

In some embodiments, upon mixing (e.g., combining) the PIC and quencher with the whole blood composition, the pH of the mixture is at suitable level to reduce unwanted side reactions of the PIC (e.g., binding of the PIC to RBC surfaces which may lead to an undesired immune response) and sufficiently reduce cell dehydration of RBC during pathogen inactivation of the whole blood. In some embodiments, the unwanted side reaction is modification of the surface of the RBCs by the PIC. In some embodiments, the modification is covalent binding of the PIC to the surface of the RBCs. In other embodiments, the modification is non-covalent binding of the PIC to the surface of the RBCs.

As described herein, in some embodiments of each of the methods, an undesired (also referred to herein as "unwanted") side reaction of the PIC with the RBCs in whole blood is reduced. In some embodiments, the undesired side reaction that is reduced is modification of the RBC surface by the PIC. In some embodiments, the level of side reaction is reduced by at least about 5%, at least about 10%, at least about 25%, at least about 50%, at least about 75%, or at least about 90%. The decrease in the side reaction may be evidenced, for example, by measuring the amount of binding to the treated RBCs of antibodies specific to the PIC and/or measuring the life span of the treated RBCs of the whole blood in vivo, and comparing these measurements to RBCs treated by a second, different method (for example, a method without sufficient quencher and/or base added to the reaction mixture, a method in which no quencher and/or base is added to the reaction mixture, and/or a treatment at a lower pH).

In some embodiments, upon mixing (e.g., combining) the PIC and quencher with the whole blood composition, the pH of the mixture is in the range of about 6.0 to 8.5, about 6.0 to 7.5, about 6.5 to 7.1, about 6.5 to 7.0, about 6.6 to 6.8, or about 6.6, 6.7, 6.8, or 6.9. While the pH in a whole blood composition may change with time, it is desirable that the pH is in a desired range when quencher is added to the whole blood composition, whether or not it already contains PIC. In some embodiments, the methods of the present disclosure involve adding PIC and quencher to a whole blood composition. The desired pH range is necessary upon the addition of both the PIC and quencher, regardless of the order of addition of the PIC and/or quencher to the whole blood composition. In other words, once all three components have been mixed, the pH is within the desired range. In some embodiments, quencher is added prior to PIC. In some embodiments, PIC is added prior to quencher. In some embodiments, quencher and PIC are added essentially simultaneously. Thus, upon addition of PIC and quencher means at the point when both of the quencher and PIC have been mixed with the whole blood composition. The desired pH can be achieved by several means, and is not limited as to when the pH of the whole blood composition is adjusted, or in some embodiments, is not significantly adjusted from the natural pH of the blood product. For example, the desired pH of the whole blood composition can be achieved by adjusting the pH. The pH adjustment may be done, for example, by addition of a suitable solution, such as a buffering solution, prior to adding the PIC and quencher. Alternatively, the pH of the red blood cell composition can be adjusted simultaneously with the addition of either the PIC, the quencher, or both. In some embodiments, the pH is adjusted simultaneously with addition of the quencher. In some embodiments, the quencher is neutralized, such that addition of the neutralized quencher provides the desired pH range in the whole blood composition. As an example, the neutralization of glutathione can be used to effect the necessary pH adjustments. In some embodiments, an appropriate level of neutralization of the glutathione can be used, for example by addition of 1 equivalent of base, to provide a quencher that, upon addition to a whole blood composition, will provide the necessary pH adjustment of the composition. The appropriate neutralization will depend upon the quencher used. For example, when a peptide is used it may depend on the amino acid components of the peptide. In some embodiments, a quencher can be used that does not significantly affect the pH of the red blood cell composition. For example, use of a peptide comprising a cysteine that may further comprise one or more amino acids that result in a more neutral pH for a solution of the naturally isolated peptide. In some embodiments, the peptide further comprises at least one basic amino acid, such as arginine or lysine.

In some embodiments of the methods described herein, where a base is mixed with the whole blood composition along with the PIC and quencher to increase the pH of the mixture to a desired level and/or to improve quenching of undesired side reactions, the base is a basic salt. The basic salt may first be dissolved in an aqueous solution prior to mixing (e.g., combining) with the whole blood composition. In other embodiments, the salt may be added directly to the whole blood composition in solid form. In some embodiments, the basic salt comprises the quencher and provides both the quencher and the base to the mixture. In some embodiments, the base used in the method is a strong base, such as NaOH. Typically, a strong base like NaOH will be dissolved first in aqueous solution prior to mixing with the whole blood composition. In some embodiments, the strong base (e.g., in solution or solid form) is mixed with the quencher prior to mixing the quencher with the whole blood composition. In some embodiments, the base is a basic buffer (added in sufficient quantities and having an appropriate pKa to bring the mixture to the desired pH range). If a basic buffer is used, the buffer will, in some embodiments, be a pharmaceutically acceptable buffer. In some embodiments, the buffer will have a titratable proton with a pKa in the range of about 7 to 8. Examples of buffers which can be used as basic buffers include, but are not limited to, N-(2-hydroxyethyl)-piperazine-N'-2-ethanesulfonic acid (HEPES), phosphate buffered saline (PBS), and sodium phosphate buffer. Other suitable basic buffers will be readily identifiable by one of ordinary skill in the art.

In some embodiments of each of the methods and compositions described herein, the pH of the mixture of whole blood, quencher, PIC, and any added base is greater than about 5.5, greater than about 5.7, greater than about 6.0, greater than about 6.3, greater than about 6.5, greater than about 6.7, greater than about 7.0, or greater than about 7.2. In some embodiments of each of the methods and compositions described herein, the pH of the mixture of whole blood, quencher, PIC, and base (if any is added) is in the range of about 6.0 to 8.5, about 6.0 to 7.5, about 6.5 to 7.1, about 6.5 to 7.0, or about 6.6 to 6.8, or about 6.6, 6.7, 6.8, or 6.9. In some embodiments, the indicated pH is the pH at room temperature. In some embodiments, the indicated pH is the pH at 37° C. For example, in some embodiments, the composition comprising the whole blood is treated with the PIC in the presence of the quencher and any added base, wherein the pH of the mixture is in the range of about 6.5 to about 7.0 (or 7.1) at 37° C.

In some embodiments, the pH of the mixture of whole blood, quencher, and the base (if base is added as part of the method) is in the range of about 6.0 to 8.5, about 6.0 to 7.5, about 6.5 to 7.1, about 6.5 to 7.0, or about 6.6 to 6.8, or about 6.5, 6.7, 6.8, or 6.9, prior to mixing (e.g., combining) the PIC with the whole blood composition. In some other embodiments, the pH is achieved at the same time as or within about 1 hour, within about 30 minutes, within about 20 minutes, within about 10 minutes, within about 5 minutes, or within about 2 minutes of mixing the PIC with the composition comprising the whole blood. In some embodiments of those methods where the pH is adjusted, the pH is adjusted to the desired pH range prior to, at the same time as, within about 1 hour, within about 30 minutes, within about 20 minutes, within about 10 minutes, within about 5 minutes, or within about 2 minutes of mixing the PIC with the composition comprising the whole blood. In those embodiments, where the quencher is glutathione and the PIC is amustaline (e.g., S-303), the pH of the mixture comprising the whole blood composition and the quencher is preferably adjusted to the desired pH range (e.g., pH 6.5 to 7.0) prior to mixing the S-303 with the whole blood composition.

In some embodiments, the resulting pH of the composition after mixing (e.g., combining) the whole blood, quencher, and the base, is not necessarily an adjustment of the pH of the starting whole blood composition. For example, a whole blood composition may have a pH in the desired range of 6.0-7.5, and the pH of the composition does not change significantly on addition of quencher, and subsequently PIC. In such embodiments, the quencher either naturally provides the desired pH, or is neutralized accordingly to provide the desired pH. It is the combination of adding high initial amounts of quencher, such as about 5 mM to about 40 mM, with a resulting pH in the desired range that is important. Thus, for peptides, regardless of the peptide quencher, it can be effectively neutralized as needed to provide a suitable pH range when added to a whole blood composition, and further may be selected to provide a suitable amount of buffering in the desired pH range. As such, a neutralized quencher means that the quencher is suitably titrated with acid or base as needed such that on addition to a whole blood composition, the resulting mixture has a pH that provides better quenching of unwanted side reactions (e.g., binding of the PIC to RBC surfaces which may lead to an undesired immune response) while avoiding cell dehydration of the RBCs during inactivation, such as a pH in the range of about 6.0 to 8.5, about 6.0 to 7.5, about 6.5 to 7.0, about 6.5 to 7.1, or about 6.6 to 6.8, or about 6.6, 6.7, 6.8, or 6.9. In some embodiments, the peptide as isolated naturally, is suitably neutralized, i.e. requires no addition of acid or base to provide the desired pH in the final mixture. Further, preferred quenchers will provide buffering capacity to maintain the pH in the desired range for a time necessary to quench unwanted side reactions.

In some embodiments of each of the methods and compositions described herein, the quencher is neutralized. A quencher is said to be "neutralized" by a base, if a sufficient amount of the base has been combined with the quencher, such that the quenching of an undesired side reaction between the PIC and the RBCs of the whole blood is improved in a mixture comprising the composition comprising the whole blood, the PIC, and quencher. A "neutralized quencher" does not necessarily have a neutral pH, nor is it necessarily uncharged. In some embodiments, the neutralized quencher is neither in its most protonated form nor its most deprotonated form. In some embodiments, where the quencher is very acidic, the pH of the neutralized quencher may still be lower than 7.0 (e.g., about 6.6, 6.7, 6.8, or 6.9). In some embodiments, the pH of solution of the neutralized quencher may be greater than 7.0. In some embodiments, the pH of the solution of the neutralized quencher will be detectably higher than that of the quencher prior to addition of the base. In some embodiments, the quencher is neutralized with at least about 0.25 equivalents, at least about 0.5 equivalents, at least about 0.75 equivalents, at least about 1 equivalent, at least about 1.25 equivalents, at least about 1.5 equivalents, or at least about 2 equivalents of a base. In some embodiments, the quencher is neutralized with less than about 2 equivalents, less than about 1.5 equivalents, less than about 1.25 equivalents, less than about 1 equivalent, or less than about 0.75 equivalents of a base. In some embodiments, the quencher is neutralized with about 0.25 to about 2 equivalents, about 0.5 to about 1.5 equivalents, or about 0.75 to about 1.25 equivalents of base. In some embodiments, the quencher is neutralized with about 0.75 equivalent of base. In other embodiments, the quencher is neutralized with about 1 equivalent of base. In other embodiments, the quencher is neutralized with about 1.25 equivalent of base. For example, In some embodiments of the disclosure, glutathione is neutralized with about 1 equivalent of a suitable base, such as sodium hydroxide. In this instance, a solution of the protonated glutathione has a pH of approximately 3, a solution neutralized with 1 equivalent of sodium hydroxide has a pH of approximately 4.5, and a solution neutralized with 2 equivalents of sodium hydroxide has a pH of approximately 9.5. Any appropriate peptide quencher comprising at least one cysteine can be suitably adjusted to provide the desired pH upon addition to the red blood cell composition.

Appropriate methods for neutralizing glutathione and other quenchers will be readily apparent to those of ordinary skill in the art. In some embodiments, sodium hydroxide is used to neutralize or partially neutralize the quencher. In some embodiments, solid pellets of NaOH are first dissolved in water to generate a concentrated solution of the base, such as a 1 N, 5 N, 10 N, or 20 N NaOH solution. In some embodiments, an appropriate amount of that NaOH solution is then added to the quencher either prior to, at the same time as, or following addition of the quencher to the mixture. Alternatively, the NaOH is added to the whole blood composition or the PIC, or the combination of the two, prior to the addition of the quencher to the mixture.

In addition to providing a quencher that is suitably pH-adjusted or neutralized, in some embodiments, preferred quenchers are not able to significantly enter into the pathogens, such that they optimally quench unwanted reactions in the extracellular environment, but do not interfere with pathogen inactivation once the PIC has penetrated inside of the pathogen.

In some embodiments of each of the methods described herein, the quencher is an acidic compound. In some embodiments, the quencher is provided in the free acid form. In some embodiments, the quencher is acidic and at least about 1 equivalent of base is added to neutralize the quencher. A solution comprising such a neutralized quencher may be, in some instances, basic, neutral, or even acidic. In some embodiments, about 1 equivalent of base is added to neutralize or partially neutralize the quencher. In some embodiments, about 2 equivalents of base are added. In some embodiments, the quencher is acidic and about 0.5 to about 1.5 equivalents of base is used to neutralize the quencher. In some embodiments, about 0.75 to about 1.25 equivalents of base are used. In some embodiments, about 1 equivalent of base is used.

In some embodiments, the quencher is neutralized prior to addition to the whole blood composition and/or PIC. In other embodiments, the quencher is neutralized after combining the quencher with either the whole blood composition and/or PIC. In some embodiments, the pH of the neutralized quencher prior to addition to the whole blood composition and/or PIC is in the range of about 2.5 to 7.5, about 3.0 to 6.5, about 3.5 to 5.5, about 4.0 to 5.0, or about 4.3 to 4.5, or about 4.4.

In some embodiments, the quencher is glutathione and is provided in the form of glutathione monosodium salt and is neutralized with about 1 equivalent of base, or is not neutralized with base. In some other embodiments, the quencher is glutathione and is provided in the form of glutathione hydrochloride salt and is neutralized with about 1 equivalent of base.

In some embodiments of each of the methods described herein, the initial concentration of the quencher in the mixture comprising the whole blood composition, quencher, PIC, and any added base is elevated during a period for inactivation, and then reduced to a lowered concentration following the period of inactivation. In some embodiments, the initial concentration of the quencher is adequate to sufficiently reduce unwanted side reactions of the PIC (e.g., binding of the pathogen inactivation compound to RBC surfaces), then reduced to a lowered concentration to sufficiently reduce adversely affecting the vitality (e.g., osmotic fragility and dehydration) and/or lifespan of RBCs during storage of the treated whole blood composition.

Pathogen-Inactivated Whole Blood Compositions and Methods

Certain aspects of the present disclosure provide pathogen-inactivated whole blood compositions and methods (e.g., methods of preparation), and kits related thereto. A particular benefit, among others, provided by the improvements disclosed herein is the opportunity to prepare (e.g., produce) pathogen-inactivated whole blood compositions suitable for infusion with decreased residual levels of pathogen inactivation compound (PIC) in the composition. Decreased residual levels of PIC in treated whole blood compositions may provide improved safety profiles and/or improved consistency of pathogen inactivation processes, such as for example to achieve residual PIC levels below a certain threshold. The improved kits and related methods also provide an opportunity for preparing pathogen inactivated whole blood compositions under conditions where access to suitable facilities and/or power sources may not be readily available, such as in war zones.

Whole blood compositions, such as for example, whole blood compositions for treatment with a pathogen-inactivation process of the present disclosure include, but are not limited to, any whole blood composition (whole blood product) that is suitable for use in humans, mammals, and/or vertebrates, such as for infusion. In some embodiments, a whole blood composition comprises whole blood from a human donor. Such whole blood cell compositions may, in some embodiments, include buffers, salts, nutrients, and other solutions, such as for example, anticoagulants. Pathogen-inactivated whole blood compositions may, in some embodiments, include chemicals, such as pathogen inactivation compounds and quenchers. Suitable anticoagulants and their use are well known in the art, and may include, for example, CPD (Citrate Phosphate Dextrose), Citrate Phosphate Double Dextrose (CP2D) or Citrate Phosphate Dextrose Adenine (CPDA-1). An anticoagulant may be mixed with a whole blood composition at the time of collection from a donor, for example with the whole blood composition and anticoagulant mixed in a blood collection container (e.g., separate from the kits provided herein) or alternatively with the whole blood composition and anticoagulant mixed in a kit of the present disclosure. For example, a first container of a kit provided herein, may contain an anticoagulant (e.g., anticoagulant solution) prior to addition (e.g., collection, transfer) of the whole blood composition into the first container.

Whole blood compositions of the present disclosure (e.g., for pathogen inactivation treatment) may generally comprise any whole blood collection volume known in the art. In some embodiments, the volume of whole blood in a whole blood composition is about 200 mL to about 650 mL, about 250 mL to about 600 mL, about 300 mL to about 600 mL, about 300 mL to about 500 mL, about 400 mL to about 550 mL, about 400 mL to about 500 mL, or about 450 mL to about 500 mL of whole blood (e.g., about 200 mL, about 250 mL, about 300 mL, about 325 mL, about 350 mL, about 375 mL, about 400 mL, about 425 mL, about 450 mL, about 475 mL, about 500 mL, about 525 mL, about 550 mL, about 575 mL, about 600 mL, or about 650 mL). In some embodiments, the volume of whole blood is an above-mentioned volume±a certain variation, such as for example ±10% volume or ±50 mL.

The whole blood composition may further comprise an anticoagulant solution prior to transferring into a kit of the present disclosure (e.g., from a donor collection bag) or alternatively may be mixed with an anticoagulant in a kit of the present disclosure. In some embodiments, a first container of a kit of the disclosure may contain an anticoagulant for mixing (e.g., combining) with a whole blood composition upon addition (e.g., transfer) of the whole blood composition into the container. Suitable volumes of anticoagulant for mixing with whole blood (e.g., in a whole blood composition) are well known in the art, and in some embodiments may comprise for example about 30 mL to about 120 mL, about 50 mL to about 120 mL, about 60 mL to about 120 mL, about 50 mL to about 100 mL, about 50 mL to about 75 mL, about 60 mL to about 100 mL, about 60 mL to about 90 mL, about 60 mL to about 80 mL, or about 60 mL to about 70 mL. In some embodiments, an anticoagulant of the present disclosure comprises about 30 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 105 mL, about 110 mL, or about 120 mL.

The volume of anticoagulant may be any volume provided herein that results in a suitable anticoagulant to whole blood ratio (e.g., volume ratio) when mixed whole blood. For example, in some embodiments, the ratio of anticoagulant to whole blood (e.g., in a whole blood composition) is about 1:3 to about 1:10, about 1:4 to about 1:10, about 1:5 to about 1:9, about 1:6 to about 1:8. In some embodiments, the ratio of anticoagulant to whole blood is about 1:3, about 1:4, about 1:5, or about 1:6. In some embodiments, the ratio of anticoagulant to whole blood is about 1:8, about 1:9, or about 1:10. In some embodiments, the ratio of anticoagulant to whole blood is about 1:7.

In some embodiments, a whole blood composition (e.g., comprising whole blood and an anticoagulant) for use in a pathogen-inactivation process of the present disclosure has a volume of about 200 mL to about 700 mL, about 250 mL to about 700 mL, about 300 mL to about 700 mL, about 200 mL to about 650 mL, about 250 mL to about 650 mL, about 250 mL to about 600 mL, about 300 mL to about 650 mL, about 300 mL to about 600 mL, about 300 mL to about 550 mL, about 300 mL to about 500 mL, about 400 mL to about 650 mL, about 400 mL to about 600 mL, about 400 mL to about 550 mL, about 450 mL to about 650 mL, about 450 mL to about 600 mL, about 450 mL to about 550 mL, about 450 mL to about 500 mL, about 450 mL to about 500 mL, about 500 mL to about 650 mL, about 500 mL to about 600 mL, or about 500 mL to about 550 mL of whole blood (e.g., about 200 mL, about 250 mL, about 300 mL, about 325 mL, about 350 mL, about 375 mL, about 400 mL, about 425 mL, about 450 mL, about 475 mL, about 500 mL, about 525 mL, about 550 mL, about 575 mL, about 600 mL, about 625 mL, about 650 mL, about 675 mL, or about 700 mL. In some embodiments, the whole blood composition comprises about 400 mL to 500 mL of whole blood and about 50 mL to about 100 mL of anticoagulant. In some embodiments, the whole blood composition comprises about 450 mL to about 500 mL of whole blood and about 60 mL to about 70 mL of anticoagulant.

A whole blood composition (e.g., whole blood with anticoagulant) may be transferred into a kit of the present disclosure from a blood collection container. In some embodiments, a blood collection container containing a whole blood composition may be coupled (e.g., connected) to a kit by way of a conduit compatible with blood products (e.g., hemocompatible) with the conduit providing a fluid communication path for the whole blood composition to be transferred (e.g., sterilely) into a container of the kit, for example a hemocompatible container (e.g., blood product bag) of sufficient size for the combined volumes of whole blood composition, PIC, and any quencher, anticoagulant and/or other desired additions. For example, flexible tubing is commonly used in the art for coupling (e.g., connecting) one or more blood product containers (e.g., of a processing set or kit). In some embodiments, a conduit may be used to couple a blood collection container containing a whole blood composition with an inlet (e.g., first inlet) of a container (e.g., first container) of a kit, such as for example by sterile docking of two segments of tubing (e.g., one connected to the blood collection container, one connected to a container of the kit) using a sterile connecting device (e.g., SCD, tubing welder), so as to provide a fluid communication path. After transfer of the whole blood composition into a container of the kit, the conduit may be sealed and severed, thereby disconnecting the blood collection container from the kit.

Alternatively, a whole blood composition may be collected directly from a donor into a kit of the present disclosure. For example, in some embodiments, a kit of the disclosure comprises a vascular access device (e.g., needle) for drawing whole blood from a donor (e.g., by venipuncture), and a conduit (e.g., tubing, flexible tubing) extending between the vascular access device and a container of the kit, such as for example a first inlet of a first container. The conduit thereby provides a fluid communication path for transferring (e.g., sterilely) the whole blood being drawn from a donor using the vascular access device into the container of the kit. Generally, for embodiments wherein whole blood is collected directly into a container (e.g., first container) of a kit, the container contains anticoagulant for mixing (e.g., combining) with the whole blood (e.g., prior to mixing whole blood and PIC). After collection of the whole blood composition into a container of the kit, the conduit may in some embodiments be sealed and severed, thereby disconnecting the vascular access device from the kit.

In some embodiments, the whole blood compositions described herein have been leukocyte reduced (leukoreduced) prior to use in the methods of treating for pathogen inactivation described herein. For example, whole blood may be leukoreduced using a closed (e.g., functionally closed) system, such as filtration through an in-line filter integral to or sterile connected to a whole blood collection set or kit of the present disclosure. Suitable leukoreduction filters are known in the art. In some embodiments, the whole blood compositions have not been leukoreduced. Any whole blood composition that will come into contact with, or be introduced into, a living human, mammal, or vertebrate, where such contact carries a risk of transmitting disease due to contaminating pathogens may be treated as disclosed herein. Similarly, any whole blood composition that will be used to prepare one or more other blood products (e.g., red blood cells, plasma, platelets, cryoprecipitate) that will come into contact with, or be introduced into, a living human, mammal, or vertebrate, where such contact carries a risk of transmitting disease due to contaminating pathogens may be treated as disclosed herein.

In some embodiments, methods of the present disclosure for preparing a pathogen-inactivated whole blood composition include: (a) mixing (e.g., combining, adding) in a first container (i) a whole blood composition; (ii) an effective amount of a pathogen inactivation compound (PIC); and (iii) optionally an effective amount of a quencher; (b) incubating in the first container the mixture (e.g., admixture) of the whole blood composition, the PIC and optionally the quencher, under conditions and for a time sufficient to inactivate a pathogen, if present; (c) transferring the mixture under sterile conditions to a second container; and (d) incubating in the second container the mixture under conditions and for a time sufficient to reduce the concentration of the PIC (i) to a concentration at least 25% less than the concentration of the PIC in the mixture at the time of transfer step (b); (ii) to a concentration at least $10^5$ fold less than (e.g., lower than) the concentration (e.g., initial concentration, concentration prior to the incubating step (b)) of the PIC in the mixture of step (a); and/or (iii) to a concentration of about 1 nm or less, thereby yielding the pathogen inactivated whole blood composition. Further provided herein are pathogen-inactivated whole blood compositions prepared by any of the methods of the present disclosure.

In some embodiments of the methods provided herein, the concentration of the PIC, such as amustaline, in the mixture (e.g., admixture) of step (a) (e.g., mixture of whole blood composition, anticoagulant, PIC, optionally quencher) is at least about 0.05 mM, at least about 0.1 mM or at least about 0.2 mM, or more. In some embodiments, the concentration of the PIC in the mixture of step (a) is about 0.1 mM to about 10 mM. In some embodiments, the concentration of the PIC in the mixture of step (a) is less than about 10 mM, less than about 5 mM, less than about 4 mM, less than about 3 mM, less than about 2 mM, less than about 1.0 mM or less than about 0.5 mM. The concentration of the PIC in the mixture of step (a) generally refers to the initial concentration of the PIC upon mixing (e.g., combining, immediately after mixing) the components of step (a), such as for example, the whole blood composition, the PIC, any anticoagulant, and any quencher, and prior to the incubating step (b). In some embodiments, the concentration of the PIC in the mixture of step (a) is about 0.05 mM to about 10.0 mM, about 0.05 mM to about 5.0 mM, about 0.05 mM to about 4.0 mM, about 0.05 mM to about 2.0 mM, about 0.05 mM to about 1.0 mM, about 0.05 mM to about 0.5 mM, about 0.1 mM to about 10 mM, about 0.1 mM to about 5 mM, about 0.1 mM to about 4 mM, about 0.1 mM to about 3 mM, about 0.1 mM to about 2 mM, about 0.1 mM to about 1.0 mM, about 0.1 mM to about 0.5 mM, or about 0.1 mM to about 0.3 mM. In some embodiments, the concentration of the PIC in the mixture of step (a) is about 0.05 mM, about 0.07 mM, about 0.08 mM, about 0.09 mM, 0.1 mM, 0.2 mM, 0.3 mM, 0.4 mM, 0.5 mM, 0.6 mM, 0.7 mM, 0.8 mM, 0.9 mM 1.0 mM, about 2.0 mM, about 3.0 mM, about 4.0 mM, about 5 mM, about 6 mM, about 7 mM, about 8 mM, about 9 mM or about 10 mM. In some embodiments, the concentration of the PIC in the mixture of step (a) is about 0.2 mM. In some embodiments, the PIC comprises a functional group which is, or which forms, a reactive electrophilic group. In some embodiments, the functional group is selected from the group consisting of a mustard, a mustard intermediate, and a mustard equivalent. In some embodiments, the functional group is, or is capable of forming, an aziridinium ion. In some embodiments, the reactive electrophilic group is capable of reacting with nucleic acids. In some embodiments, the PIC comprises a nucleic acid binding ligand. In some embodiments, the nucleic acid binding ligand is an intercalator. In some embodiments, the intercalator is an acridine. In some embodiments, the PIC comprises a frangible linker linking the functional group and the nucleic acid binding ligand. In some embodiments, the PIC is β-alanine, N-(acridin-9-yl), 2-[bis(2-chloroethyl)amino]ethyl ester.

In some embodiments of the methods provided herein, step (a) comprises mixing (e.g., combining, adding) in the first container a whole blood composition, an effective amount of a PIC, and an effective amount of a quencher. In some embodiments, the concentration (e.g., initial concentration, concentration prior to the incubating step (b)) of the quencher in the mixture (e.g., admixture) of step (a) is at least about 1 mM, at least about 2 mM, at least about 3 mM, at least about 4 mM, or at least about 5 mM. In some embodiments, the concentration of the quencher in the mixture of step (a) is less than about 25 mM, less than about 20 mM, less than about 15 mM, or less than about 10 mM. In some embodiments, the concentration of the quencher in the mixture of step (a) is about 1 mM to about 25 mM. In some embodiments, the concentration of the quencher in the mixture of step (a) is about 1 mM to about 20 mM. In some embodiments, the concentration of the quencher in the mixture of step (a) is about 1 mM to about 15 mM. In some embodiments, the concentration of the quencher in the mixture of step (a) is about 1 mM to about 10 mM. In some embodiments, the concentration of the quencher in the mixture of step (a) is about 1 mM to about 5 mM. In some embodiments, the concentration of the quencher in the resulting mixture of step (a) is about 1 mM, about 2 mM, about 3 mM, about 4 mM, about 5 mM, about 6 mM, about 7 mM, about 8 mM, about 9 mM, or about 10 mM. In some embodiments, the concentration of the PIC in the mixture of step (a) is about 0.1 mM and the concentration of the quencher in the admixture of step (a) is about 1 mM, about 2 mM, about 2 mM, about 4 mM, about 5 mM, about 6 mM, about 7 mM, about 8 mM, about 9 mM, or about 10 mM. In some embodiments, the concentration of the PIC in the mixture of step (a) is about 0.2 mM and the concentration of the quencher in the mixture of step (a) is about 1 mM, about 2 mM, about 2 mM, about 4 mM, about 5 mM, about 6 mM, about 7 mM, about 8 mM, about 9 mM, or about 10 mM. In some embodiments, the concentration of the PIC in the mixture of step (a) is about 0.2 mM and the concentration of the quencher in the mixture of step (a) is about 1 mM, about 2 mM, about 2 mM, about 4 mM, about 5 mM, about 6 mM, about 7 mM, about 8 mM, about 9 mM, or about 10 mM. In some embodiments, the concentration of the PIC in the mixture of step (a) is about 0.2 mM and the concentration of the quencher in the mixture of step (a) is about 1 mM to about 5 mM. In some embodiments, the concentration of the PIC in the mixture of step (a) is about 0.2 mM and the concentration of the quencher in the admixture of step (a) is about 2 mM. In some embodiments, the quencher comprises a thiol group, wherein the thiol is capable of reacting with a reactive electrophilic group of the pathogen inactivation compound. In some embodiments, the quencher comprises cysteine or a derivative of cysteine. In some embodiments, the quencher is glutathione or a pharmaceutically acceptable salt thereof. In some embodiments, the quencher is glutathione monosodium salt.

In some embodiments, the molar ratio of quencher to pathogen inactivation compound once both components have been mixed with the whole blood composition is about 5:1 to about 100:1, about 5:1 to about 50:1, about 5:1 to about 40:1, about 5:1 to about 30:1, about 5:1 to about 20:1, about 5:1 to about 10:1, about 10:1 to about 100:1, about 10:1 to about 50:1, about 10:1 to about 40:1, about 10:1 to about 30:1, or about 10:1 to about 20:1. In some embodiments, the molar ratio of quencher to pathogen inactivation compound once both components have been mixed with the whole blood composition is about 5:1, about 6:1, about 7:1, about 8:1, about 9:1, about 10:1, about 11:1, about 12:1, about 13:1, about 14:1, about 15:1, or about 20:1.

The PIC and optional quencher may be added into a container (e.g., first container) of the kit using any of the methods and kits of the disclosure. In some embodiments, the PIC and optional quencher may be added into a first container of a kit of the present disclosure. In some embodiments, the PIC and optionally the quencher are added into the first container through a first inlet of the first container. In some embodiments, both the PIC and the quencher are added into the first container through a first inlet of the first container. In some embodiments, the PIC is added into the first container from a container containing the PIC (PIC container), wherein the PIC container is coupled to the first container. In some embodiments, the PIC container is coupled to a first inlet of the first container. In some embodiments, the PIC container is coupled to a second inlet of the first container. In some embodiments, the quencher is added into the first container from a container containing the quencher (quencher container), wherein the quencher container is coupled to the first container. In some embodiments, the quencher container is coupled to a first inlet of the first container. In some embodiments, the quencher container is coupled to a second inlet of the first container. In some embodiments, both the PIC container and the quencher container are coupled to a first inlet of the first container. In some embodiments, both the PIC container and the quencher container are coupled to a second inlet of the first container.

In some embodiments, the PIC and optionally the quencher are added into the first container through a conduit (e.g., flexible tubing) extending between (e.g., coupling) a PIC container and optionally a quencher container and the first container, and providing a fluid communication path for transferring the PIC from the PIC container and optionally for transferring the quencher from the optional quencher container, into the first container. In some embodiments, the PIC and the quencher are added into the first container through a conduit extending between a PIC container and a quencher container and an inlet of the first container, and providing a fluid communication path for transferring the PIC from the PIC container and for transferring the quencher from the optional quencher container, into the first container. In some embodiments, the PIC and the quencher are added into the first container through a conduit extending between a PIC container and a quencher container and a first inlet of the first container. In some embodiments, the PIC and the quencher are added into the first container through a conduit extending between a PIC container and a quencher container and a second inlet of the first container. In some embodiments, the PIC container and the quencher container are the same container. In some embodiments, the PIC and the quencher are added into the first container through a conduit extending between a PIC container and a quencher container and an inlet of the first container, and the conduit comprises at one end: (a) a first adaptor for coupling the PIC container to the conduit, (b) a second adaptor for coupling the quencher container to the conduit, and optionally (c) a displacement device (e.g., an air displacement device) suitable for increasing the transfer of the PIC and the quencher through the conduit and into the first container. In some embodiments, the PIC and the quencher are added into the first container through a conduit extending between a PIC container and a quencher container and an inlet of the first container, and the conduit comprises at one end: (a) a first adaptor for coupling the PIC container to the conduit, (b) a second adaptor for coupling the quencher container to the conduit, and (c) a displacement device (e.g., an air displacement device) suitable for increasing the transfer of the PIC and the quencher through the conduit and into the first container. In some embodiments, air is transferred from the displacement device (e.g., air displacement device) into the conduit, thereby increasing the transfer (e.g., percentage of fluid volume transferred) of the PIC and the quencher into the first container. In some embodiments, fluid (e.g., saline) is transferred from the displacement device into the conduit, thereby increasing the transfer (e.g., percentage of fluid volume transferred) of the PIC and the quencher into the first container. In some embodiments, the PIC container is coupled to the first adaptor of the conduit after the conduit comprising the adaptor is coupled to the first container. In some embodiments, the quencher container is coupled to the second adaptor of the conduit after the conduit comprising the adaptor is coupled to the first container.

In some embodiments, the conduit extending between a PIC container and an optional quencher container and an inlet of the first container, is coupled to the first container after the whole blood composition is added into the first container. In some embodiments, the conduit extending between a PIC container and a quencher container and an inlet of the first container, is coupled to the first container after the whole blood composition is added into the first container. In some embodiments, the conduit extending between a PIC container and an optional quencher container and an inlet of the first container, is coupled to a first inlet of the first container after the whole blood composition is added into the first container through the first inlet of the first container. In some embodiments, the conduit extending between a PIC container and an optional quencher container and an inlet of the first container, is coupled to a first inlet of the first container after the whole blood composition is added into the first container through the first inlet of the first container. In some embodiments, the conduit extending between a PIC container and a quencher container and an inlet of the first container, is coupled to a first inlet of the first container after the whole blood composition is added into the first container through the first inlet of the first container. For example, after transferring a whole blood composition from a blood collection container or vascular access device into the first container through a conduit coupling the blood collection container or vascular access device to a first inlet of the first container, the conduit may be sealed and severed, thereby disconnecting the blood collection container or the vascular access device from the kit (e.g., from the first container). The source of a PIC (e.g., PIC container) and the source of a quencher (e.g., quencher container) may then be coupled to the remaining sealed and severed conduit extending from the first inlet of the first container of the kit. In some embodiments, both a PIC container and a quencher container are coupled to conduit extending from the first container of a kit. In some embodiments, the PIC container is coupled to a first adaptor of the conduit and the quencher container is coupled to a second adaptor of the conduit after the whole blood composition is added into the first container (e.g., and after the conduit is coupled to the first container).

In some embodiments, the whole blood composition is added into the first container through the first inlet of the first container, and the PIC and optional quencher are added into the first container through a second inlet of the first container. In some embodiments, the conduit extending between a PIC container and an optional quencher container and an inlet of the first container, is coupled to the second inlet of the first container. For example, in some embodiments, the whole blood composition may be transferred into the first container from a blood collection container or vascular access device coupled (e.g., by way of a first conduit) to the first inlet of the first container, the conduit may optionally be sealed and severed after transfer of the whole blood composition, thereby disconnecting the blood collection container or the vascular access device from the kit, and the PIC and optional quencher then may be transferred into the first container from the source of the PIC (e.g., PIC container) and the source of the optional quencher (e.g., quencher container) coupled (e.g., by way of a second conduit) to the second inlet of the first container. In some embodiments, the second conduit comprises at one end at least one adaptor for coupling the PIC container and/or the quencher container to the second conduit. In some embodiments, the second conduit comprises at one end a first adaptor for coupling the PIC container a second adaptor for coupling the quencher container to the conduit. In some embodiments, the second conduit is coupled to the second inlet of the first container before the PIC container is coupled to the first adaptor or the quencher container is coupled to the second adaptor of the conduit.

Upon addition (e.g., transfer) to (e.g., and mixing in) a container (e.g., first container) of a kit, a whole blood composition, an effective amount of a PIC, and optionally an effective amount of a quencher, the mixture (e.g., admixture) is incubated in the first container under conditions and for a time sufficient to inactivate a pathogen, if present. In some embodiments, the incubating step (e.g., step (b)) is about 2 hours to about 24 hours. In some embodiments, the incubating step (e.g., step (b)) is about 6 hours to about 24 hours, about 12 hours to about 24 hours, or about 18 to about 24 hours. In some embodiments, the incubating step (e.g., step (b)) is about 18 hours to about 22 hours (e.g., about 18 hours, about 19 hours, about 20 hours, about 21 hours, about 22 hours). In some embodiments, the incubating step (e.g., step (b)) is about 20 hours. In some embodiments, the incubating step (b) is at about 18° C. to 25° C. In some embodiments, the incubating step (e.g., step (b)) is at room temperature (e.g., 22° C.).

In some embodiments, the mixture comprising a whole blood composition, the PIC, and optionally the quencher, is transferred (e.g., under sterile conditions) to a second container after the incubating step (e.g., step (b)) in the first container. In some embodiments, the second container is coupled to the first container. In some embodiments, the mixture is transferred (e.g., transferring step (c)) through a conduit, such as for example flexible tubing, extending between (e.g., coupling, connecting) the first container to the second container. In some embodiments, the conduit extends between (e.g., connects, provides a fluid communication path) a first outlet of the first container and a first inlet of the second container. In some embodiments, the method further comprises incubating the mixture in the second container (e.g., for a time sufficient to reduce the PIC). In some embodiments, the incubating step in the second container (e.g., step (d)) is about 1 hour to about 12 hours, about 1 hour to about 10 hours, about 1 hour to about 8 hours, about 1 hour to about 6 hours. In some embodiments, the incubating step (e.g., step (d)) is about 2 hours to about 4 hours. In some embodiments, the incubating step (e.g., step (d)) is about 1 hour, about 2 hours, about 3 hours, about 4 hours, about 5 hours, about 6 hours, about 7 hours, about 8 hours, about 9 hours, about 10 hours, about 11 hours, or about 12 hour, or more. In some embodiments, the incubating step is at about 18° C. to 25° C. In some embodiments, the incubating step is at room temperature (e.g., 22° C.). In some embodiments, the pathogen-inactivated whole blood composition is stored in the second container after the incubating step. In some embodiments, the pathogen-inactivated whole blood composition is transferred from the second container to a third container. In some embodiments, the third container is coupled to the second container. In some embodiments, the pathogen-inactivated whole blood composition is transferred from the second container to the third container through a conduit, such as for example flexible tubing, extending between (e.g., coupling, connecting) the second container to the third container. In some embodiments, the conduit extends between (e.g., connects, provides a fluid communication path) a first outlet of the second container and a first inlet of the third container. In some embodiments, the pathogen-inactivated whole blood composition is stored in the third container. In some embodiments, the pathogen-inactivated whole blood composition is stored at about 2-6° C. (e.g., in the second container, in the third container). In some embodiments, the pathogen-inactivated whole blood composition is suitable for infusion (e.g., infusion of a human subject).

In some embodiments, after incubating the mixture in the second container (e.g., incubating step (d)), the concentration of the PIC is reduced. In some embodiments, after incubating the mixture in the second container (e.g., incubating step (d)), the concentration of the PIC is reduced: (i) to a concentration at least 25% less than the concentration of the PIC in the mixture at the time of transfer step (b); (ii) to a concentration at least $10^5$ fold less than (e.g., lower than) the concentration (e.g., initial concentration, concentration prior to the incubating step (b)) of the PIC in the mixture of step (a); and/or (iii) to a concentration of about 1 nm or less, thereby yielding the pathogen inactivated whole blood composition.

In some embodiments, after incubating the mixture in the second container (e.g., incubating step (d)) the concentration of the PIC is reduced to a concentration at least 10% less, at least 15% less, at least 20% less, at least 25% less, at least 30% less, at least 35% less, at least 40% less, at least 45% less, at least 50% less, at least 60% less, at least 70% less, at least 80% less or at least 90% less than the concentration of the PIC in the mixture at the time of transfer to the second container (e.g., transfer step (b)). In some embodiments, after incubating the mixture in the second container (e.g., incubating step (d)) the concentration of the PIC is reduced to a concentration at least $10^4$ fold, at least $10^{4.5}$ fold, at least $10^5$ fold, at least $10^{5.5}$ fold, at least $10^6$ fold, at least $10^{6.5}$ fold, or at least $10^7$ fold less than the concentration (e.g., initial concentration, concentration prior to the incubating step (b)) of the PIC in the mixture of step (a). In some embodiments, after incubating the mixture in the second container (e.g., incubating step (d)) the concentration of the PIC is reduced to a concentration less than about 2.0 nM, less than about 1.5 nM, less than about 1.25 nM, less than about 1.0 nM, less than about 0.9 nM, less than about 0.8 nM, less than about 0.75 nM, or less than about 0.7 nM. In some embodiments, after incubating the mixture in the second container (e.g., incubating step (d)) the concentration of the PIC is reduced to a concentration less than the limit of quantitation using an LCMS.

Pathogen-inactivated whole blood compositions and blood components derived therefrom of the present disclosure may be characterized for a variety of parameters (e.g, functional characterization, using analytical methods known in the art). Non-limiting examples include percent hemolysis, pH (e.g., at 37° C.), $pO_2$, $pCO_2$, $HCO^-_3$, Total ATP, extracellular $K^+/Na^+$, extracellular glucose and lactate, hematocrit, hemoglobin content, albumin level, coagulation factor activity, calibrated automated thrombogram (CAT), thrombin generation capacity, prothrombin time (PT) activated partial thromboplastin time (aPTT), thrombin time (TT), rotational thromboelastometry (ROTEM), P-selectin, GPIIb/IIIa, and platelet aggregation.

In some embodiments, the method further comprises separating the pathogen-inactivated whole blood composition into one or more of a red blood cell composition, a plasma composition, or a platelet composition (e.g., a pathogen-inactivated red blood cell composition, a pathogen-inactivated plasma composition, a pathogen-inactivated platelet composition). In some embodiments, the method further comprises separating the pathogen-inactivated whole blood composition into a red blood cell composition and a plasma composition. In some embodiments, the method further comprises separating the pathogen-inactivated whole blood composition into at least a plasma composition, and preparing a cryoprecipitate composition (e.g., pathogen-inactivated cryoprecipitate composition) from the plasma composition. In some embodiments, preparing a cryoprecipitate composition from the plasma composition, includes preparing a cryo-reduced (e.g., cryo-poor) plasma composition (e.g., pathogen-inactivated cryo-reduced plasma composition). Methods of separating whole blood into a red blood cell composition, a plasma composition, and/or a platelet composition are well known in the art. In some embodiments, a method known in the art is used to separate a pathogen-inactivated whole blood prepared according to the disclosure into one or more of a red blood cell composition, a plasma composition, and/or a platelet composition. Likewise, methods of preparing a cryoprecipitate composition and cryo-reduced (e.g., cryo-poor) plasma composition from plasma are well known in the art. In some embodiments, a method known in the art is used to prepare a cryoprecipitate composition and/or cryo-reduced plasma composition from plasma obtained by separating a pathogen-inactivated whole blood prepared according to the disclosure into a plasma composition.

In another aspect, the present disclosure provides a pathogen-inactivated whole blood composition prepared by any of the aforementioned methods. In some embodiments, the pathogen-inactivated whole blood composition is suitable for infusion. In some embodiments, the pathogen-inactivated whole blood composition is a pathogen-inactivated whole blood unit suitable for infusion. In some embodiments, the pathogen-inactivated whole blood composition suitable for infusion comprises PIC at a concentration less than about 2.0 nM, less than about 1.5 nM, less than about 1.25 nM, less than about 1.0 nM, less than about 0.9 nM, less than about 0.8 nM, less than about 0.75 nM, or less than about 0.7 nM. Another aspect of the present disclosure provides a pathogen-inactivated red blood cell composition prepared by any of the aforementioned methods. Another aspect of the present disclosure provides a pathogen-inactivated plasma composition prepared by any of the aforementioned methods. Another aspect of the present disclosure provides a pathogen-inactivated platelet composition prepared by any of the aforementioned methods. Another aspect of the present disclosure provides a pathogen-inactivated cryoprecipitate composition prepared by any of the aforementioned methods. Another aspect of the present disclosure provides a pathogen-inactivated cryo-reduced plasma composition prepared by any of the aforementioned methods.

The methods of the disclosure, in some embodiments, include the ex vivo use of a pathogen inactivation compound and a quencher. The ex vivo use involves using the compounds for treatment of a whole blood composition, outside of a living human, mammal, or vertebrate, where the treated biological material is intended for use inside of a living human, mammal, or vertebrate. For example, removal of blood from a human, and introduction of a compound into that blood to inactivate pathogens, is defined as an ex vivo use of the compound if the blood is intended for reintroduction into that human or another human. Reintroduction of the human blood into that human or another human would be in vivo use of the blood, as opposed to the ex vivo use of the compound. If the compound is still present in the blood when it is reintroduced into the human, then the compound, in addition to its ex vivo use, is also introduced in vivo. Some embodiments of the present disclosure involve the ex vivo use of a quencher, where the whole blood composition is intended for in vivo use. In some instances, some level of quencher remains in the whole blood composition such that the quencher is also introduced in vivo. The in vitro use of a material or compound involves a use of the material or compound outside of a living human, mammal, or vertebrate, where the material or compound is not intended for reintroduction into a living human, mammal, or vertebrate. An example of an in vitro use would be the diagnostic analysis of components of a whole blood sample. The methods of the disclosure may be applied to the in vitro use of the whole blood compositions, as modification of the whole blood or other constituents may affect the in vitro analysis of the components of the blood sample. Thus, the methods of the disclosure may provide safety in handling of such in vitro samples with adequate quenching of modifications of the sample that might otherwise interfere with diagnostic testing of the sample.

Treated Whole Blood Compositions

In some embodiments, the disclosure also provides whole blood compositions resulting from each of the treatment methods described herein. In some embodiments, the disclosure also provides whole blood compositions preparable by each of the treatment methods described herein.

In some embodiments of each of the methods and compositions described herein, the whole blood in the whole blood composition is mammalian blood. For instance, the whole blood may be rodent (e.g., mouse or rat), canine, lagomorph (e.g., rabbit), non-human primate (e.g., chimpanzee), or human whole blood. For example, in some embodiments, the whole blood is human. In some embodiments, the whole blood has been leukoreduced. In some other embodiments, the whole blood has not been leukoreduced. In some embodiments, there is a possibility that the composition comprising whole blood is contaminated with a pathogen. In some embodiments, the whole blood composition is contaminated with a pathogen. In some embodiments, at least 1 log, or at least 2 logs, or at least 3 logs, at least 4 logs, at least 5 logs, at least 6 logs or more of pathogen in the composition is inactivated, if present.

The kits of the present disclosure may find use, inter alia, in preparing from the pathogen-inactivated whole blood composition, one or more pathogen-inactivated blood components, such as for example a plasma composition, a red blood cell composition, and/or a platelet composition, e.g., as described herein. Additional pathogen-inactivated blood products may be prepared from such blood components, including for example, a cryoprecipitate and/or a cryoreduced (e.g., “cryo poor”) plasma.

A pathogen-inactivated whole blood composition of the present disclosure may find use in a variety of applications known in the art. In certain aspects, provided herein are methods of infusing a pathogen-inactivated whole blood composition of the present disclosure into a subject in need thereof. In some embodiments, the subject is a human subject. Any of the whole blood compositions of the present disclosure may find use in a method of infusion.

Whole Blood Processing and Kits

Certain aspects of the present disclosure relate to kits (e.g., pathogen inactivation kits). The kits and related processing sets of the present disclosure may find use, inter alia, in preparing a pathogen-inactivated whole blood composition and other pathogen-inactivated blood products, e.g., as described herein. Any of the exemplary components such as containers, bags and conduits (e.g., tubings) described infra may find use in the kits of the present disclosure.

In one aspect, a kit is provided for preparing a pathogen-inactivated whole blood composition, the kit comprising: a vascular access device (e.g., needle, venipuncture needle) for drawing whole blood from a donor; a first container suitable for mixing (e.g., combining, adding) the whole blood and a pathogen inactivation compound (PIC), wherein the first container comprises (e.g., includes) at least a first inlet and a first outlet, and wherein the vascular access device is coupled to a first inlet of the first container; and a container containing a pathogen inactivation compound (PIC container). In some embodiments, a kit is provided for preparing a pathogen-inactivated whole blood composition, the kit comprising: (a) a vascular access device for drawing whole blood from a donor, (b) a first container suitable for mixing (e.g., combining, adding) the whole blood and a pathogen inactivation compound (PIC), wherein the first container comprises at least a first inlet and a first outlet; (c) a first conduit extending between the vascular access device and the first inlet of the first container, and providing a fluid communication path for transferring the whole blood from the vascular access device into the first container; and (d) a container containing a pathogen inactivation compound (PIC container), wherein the PIC container is configured to be coupled by a fluid communication path to the first container.

Containers for use with whole blood compositions in kits of the present disclosure are compatible for processing and/or storage of the whole blood and/or other blood product compositions (e.g., hemocompatible). Such containers may comprise any sheeting materials known in the art for use in blood product containers (e.g., PVC, EVA), and are of a size sufficient to contain a desired volume of whole blood together with any additional fluid volumes (e.g., anticoagulant, PIC, quencher) mixed with the whole blood composition. Containers may comprise one or more inlets (e.g., ports, access ports) and one or more outlets (e.g., ports, access ports) for access in transferring fluids, such as for example whole blood and/or a pathogen inactivation compound, into or out of a container. A number of suitable ports used in blood product containers are known in the art. In some embodiments, an inlet (e.g., port, access port, entry port) may be “open”, permitting fluid entry into a container, such as for example, when a conduit (e.g., tubing) is coupled to the inlet (e.g., providing a sterile connection and fluid path). Alternatively or in addition, an inlet may be “openable”, such as for example a frangible or pierceable port that permits fluid entry (e.g., sterile fluid path) into a container after a barrier is opened. Similarly, an outlet (e.g., port, access port, spike port) may in some embodiments be open or openable. In some embodiments, an inlet and an outlet of a container may be of a substantially similar configuration. In some embodiments, one or more containers of the present disclosure (e.g., first container, second container) comprise polyvinyl chloride (e.g., PVC, plasticized polyvinyl chloride). In some embodiments, one or more containers of the present disclosure (e.g., first container, second container) comprise a polyethylene (e.g., ethylene vinyl acetate, ethylene vinyl acetate copolymer). In some embodiments, one or more containers of the present disclosure (e.g., first container, second container) comprise a polyolefin (e.g., polyolefin blend). In some embodiments, one or more containers of the present disclosure (e.g., first container, second container) comprise a polyvinylidene fluoride (PVDF). Conduit (e.g., tubing, flexible tubing) for use with whole blood compositions in kits of the present disclosure is also compatible with whole blood and/or other blood product compositions (e.g., hemocompatible). In some embodiments, containers and/or conduit of the present disclosure do not comprise di-ethylhexyl phthalate (e.g., DEHP-free).

Vascular access devices, such as needles (e.g., vascular access needles) are typically used for drawing whole blood from a donor (e.g., by venipuncture) to be collected into a container, such as a blood collection container. In some embodiments, whole blood is collected with a vascular access device from a donor into a container of the present disclosure (e.g., transferred from the vascular access device into the first container of a kit). In some embodiments, donor whole blood is transferred from the vascular access device into the first container of a kit of the present disclosure through a conduit, such as for example, flexible hemocompatible tubing, that extends between the vascular access device and the first container, to provide a fluid communication path for sterilely transferring the whole blood. In some embodiments, the vascular access device and conduit comprise a needle assembly. Transfer (e.g., sterile transfer) of whole blood into the first container may be through an inlet (e.g., opening, port, access port) of the container to which the conduit is coupled (e.g., connected, attached). The conduit may comprise one contiguous segment of tubing, or more than one segment of tubing, such as for example, segments of tubing with one or more intervening components (e.g., connectors, filters, leukoreduction filters) that maintain a fluid communication path. The conduit may also include an internal frangible seal or closure (e.g., a frangible cannula) that may be broken and opened by external manipulation of the tubing, such as by bending the tubing. Such frangible closures are well known in the field.

In some embodiments, the PIC container is configured to be coupled by a fluid communication path to the first inlet of the first container. In some embodiments, the PIC container is configured to be coupled to the first conduit. In some embodiments, the first container comprises a second inlet and the PIC container is configured to be coupled by a fluid communication path to the second inlet of the first container. In some embodiments, the kit further comprises a container containing a quencher (quencher container), wherein the quencher container is configured to be coupled by a fluid communication path to the first container. In some embodiments, the quencher container is configured to be coupled by a fluid communication path to the first inlet of the first container. In some embodiments, the quencher container is configured to be coupled to the first conduit. In some embodiments, the quencher container is configured to be coupled by a fluid communication path to the second inlet of the first container. In some embodiments, the PIC container and the quencher container are the same container (e.g., container with more than one chamber). PIC and quencher containers of the present disclosure may comprise any suitable container for storing a PIC or quencher of a kit, including for example glass containers (e.g., vials), plastic containers (e.g., syringe), flexible bags, and the like. In some embodiments, such PIC and/or quencher containers may be configured to be coupled (e.g., connected) to a component of the kit (e.g., container, conduit, processing set) to permit fluid communication and transfer of the PIC and/or quencher. In some embodiments, a kit of the present disclosure may comprise a first PIC container and a second PIC container, with either or both of the first PIC container and the second PIC container configured to be coupled to a component of the kit (e.g., container, conduit, processing set). In some embodiments, a kit of the present disclosure may comprise a first quencher container and a second quencher container, with either or both of the first quencher container and the second quencher container configured to be coupled to a component of the kit (e.g., container, conduit, processing set). For example, in some embodiments, a kit (e.g., processing set) may comprise a first PIC container and first quencher container for reconstitution of lyophilized PIC and lyophilized quencher that are glass vials, and a second PIC container and a second quencher container that are syringes configured to be coupled to a conduit or container of the kit (e.g., with the reconstituted PIC and quencher transferred (e.g., sterilely) from their respective first containers to their respective second containers, which are configured to be coupled to a conduit or container of the kit). In some embodiments, coupling of a PIC and/or quencher container to a component (e.g., conduit, container) of a kit may be, for example, with an adaptor (e.g., luer adaptor). In some embodiments, coupling of a PIC and/or quencher container to a component of a kit (e.g., container, conduit, processing set may be, for example, with a conduit (e.g., sterile docking with a tubing welder). In some embodiments, PIC and/or quencher container are coupled to a component of the kit (e.g., container, conduit, processing set) during manufacturing, so as to be integrally connected within the kit. In some embodiments, the PIC container and the quencher container are the same container. For example, a PIC container and a quencher container may be portions (e.g., chambers, sub-containers) within a single container, for example to provide a configuration requiring only a single coupling (e.g., to a container, to a conduit) for transfer of the PIC and quencher to a container (e.g., first container).

In some embodiments, the kit further comprises a second conduit wherein the second conduit comprises at one end at least one adaptor for coupling the PIC container (e.g., second PIC container) and/or the quencher container (e.g., second quencher container) to the second conduit. In some embodiments, the second conduit comprises at one end a first adaptor for coupling the PIC container to the second conduit and a second adaptor for coupling the quencher container to the second conduit. In some embodiments, the second conduit comprises a 2-way branch at the end with the first adaptor and the second adaptor. In some embodiments, the kit further comprises a second conduit, wherein the second conduit is coupled at one end to the PIC container and/or the quencher container. In some embodiments, the kit further comprises a second conduit, wherein the second conduit is coupled at one end to the PIC container and the quencher container (e.g., with a 2-way branch). In some embodiments, the second conduit (e.g., other end of the second conduit) is configured to be coupled to the first container, providing a fluid communication path between the PIC container and/or quencher container and the first container. In some embodiments, the second conduit is configured to be coupled to the first inlet of the first container. In some embodiments, the second conduit is coupled to the second inlet of the first container. In some embodiments, the second conduit is configured to be coupled to the first conduit (e.g., by sterile docking), providing a fluid communication path between the PIC container and/or quencher container and the first container.

In some embodiments, the kit further comprises a displacement device (e.g., an air displacement device) suitable for increasing the transfer of the PIC and/or the quencher into a container of the present disclosure, such as for example the first container (e.g., through the second conduit and into the first container). Generally a displacement device, such as for example an air displacement device, of the present disclosure is any device or component of the kit that can displace air and/or fluid from the displacement device in a manner to facilitate the movement or transfer of a fluid (e.g., the PIC and/or quencher) through or from a conduit, such as for example, in the case of an air displacement device, by compressing the air displacement device, causing air (e.g., or a suitable gas) to push the fluid through a conduit to which it is coupled, to increase or maximize transfer (e.g., expel the fluid) and reduce or minimize the retained volume of fluid in the conduit. Displacement devices (e.g., air displacement devices) may be particularly useful when transferring smaller volumes of fluid such as a PIC and/or quencher, such as for example from a conduit into a container, where retained fluid (e.g., fluid not drained by gravity) in a conduit may impact the final concentration of PIC and/or quencher upon mixing with a whole blood composition. Air displacement devices contemplated for kits of the disclosure may include, but are not limited to, a sample diversion pouch, a syringe, a rubber bulb, a flexible container, a cartridge (e.g., gas cartridge) and the like. Generally the interior of an air displacement device and any gas (e.g., air) contained within are sterile, for example, sterilized as part of the manufacturing of kits. In some preferred embodiments, the air displacement device is a sample diversion pouch (e.g., air pillow, sampling pouch), examples of which are well known in the blood collection field. Other displacement devices contemplated for use in the present disclosure may include for example, fluid containing displacement devices, such as for example sterile saline solution in a container that may be used to facilitate transfer of the PIC and/or quencher. In some embodiments, the displacement device (e.g., air displacement device) is coupled to one end of a conduit (e.g., the second conduit) and the end of the conduit may also be coupled or configured to be coupled to a PIC container and/or quencher container, such as for example using a tubing branch connector (e.g., 3-way branch).

In some embodiments, the PIC (e.g., in a PIC container) comprises any of the pathogen inactivation compounds provided in the present disclosure. In some embodiment, the PIC comprises a functional group which is, or which forms, a reactive electrophilic group. In some embodiments, the functional group is selected from the group consisting of a mustard, a mustard intermediate, and a mustard equivalent. In some embodiments, the functional group is, or is capable of forming, an aziridinium ion. In some embodiments, the reactive electrophilic group is capable of reacting with nucleic acids. In some embodiments, the PIC comprises a nucleic acid binding ligand. In some embodiments, the nucleic acid binding ligand is an intercalator. In some embodiments, the intercalator is an acridine. In some embodiments, the PIC comprises a frangible linker linking the functional group and the nucleic acid binding ligand. In some embodiments, the PIC is β-alanine, N-(acridin-9-yl), 2-[bis(2-chloroethyl)amino]ethyl ester.

In some embodiments, the quencher (e.g., in a quencher container) comprises any of the quenchers provided in the present disclosure. In some embodiments, the quencher comprises a thiol group, wherein the thiol is capable of reacting with a reactive electrophilic group of the pathogen inactivation compound. In some embodiments, the quencher comprises cysteine or a derivative of cysteine. In some embodiments, the quencher is glutathione or a pharmaceutically acceptable salt thereof. In some embodiments, the quencher is glutathione monosodium salt.

In some embodiments, the first container of a kit contains an anticoagulant (e.g., anticoagulant solution), such as for example, any suitable anticoagulant for use with whole blood known in the art (e.g., and approved by one or more regulatory agencies and/or accrediting organizations). In some embodiments, the first container of a kit contains an anticoagulant prior to the transfer of a whole blood composition into the container (e.g., when collecting whole blood from a donor into the first container). In some embodiments, the anticoagulant is Citrate Phosphate Dextrose (CPD), Citrate Phosphate Double Dextrose (CP2D) or Citrate Phosphate Dextrose Adenine (LPDA-1). Suitable volumes of anticoagulant for mixing with whole blood (e.g., in a whole blood composition) are well known in the art, and in some embodiments may comprise for example about 30 mL to about 120 mL, about 50 mL to about 120 mL, about 60 mL to about 120 mL, about 50 mL to about 100 mL, about 50 mL to about 75 mL, about 60 mL to about 100 mL, about 60 mL to about 90 mL, about 60 mL to about 80 mL, or about 60 mL to about 70 mL. In some embodiments, an anticoagulant of the present disclosure comprises about 30 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 105 mL, about 110 mL, or about 120 mL.

In some embodiments, the kit further comprises a second container suitable for storing a pathogen-inactivated whole blood composition, wherein the second container comprises (e.g., includes) at least a first inlet and a first outlet. In some embodiments, the kit further comprises a conduit (e.g., third conduit) extending between the first outlet of the first container and the first inlet of the second container (e.g., and providing a fluid communication path for transferring (e.g., under sterile conditions) a mixture comprising a whole blood composition and a PIC (and quencher if present) from the first container into the second container). In some embodiments, the kit comprises a third container suitable for storing a pathogen-inactivated whole blood composition, wherein the third container comprises (e.g., includes) at least a first inlet and a first outlet, and the kit further comprises a conduit (e.g., fourth conduit) extending between the first outlet of the second container and the first inlet of the third container (e.g., and providing a fluid communication path for transferring (e.g., under sterile conditions) a mixture comprising a whole blood composition and a PIC (and quencher if present) from the second container into the third container).

Kits of the present disclosure may be used in conjunction with an infusion line (e.g., infusion line assembly, intravenous administration set) for infusing a pathogen-inactivated whole blood composition into a subject. In some embodiments, the kit comprises an infusion line assembly configured to be coupled (e.g., connected) to an outlet of a kit container (e.g., to a spike port). In some embodiments, the kit comprises an infusion line assembly coupled (e.g., connected) to an outlet of a kit container. In some embodiments, the infusion line assembly is coupled (e.g., connected) to an outlet of a kit container (e.g., to a spike port) after preparation of a pathogen-inactivated whole blood composition and before infusion. In some embodiments, the infusion line is connected to an outlet of a container (e.g., second container, third container) of the kit (e.g., before preparation of a pathogen-inactivated whole blood composition). In some embodiments, the infusion line assembly is integrally connected to an outlet of a container of the kit (e.g., before processing, during manufacturing of the kit). In some embodiments, the kit further comprises an infusion line assembly for infusing the pathogen-inactivated whole blood composition into a subject, wherein the infusion line comprises a second vascular access device (e.g., needle, infusion needle) and an infusion line conduit extending between the first container, the second container or the third container and the second vascular access device, wherein the infusion line conduit provides a fluid communication path for sterilely transferring the pathogen-inactivated whole blood composition from the container (e.g., first container, second container, third container) to the vascular access device (e.g., and into a donor accessed by the vascular access device). In some embodiments, the kit further comprises an infusion line assembly for infusing the pathogen-inactivated whole blood composition into a subject, wherein the infusion line assembly comprises a second vascular access device and an infusion line conduit extending between the first outlet of the second container and the second vascular access device, wherein the infusion line conduit provides a fluid communication path for sterilely transferring the pathogen-inactivated whole blood composition from the second container to the vascular access device. In some embodiments, the infusion line assembly provides an openable fluid communication path between a container (e.g., first, second, third) of the kit and a second vascular access device. An infusion line assembly as provided herein is generally suitable for administering or infusing (e.g., sterilely transferring) a pathogen-inactivated whole blood composition from a container of a kit to a subject in need of a whole blood infusion.

In another aspect, the present disclosure provides a kit for preparing a pathogen-inactivated whole blood composition, comprising: a first container suitable for mixing a whole blood composition, a pathogen inactivation compound (PIC) and a quencher, wherein the first container comprises (e.g., includes) at least a first inlet and a first outlet; a second container suitable for storing a pathogen-inactivated whole blood composition, wherein the second container comprises (e.g., includes) at least a first inlet and a first outlet, and wherein the second container is coupled to the first container; a container containing a pathogen inactivation compound (PIC container); a container containing a quencher (quencher container); a conduit, wherein the conduit at one end is coupled to or configured to be coupled to a PIC container and a quencher container, and wherein the conduit further comprises displacement device (e.g., an air displacement device) suitable for increasing the transfer of the PIC and the quencher through the first conduit. In some embodiments, the present disclosure provides a kit for preparing a pathogen-inactivated whole blood composition, comprising: (a) a first container suitable for mixing a whole blood composition, a pathogen inactivation compound (PIC) and a quencher, wherein the first container comprises (e.g., includes) at least a first inlet and a first outlet, (b) a second container suitable for storing a pathogen-inactivated whole blood composition, wherein the second container comprises (e.g., includes) at least a first inlet and a first outlet, (c) a container containing a pathogen inactivation compound (PIC container), (d) a container containing a quencher (quencher container), (e) a first conduit, wherein the first conduit at one end is coupled to or configured to be coupled to a PIC container and a quencher container, and wherein the first conduit further comprises displacement device (e.g., an air displacement device) suitable for increasing the transfer of the PIC and the quencher through the first conduit; and (f) a second conduit extending between the first container and the second container and providing a fluid communication path (e.g., openable fluid communication path) for transferring the whole blood composition from the first container to the second container.

In some embodiments, the first conduit further comprises at least one adaptor for coupling the second conduit to a PIC container and a quencher container. In some embodiments, the first conduit comprises a first adaptor for coupling a PIC container to the first conduit and a second adaptor for coupling a quencher container to the first conduit. In some embodiments, the first conduit is coupled to a PIC container and a quencher container. In some embodiments, the PIC container and the quencher container are the same container. In some embodiments, the first conduit is configured to be coupled to the first container, (e.g., providing a fluid communication path between the PIC container and quencher container and the first container). In some embodiments, the first conduit is configured to be coupled to an inlet of the first container. In some embodiments, the kit further comprises a vascular access device (e.g., needle) for drawing whole blood from a donor (e.g., by venipuncture), wherein the vascular access device is coupled to the first container (e.g., by way of a conduit extending between the vascular access device and container). In some embodiments, the kit comprises a conduit (e.g., third conduit) extending between the vascular access device and the first container, such as for example, the first inlet of the first container (e.g., and providing a fluid communication path for transferring the whole blood from the vascular access device into the first container). In some embodiments, the first container further comprises (e.g., includes) a second inlet, wherein the first conduit is configured to be coupled to the second inlet of the first container. In some embodiments, the first container further comprises (e.g., includes) a second inlet and the first conduit is coupled to the second inlet of the first container. In some embodiments, the first conduit is configured to be coupled to the third conduit, (e.g., providing a fluid communication path between the PIC container and quencher container and the first container). In some embodiments, the first container of the kit contains an anticoagulant (e.g., anticoagulant solution), such as for example, any suitable anticoagulant for use with whole blood known in the art (e.g., and approved by one or more regulatory agencies and/or accrediting organizations). In some embodiments, the first container of a kit contains an anticoagulant prior to the transfer of a whole blood composition into the container (e.g., when collecting whole blood from a donor into the first container). In some embodiments, the anticoagulant is Citrate Phosphate Dextrose (CPD), Citrate Phosphate Double Dextrose (CP2D) or Citrate Phosphate Dextrose Adenine (LPDA-1). Suitable volumes of anticoagulant for mixing with whole blood (e.g., in a whole blood composition) are well known in the art, and in some embodiments may comprise for example about 30 mL to about 120 mL, about 50 mL to about 120 mL, about 60 mL to about 120 mL, about 50 mL to about 100 mL, about 50 mL to about 75 mL, about 60 mL to about 100 mL, about 60 mL to about 90 mL, about 60 mL to about 80 mL, or about 60 mL to about 70 mL. In some embodiments, an anticoagulant of the present disclosure comprises about 30 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 105 mL, about 110 mL, or about 120 mL.

In some embodiments, the PIC comprises a functional group which is, or which forms, a reactive electrophilic group. In some embodiments, the functional group is selected from the group consisting of a mustard, a mustard intermediate, and a mustard equivalent. In some embodiments, the functional group is, or is capable of forming, an aziridinium ion. In some embodiments, the reactive electrophilic group is capable of reacting with nucleic acids. In some embodiments, the PIC comprises a nucleic acid binding ligand. In some embodiments, the nucleic acid binding ligand is an intercalator. In some embodiments, the intercalator is an acridine. In some embodiments, the PIC comprises a frangible linker linking the functional group and the nucleic acid binding ligand. In some embodiments, the PIC is β-alanine, N-(acridin-9-yl), 2-[bis(2-chloroethyl)amino] ethyl ester.

In some embodiments, the quencher comprises a thiol group, wherein the thiol is capable of reacting with a reactive electrophilic group of the pathogen inactivation compound. In some embodiments, the quencher comprises cysteine or a derivative of cysteine. In some embodiments, the quencher is glutathione or a pharmaceutically acceptable salt thereof. In some embodiments, the quencher is glutathione monosodium salt.

In some embodiments, the kit comprises a third container suitable for storing a pathogen-inactivated whole blood composition, wherein the third container comprises (e.g., includes) at least a first inlet and a first outlet, and wherein the third container is coupled to the second container. In some embodiments, the kit further comprises a fourth conduit extending between the first outlet of the second container and the first inlet of the third container (e.g., and providing a fluid communication path for transferring (e.g., under sterile conditions) the whole blood composition from the second container into the third container). In some embodiments, the kit further comprises an infusion line assembly for infusing the pathogen-inactivated whole blood composition into a subject, wherein the infusion line assembly comprises a second vascular access device and an infusion line conduit extending between the first outlet (e.g., spike port) of the second container and the second vascular access device, (e.g., wherein the infusion line conduit provides a fluid communication path for sterilely transferring the pathogen-inactivated whole blood composition from the second container to the vascular access device). In some embodiments, the kit further comprises an infusion line assembly for infusing the pathogen-inactivated whole blood composition into a subject, wherein the infusion line assembly comprises a second vascular access device and an infusion line conduit extending between the first outlet (e.g., spike port) of the third container and the second vascular access device, (e.g., wherein the infusion line conduit provides a fluid communication path for sterilely transferring the pathogen-inactivated whole blood composition from the third container to the vascular access device).

In some embodiments, a kit of the present disclosure further comprises any one or more of detachable clamps, frangible connectors, in-line filters, and or sampling containers (e.g., sampling pouch, diversion pouch).

Non-limiting examples of exemplary kits for preparing a pathogen-inactivated whole blood composition according to the methods disclosed herein are illustrated in FIGS. 1a-1c, 2a-2g, 3a-3c, 4a-4d and 5a-5g.

The exemplary kit 100 shown in FIG. 1a comprises (e.g., includes): a first container 105 suitable for mixing a whole blood composition, a pathogen inactivation compound (PIC) and optionally a quencher, wherein the first container comprises a first inlet 110 and a first outlet 115; a container 120 containing a pathogen inactivation compound (PIC container); a container containing a quencher 125 (quencher container); a conduit 130 configured for coupling the PIC container 120 and the quencher container 125 to the first container 105; and an optional infusion line assembly 145 (e.g., configured to be coupled to the first outlet 115 of the first container 105) for infusing a pathogen-inactivated whole blood composition into a subject. In some embodiments, the conduit 130 comprises at one end (e.g., via a 2-way conduit branch): (a) a first adaptor 135 for coupling (e.g., configured to be coupled to) the PIC container to the conduit, and (b) a second adaptor 140 for coupling (e.g., configured to be coupled to) the quencher container to the conduit, and wherein the conduit is configured to be coupled to the first inlet 110 of the first container. In some embodiments, conduit 130 is configured to be coupled directly to the first inlet 110. In some embodiments, conduit 130 is configured to be coupled to the first inlet 110 by way of coupling to an optional conduit 142 (e.g., conduit 142 extending from first inlet 110). In some embodiments, optional infusion line assembly 145 is configured to be coupled to the first container 105 (e.g., first outlet 115 of the first container; by way of spike port). The dashed lines indicate that, in some embodiments, a whole blood (WB) composition may be provided to kit 100 from or in a blood collection container 150 and may be added into the first container 105 of the kit 100 by coupling (e.g., sterile docking) the blood collection container (e.g., tubing 152 extending from the blood collection container) to the first inlet 110 of the first container 105 (e.g., coupling directly to first inlet 110, coupling by way of a conduit 142 extending from first inlet 110). In some embodiments, the blood collection container (150) may be coupled to the first container (105) (e.g., directly or to conduit 142) to permit transfer of the whole blood into the first container, followed by disconnecting the blood collection container (150) from the first container (105), such as for example using a tube welder, and coupling of the conduit (130) to the first container (105) (e.g., directly or to conduit 142) to permit transfer of the pathogen inactivation compound and quencher to the first container (105).

Figure 1B:
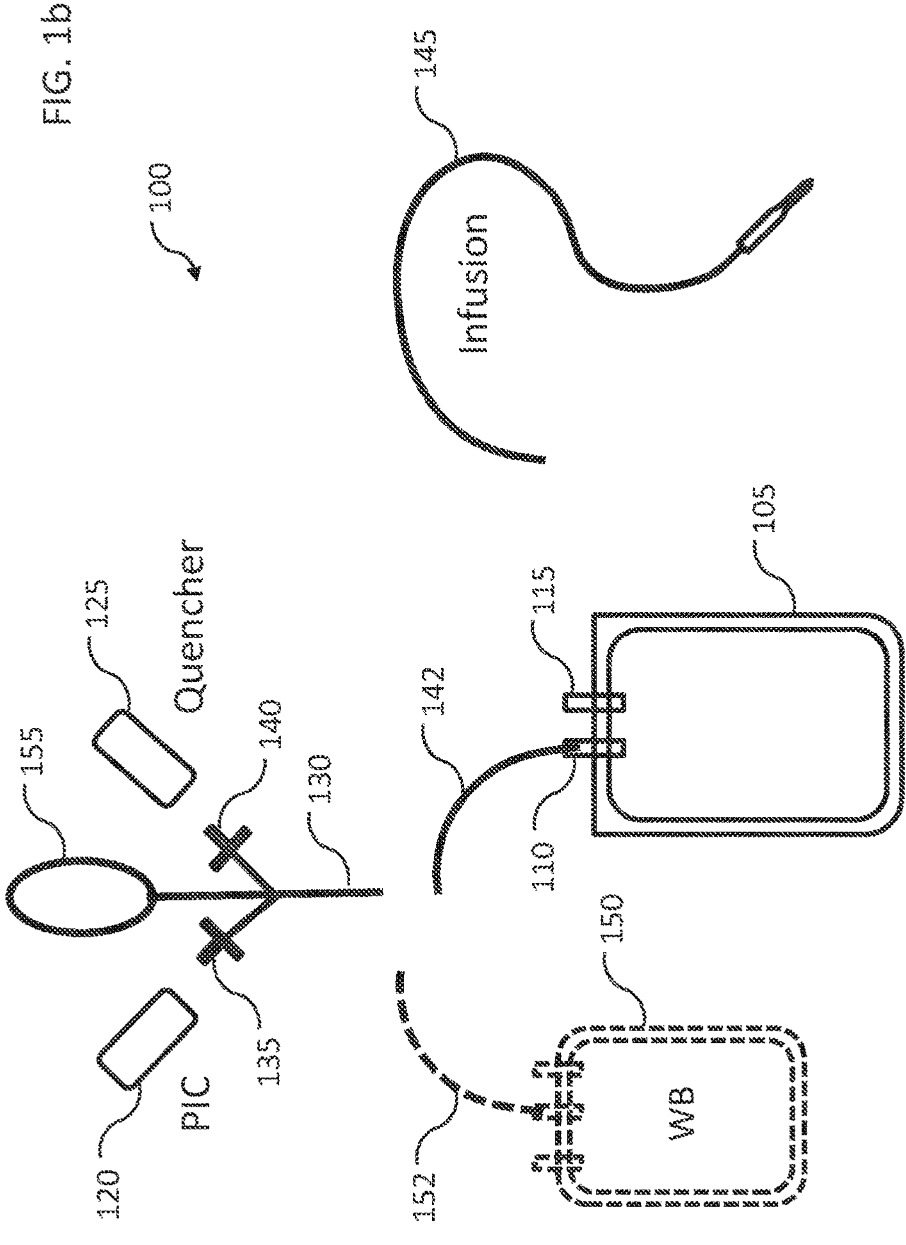
FIG. 1*b* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 1b. Similar to FIG. 1a, exemplary kit 100 comprises a first container 105 comprising a first inlet 110 and a first outlet 115; a PIC container 120; a quencher container 125; a conduit 130 configured for coupling the PIC container 120 and the quencher container 125 to the first container 105; an optional infusion line assembly 145; and optionally at one end of conduit 130 (e.g., via a conduit branch): (a) a first adaptor 135 for coupling the PIC container to the conduit, and (b) a second adaptor 140 for coupling the quencher container to the conduit. This configuration further comprises displacement device (e.g., an air displacement device) 155 suitable for improving (e.g., increasing) the transfer of the PIC and the quencher into container 105 (e.g., through the conduit 130 and into container 105). In some embodiments, the displacement device (e.g., air displacement device) 155 is coupled to the conduit 130 (e.g., via a 3-way conduit branch) at the end of the conduit comprising the first 135 and second 140 adaptors for coupling the PIC and quencher containers, 120 and 125 respectively. Non-limiting examples of displacement devices for use in the kits and methods of the present disclosure include a sampling pouch, diversion pouch, air cushion, bulb, syringe barrel, fluid (e.g., saline) containing container and the like. Dashed lines indicate that a whole blood (WB) composition may be provided to kit 100 by way of a blood collection container 150.

Figure 1C:
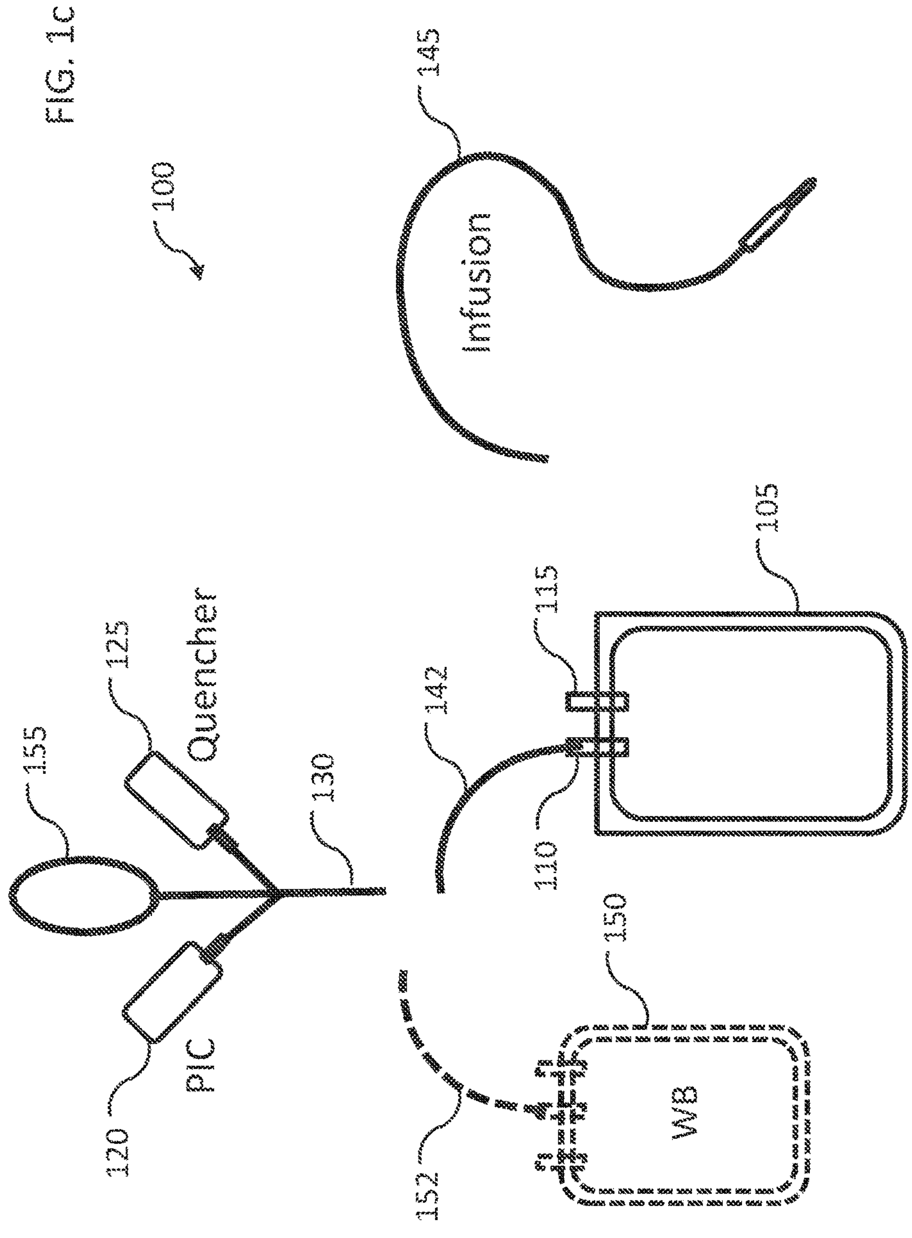
FIG. 1*c* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 1*c*. Similar to FIG. 1*b*, exemplary kit 100 comprises a first container 105 comprising a first inlet 110 and a first outlet 115; a PIC container 120; a quencher container 125; a displacement device (e.g., air displacement device) 155; a conduit 130 configured for coupling the PIC container 120 and the quencher container 125 to the first container 105; and an optional infusion line assembly 145. This configuration comprises at one end of the conduit 130 (e.g., via a conduit branch), the PIC container 120 coupled to the conduit, the quencher container 125 coupled to the conduit, and the displacement device (e.g., air displacement device) 155 coupled to the conduit suitable for improving (e.g., increasing) the transfer of the PIC and the quencher into container 105 (e.g., through the conduit 130 and into container 105). Dashed lines indicate that a whole blood (WB) composition may be provided to kit 100 by way of a blood collection container 150.

Figure 2A:
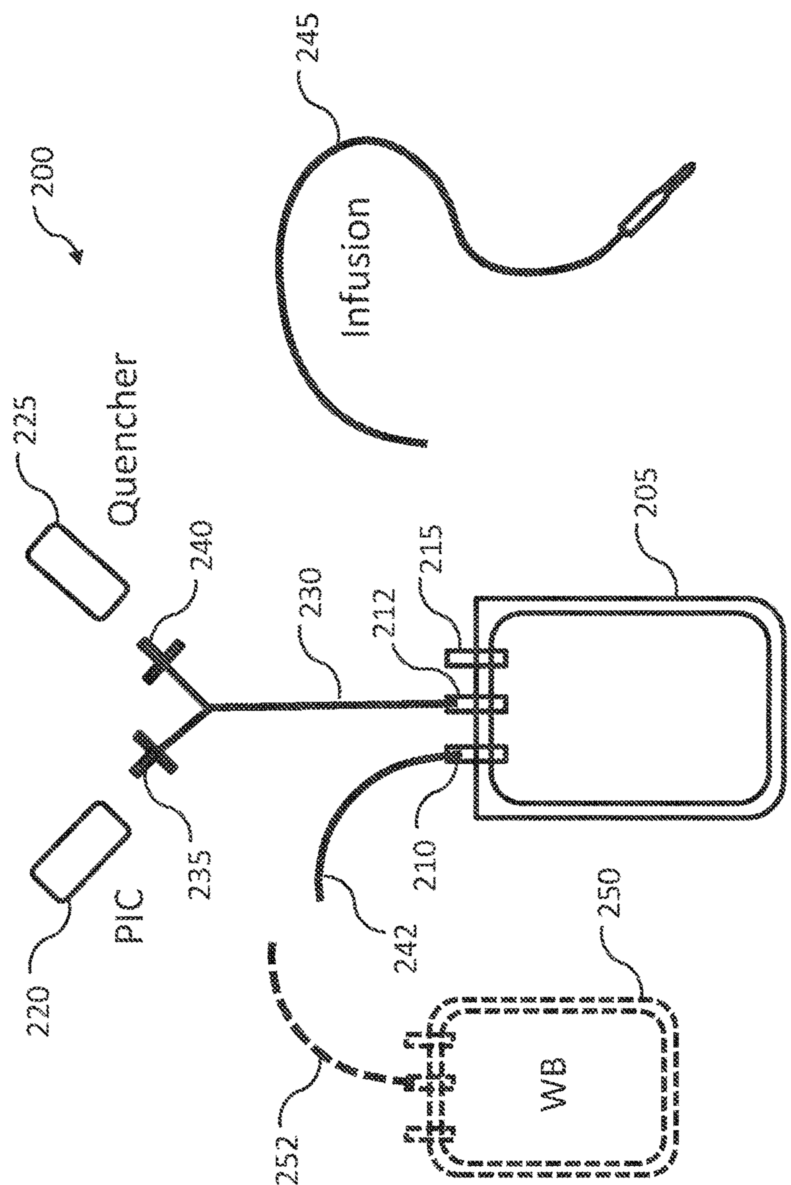
FIG. 2*a* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

The exemplary kit 200 shown in FIG. 2*a* comprises (e.g., includes): a first container 205 suitable for mixing a whole blood composition, a pathogen inactivation compound (PIC) and optionally a quencher, wherein the first container 205 comprises a first inlet 210, a second inlet 212, and a first outlet 215; a container 220 containing a pathogen inactivation compound (PIC container); a container 225 containing a quencher (quencher container); a conduit 230 coupled at one end to the first container 205 (e.g., second inlet 212 of first container 205) and configured at the other end for coupling the PIC container 220 and the quencher container 225 (e.g., to provide a fluid communication path between the first container and the PIC and quencher containers 220 and 225, respectively); and an optional infusion line assembly 245 for infusing a pathogen-inactivated whole blood composition into a subject. In some embodiments, conduit 230 comprises at one end (e.g., via a 2-way conduit branch): (a) a first adaptor 235 for coupling (e.g., configured to be coupled to) the PIC container to the conduit 230, and (b) a second adaptor 240 for coupling (e.g., configured to be coupled to) the quencher container to the conduit 230, and wherein the conduit (e.g., at the other end) is coupled to the second inlet 212 of the first container 205. In some embodiments, the infusion line assembly 245 is configured to be coupled to the first container 205 (e.g., first outlet 215 of the first container; by way of a spike port). The dashed lines indicate that a whole blood (WB) composition may be provided to kit 200 from or in a blood collection container 250 and may be added into the first container 205 of the kit 200 by coupling (e.g., sterile docking) the blood collection container (e.g., tubing 252 extending from the blood collection container) to the first inlet 210 of the first container 205 (e.g., coupling directly to first inlet 210, coupling by way of a conduit 242 extending from first inlet 210).

Figure 2B:
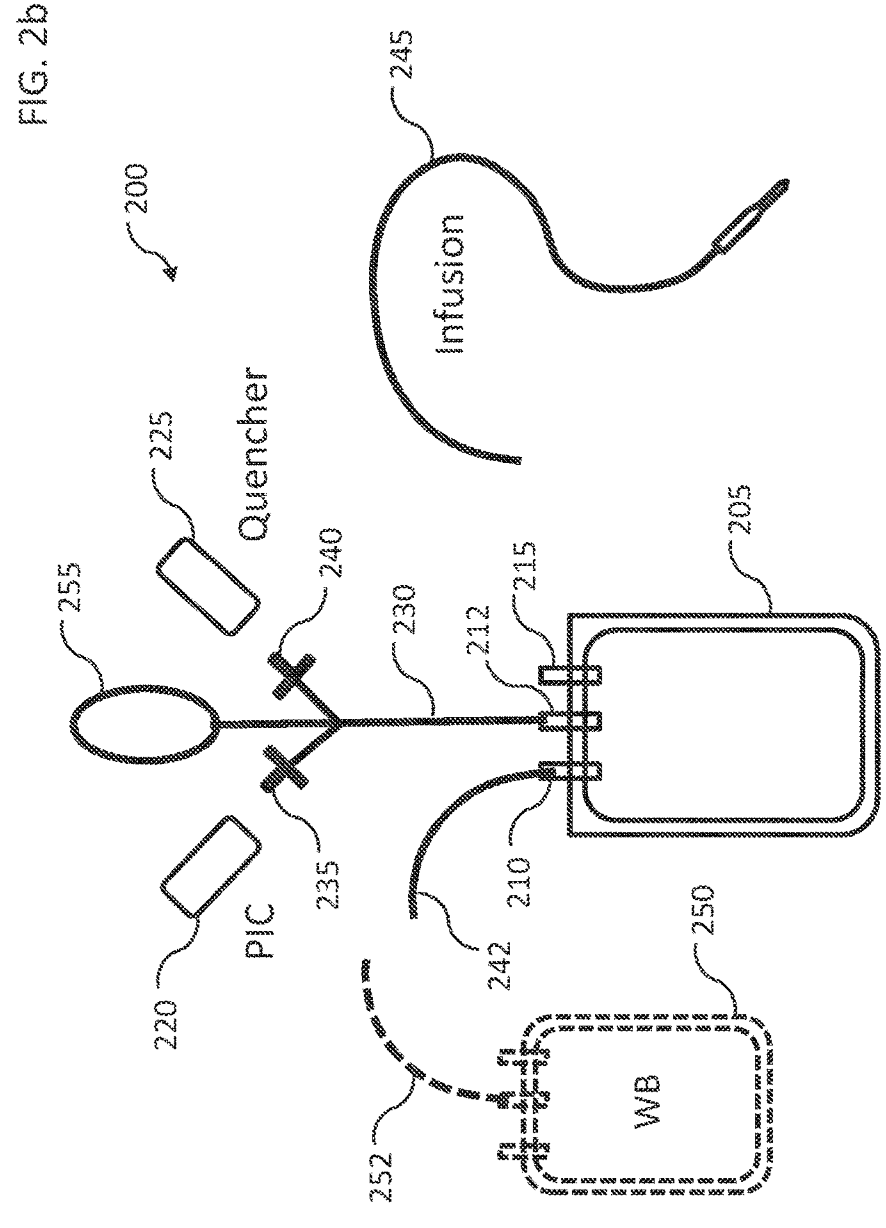
FIG. 2*b* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 2*b*. Similar to FIG. 2*a*, exemplary kit 200 comprises a first container 205 comprising a first inlet 210, a second inlet 212, and a first outlet 215; a PIC container 220; a quencher container 225; a conduit 230 coupled at one end to the first container 205 and configured at the other end for coupling the PIC container 220 and the quencher container 225; an optional infusion line assembly 245; and optionally at one end of conduit 230 (e.g., via a conduit branch): (a) a first adaptor 235 for coupling the PIC container to the conduit, and (b) a second adaptor 240 for coupling the quencher container to the conduit. This configuration further comprises a displacement device (e.g., an air displacement device) 255 suitable for improving (e.g., increasing) the transfer of the PIC and the quencher into container 205 (e.g., through the conduit 230 and into container 205). In some embodiments, the displacement device (e.g., air displacement device) 255 is coupled to the conduit 230 (e.g., via a 3-way conduit branch) at the end of the conduit comprising the first 235 and second 240 adaptors for coupling the PIC and quencher containers, 220 and 225 respectively. Dashed lines indicate that a whole blood (WB) composition may be provided to kit 200 by way of a blood collection container 250.

Figure 2C:
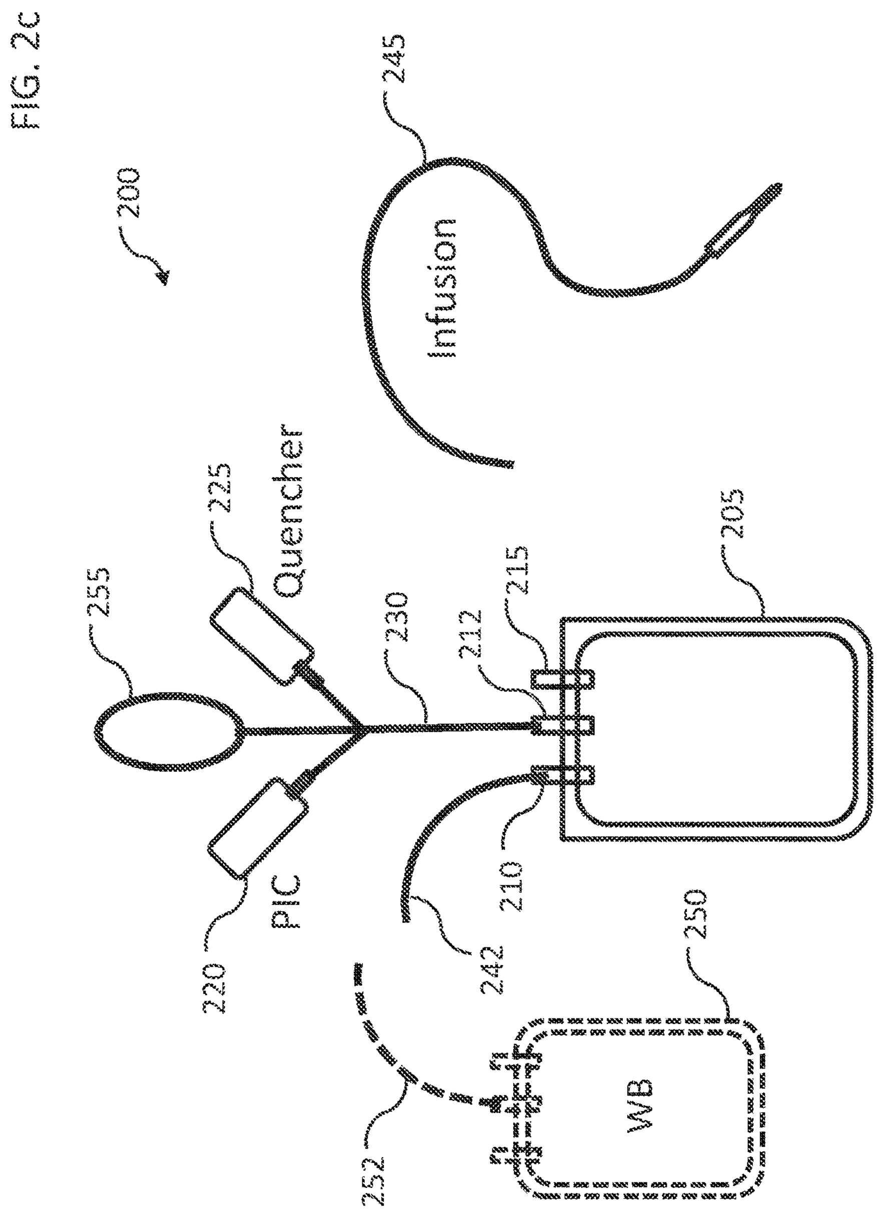
FIG. 2*c* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 2*c*. Similar to FIG. 2*b*, exemplary kit 200 comprises a first container 205 comprising a first inlet 210, a second inlet 212, and a first outlet 215; a PIC container 220; a quencher container 225; a displacement device (e.g., an air displacement device) 255; a conduit 230 coupling (e.g., and providing a fluid communication path between) the first container 205 and the PIC container 220 and quencher container 225; and an optional infusion line assembly 245. This configuration comprises at one end of the conduit 230 (e.g., via a conduit branch), the PIC container 220 coupled to the conduit, the quencher container 225 coupled to the conduit, and the displacement device (e.g., air displacement device) 255 coupled to the conduit suitable for improving (e.g., increasing) the transfer of the PIC and the quencher into container 205 (e.g., through the conduit 230 and into container 205). Dashed lines indicate that a whole blood (WB) composition may be provided to kit 200 by way of a blood collection container 250.

Figure 2D:
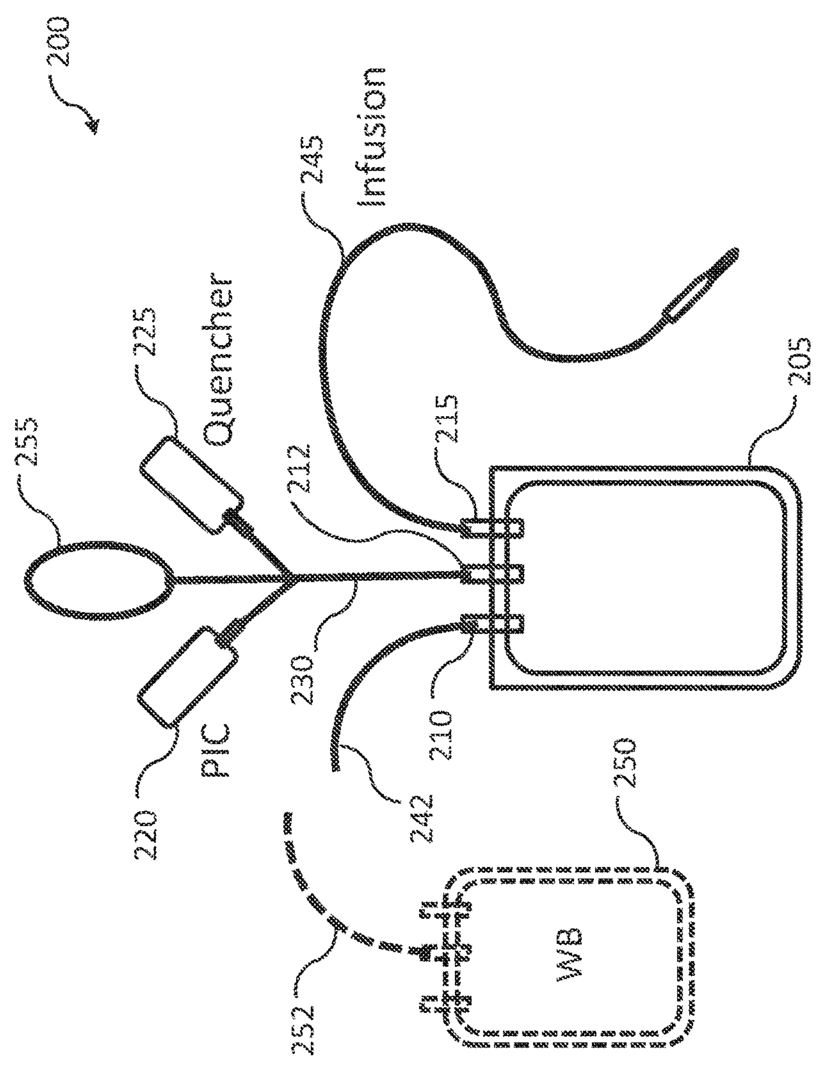
FIG. 2*d* shows an exemplary kit for use in preparing a pathogen inactivated whole blood composition in accordance with some embodiments. Dotted components depict a source container with whole blood (e.g., whole blood composition) for connecting to the kit. Abbreviations: PIC, pathogen inactivation compound; WB, whole blood. Drawing not to scale.

An alternative configuration for an exemplary kit of the disclosure is shown in FIG. 2*d*. Similar to FIG. 2*c*, exemplary kit 200 comprises a first container 205 comprising a first inlet 210, a second inlet 212, and a first outlet 215; a PIC container 220; a quencher container 225; a displacement device 255; and a conduit 230 coupling (e.g., and providing a fluid communication path between) the first container 205 and the PIC container 220 and quencher container 225. This configuration further comprises an infusion line assembly 245, wherein the infusion line assembly is coupled to the first container 205 (e.g., coupled to first outlet 215). Dashed lines indicate that a whole blood (WB) composition may be provided to kit 200 by way of a blood collection container 250.

Figure 2E:
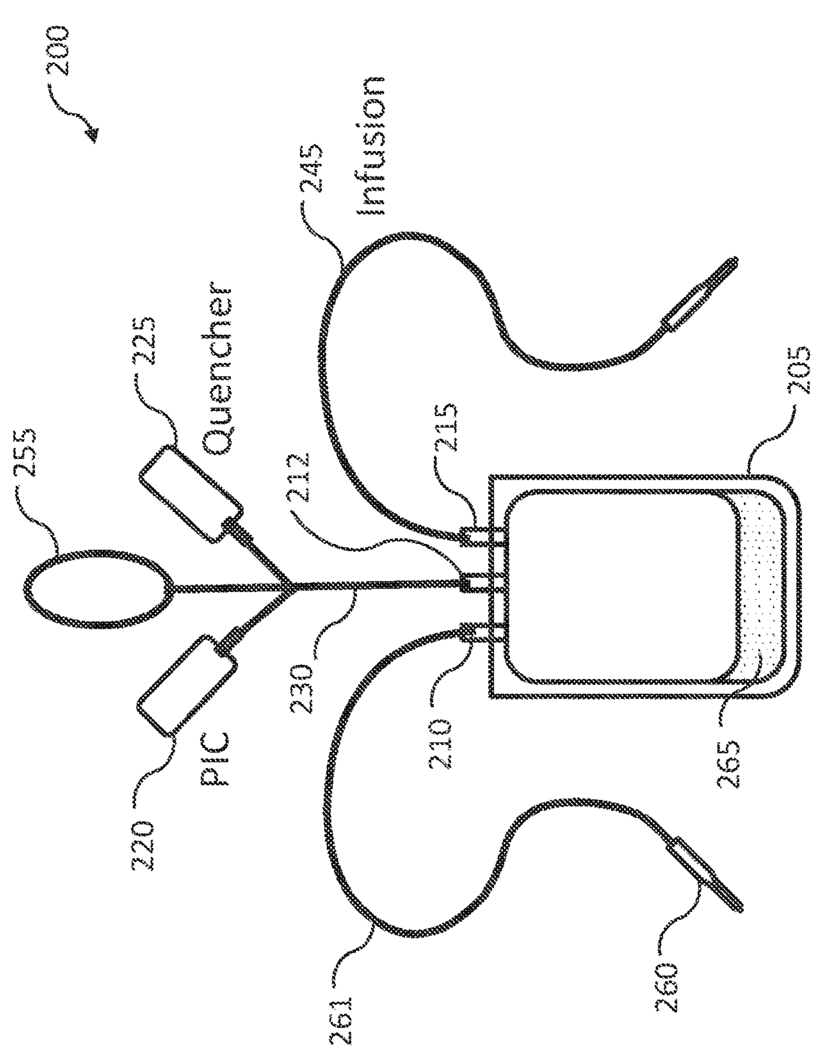
FIG. 2*e* shows an exemplary kit for use in preparing a pathogen inactivated whole blood composition in accordance with some embodiments. Abbreviations: PIC, pathogen inactivation compound. Drawing not to scale.

An alternative configuration for an exemplary kit of the disclosure is shown in FIG. 2*e*. Similar to FIG. 2*d*, exemplary kit 200 comprises a first container 205 comprising a first inlet 210, a second inlet 212, and a first outlet 215; a PIC container 220; a quencher container 225; a displacement device 255; a conduit 230 coupling (e.g., and providing a fluid communication path between) the first container 205 and the PIC container 220 and quencher container 225; and an infusion line assembly 245. This configuration further comprises a vascular access device 260 for drawing whole blood from a donor (e.g., into container 205); and a conduit 261 extending between the vascular access device 260 and the first inlet 210 of the first container. In some embodiments, the vascular access device 260 and conduit 261 together comprise a needle assembly. In some embodiments, container 205 contains an anticoagulant (e.g., anticoagulant solution) 265.

Figure 2F:
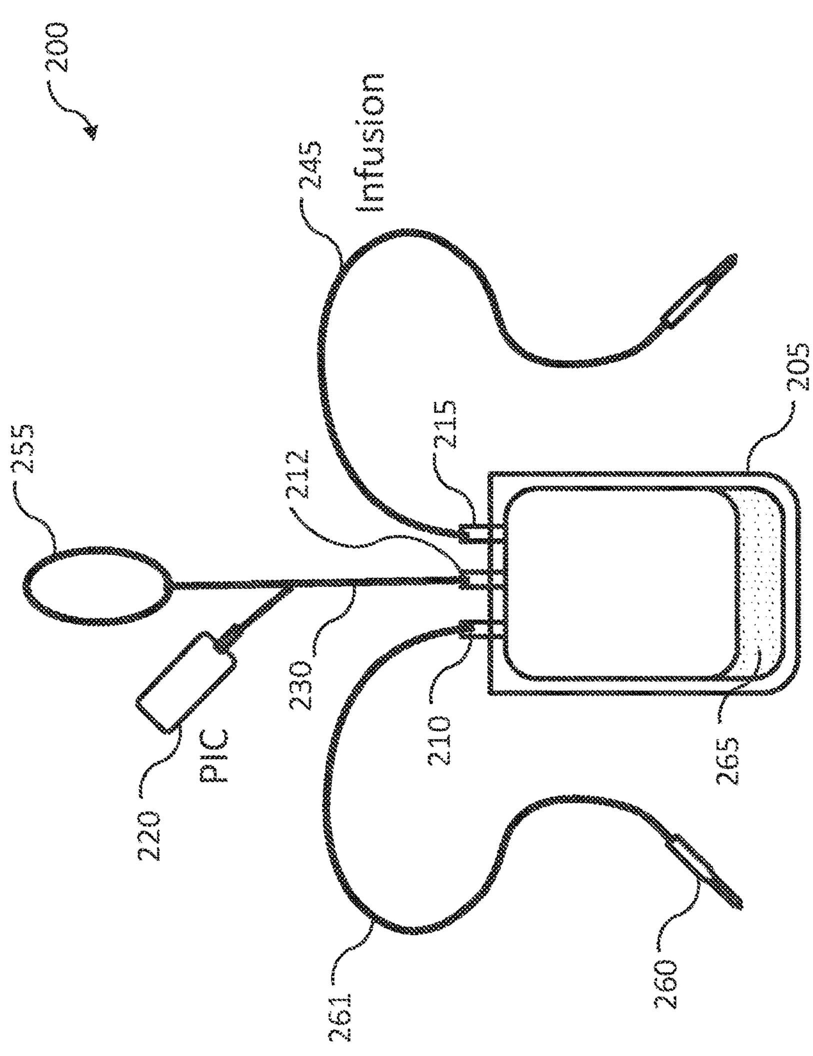
FIG. 2*f* shows an exemplary kit for use in preparing a pathogen inactivated whole blood composition in accordance with some embodiments. Abbreviations: PIC, pathogen inactivation compound; WB, whole blood. Drawing not to scale.

An alternative configuration for an exemplary kit of the disclosure is shown in FIG. 2*f*. Similar to FIG. 2*e*, exemplary kit 200 comprises a first container 205 comprising a first inlet 210, a second inlet 212, and a first outlet 215; a PIC container 220; a displacement device 255; a conduit 230 coupling (e.g., and providing a fluid communication path between) the first container 205 and the PIC container 220; an infusion line assembly 245; a vascular access device 260;

and a conduit 261. In some embodiments, container 205 contains an anticoagulant 265.

Figure 2G:
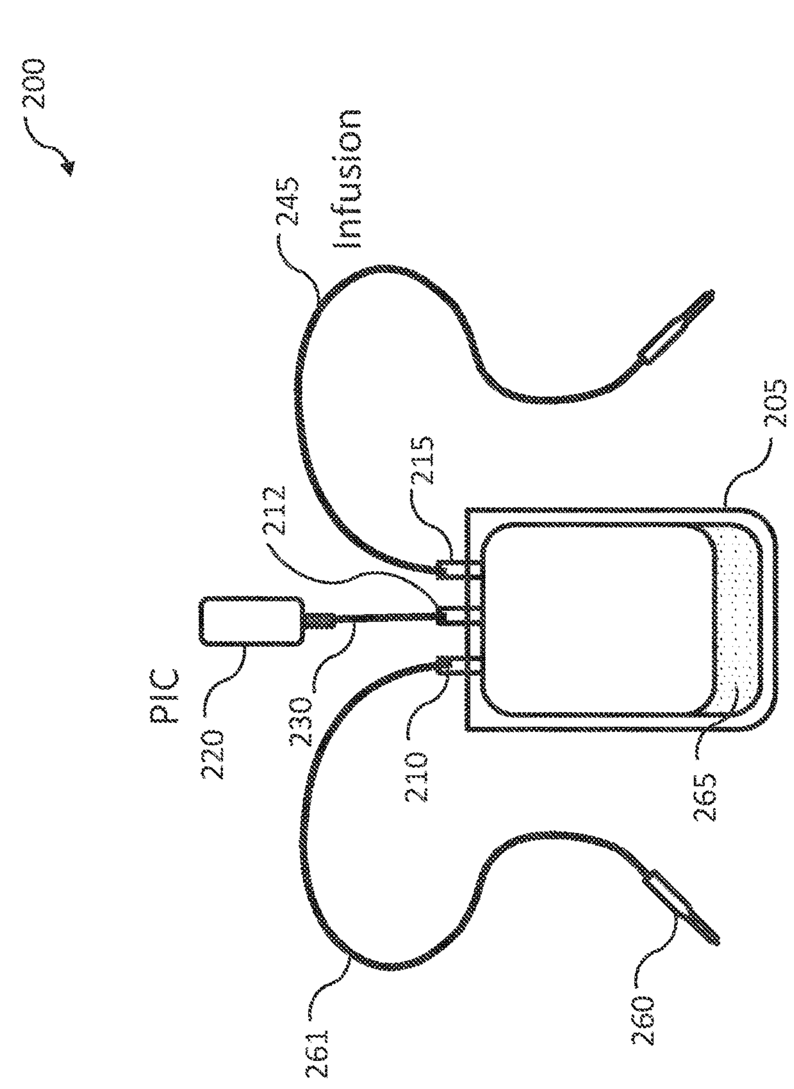
FIG. 2*g* shows an exemplary kit for use in preparing a pathogen inactivated whole blood composition in accordance with some embodiments. Abbreviations: PIC, pathogen inactivation compound. Drawing not to scale.

An alternative configuration for an exemplary kit of the disclosure is shown in FIG. 2*g*. Similar to FIG. 2*f*, exemplary kit 200 comprises a first container 205 comprising a first inlet 210, a second inlet 212, and a first outlet 215; a PIC container 220; a conduit 230 coupling (e.g., and providing a fluid communication path between) the first container 205 and the PIC container 220; an infusion line assembly 245; a vascular access device 260; and a conduit 261. In some embodiments, container 205 contains an anticoagulant 265.

Figure 3A:
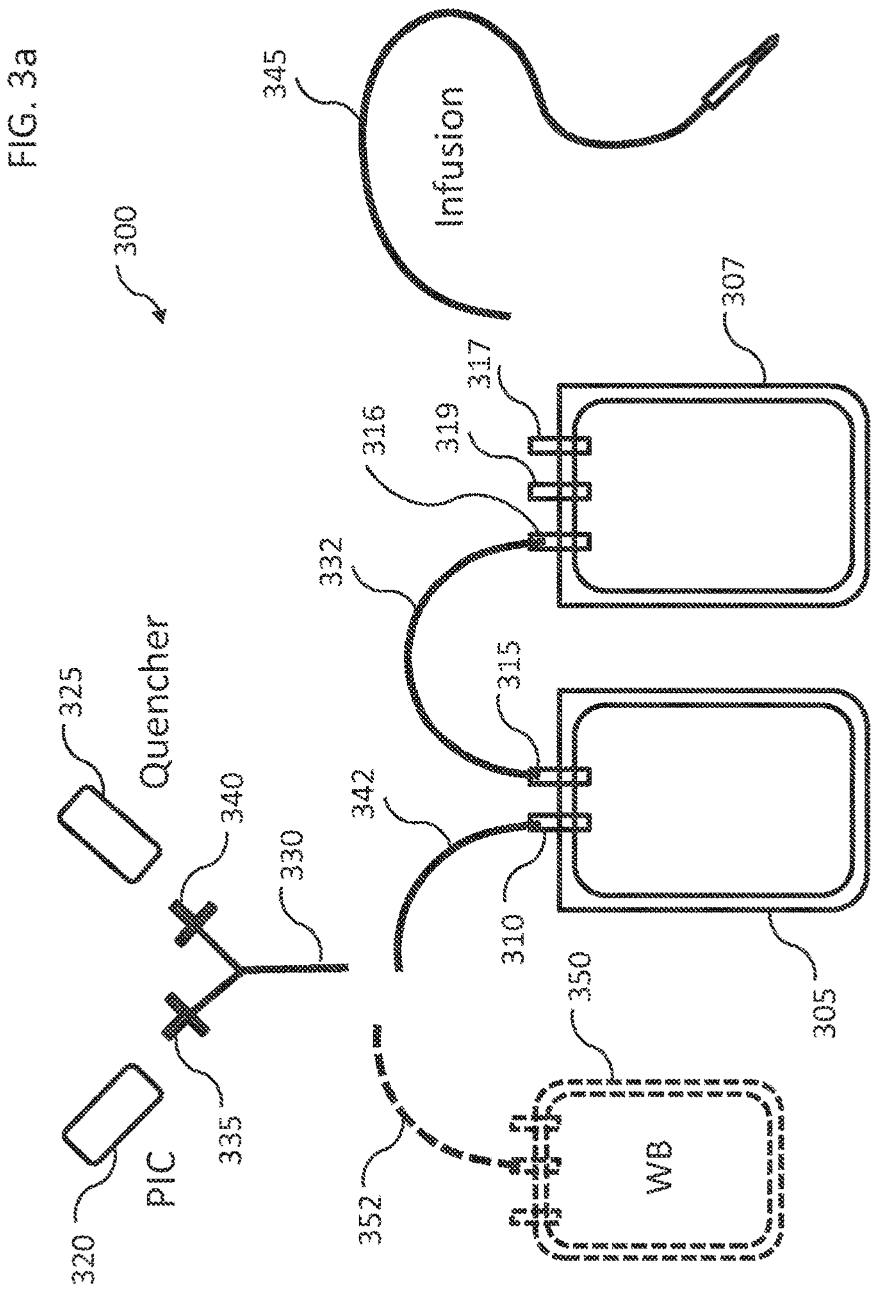
FIG. 3*a* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

The exemplary kit 300 shown in FIG. 3*a* comprises (e.g., includes): a first container 305 suitable for mixing a whole blood composition, a pathogen inactivation compound (PIC) and optionally a quencher, wherein the first container comprises a first inlet 310 and a first outlet 315; a second container 307 suitable for storing a pathogen-inactivated whole blood composition, wherein the second container 307 comprises a first inlet 316 and a first outlet 317, and an optional second outlet 319 (e.g., coupled to or configured to be coupled to a diversion pouch); a container 320 containing a pathogen inactivation compound (PIC container); a container 325 containing a quencher (quencher container); a conduit 330 configured for coupling the PIC container 320 and the quencher container 325 to the first container 305; a conduit 332 coupling the first container 305 and the second container 307, and an optional infusion line assembly 345 for infusing a pathogen-inactivated whole blood composition into a subject. In some embodiments, conduit 330 comprises at one end (e.g., via a 2-way conduit branch): (a) a first adaptor 335 for coupling (e.g., configured to be coupled to) the PIC container to the conduit, (b) a second adaptor 340 for coupling (e.g., configured to be coupled to) the quencher container to the conduit, and wherein the conduit is configured to be coupled to the first inlet 310 of the first container. In some embodiments, conduit 330 is configured to be directly coupled to the first inlet 310 of container 305. In some embodiments, conduit 330 is configured to be coupled to the first inlet 310 by way of coupling to an optional conduit 342 (e.g., conduit 342 extending from first inlet 310 of container 305). In some embodiments, optional infusion line assembly 345 is configured to be coupled to the second container 307 (e.g., first outlet 317 of the second container; by way of a spike port). The dashed lines indicate that a whole blood (WB) composition may be provided to kit 300 from or in a blood collection container 350 and may be added into the first container 305 of kit 300 by coupling (e.g., sterile docking) the blood collection container (e.g., tubing 352 extending from the blood collection container) to the first inlet 310 of the first container 305 (e.g., coupling directly to the first inlet 310, coupling by way of a conduit 342 extending from first inlet 310). In some embodiments, blood collection container 350 may be coupled to the first container 305 to permit transfer of the whole blood into the first container 305, followed by disconnecting the blood collection container 350 from the first container 305, such as for example using a tubing welder, and coupling of the conduit 330 to the first container 305 (e.g., coupling directly to first inlet 310, coupling by way of a conduit 342 extending from first inlet 310) to permit transfer of the pathogen inactivation compound and quencher to the first container 305.

Figure 3B:
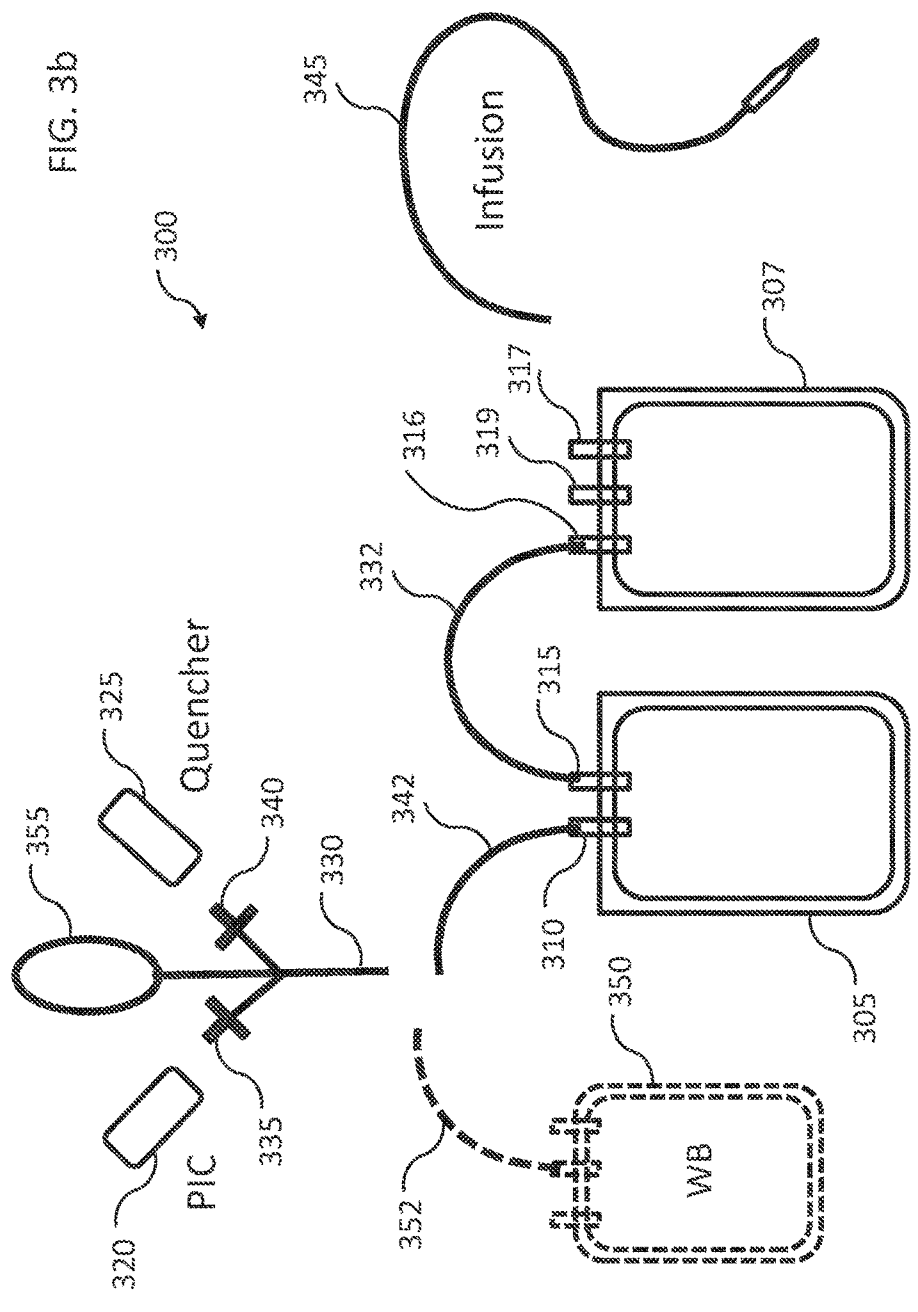
FIG. 3*b* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 3*b*. Similar to FIG. 3*a*, exemplary kit 300 comprises a first container 305 comprising a first inlet 310 and a first outlet 315; a PIC container 320; a quencher container 325; a conduit 330 configured for coupling the PIC container 320 and the quencher container 325 to the first container 305; a second container 307 comprising a first inlet 316, a first outlet 317, and an optional second outlet 319; a conduit 332; an optional infusion line assembly 345; and optionally at one end of conduit 330 (e.g., via a conduit branch): (a) a first adaptor 335 for coupling the PIC container to the conduit, and (b) a second adaptor 340 for coupling the quencher container to the conduit. This configuration further comprises a displacement device (e.g., an air displacement device) 355 suitable for improving (e.g., increasing) the transfer of the PIC and the quencher into container 305 (e.g., through the conduit 330 and into container 305). In some embodiments, the displacement device (e.g., air displacement device) 355 is coupled to the conduit 330 (e.g., via a 3-way conduit branch) at the end of the conduit comprising the first 335 and second 340 adaptors for coupling the PIC and quencher containers, 320 and 325 respectively. Dashed lines indicate that a whole blood (WB) composition may be provided to kit 300 by way of a blood collection container 350.

Figure 3C:
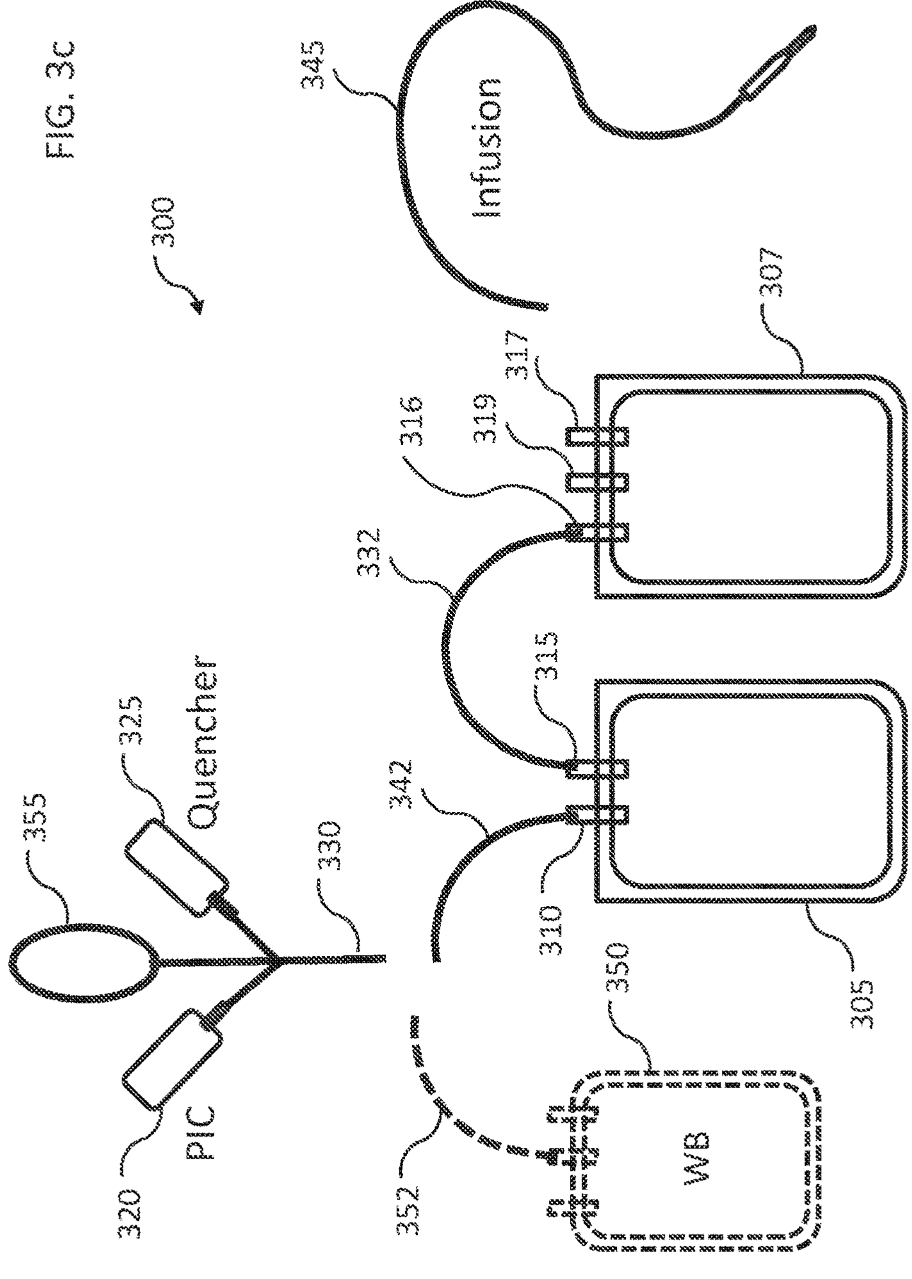
FIG. 3*c* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 3*c*. Similar to FIG. 3*b*, exemplary kit 300 comprises a first container 305 comprising a first inlet 310 and a first outlet 315; a PIC container 320; a quencher container 325; a conduit 330 configured for coupling the PIC container 320 and the quencher container 325 to the first container 305; a displacement device (e.g., air displacement device) 355; a second container 307 comprising a first inlet 316, a first outlet 317, and an optional second outlet 319; a conduit 332; and an optional infusion line assembly 345. This configuration comprises at one end of the conduit 330 (e.g., via conduit branch), the PIC container 320 coupled to the conduit, the quencher container 325 coupled to the conduit, and the displacement device (e.g., air displacement device) 355 coupled to the conduit suitable for improving (e.g., increasing) the transfer of the PIC and the quencher into container 305 (e.g., through the conduit 330 and into container 305). Dashed lines indicate that a whole blood (WB) composition may be provided to kit 300 by way of a blood collection container 350.

Figure 4A:
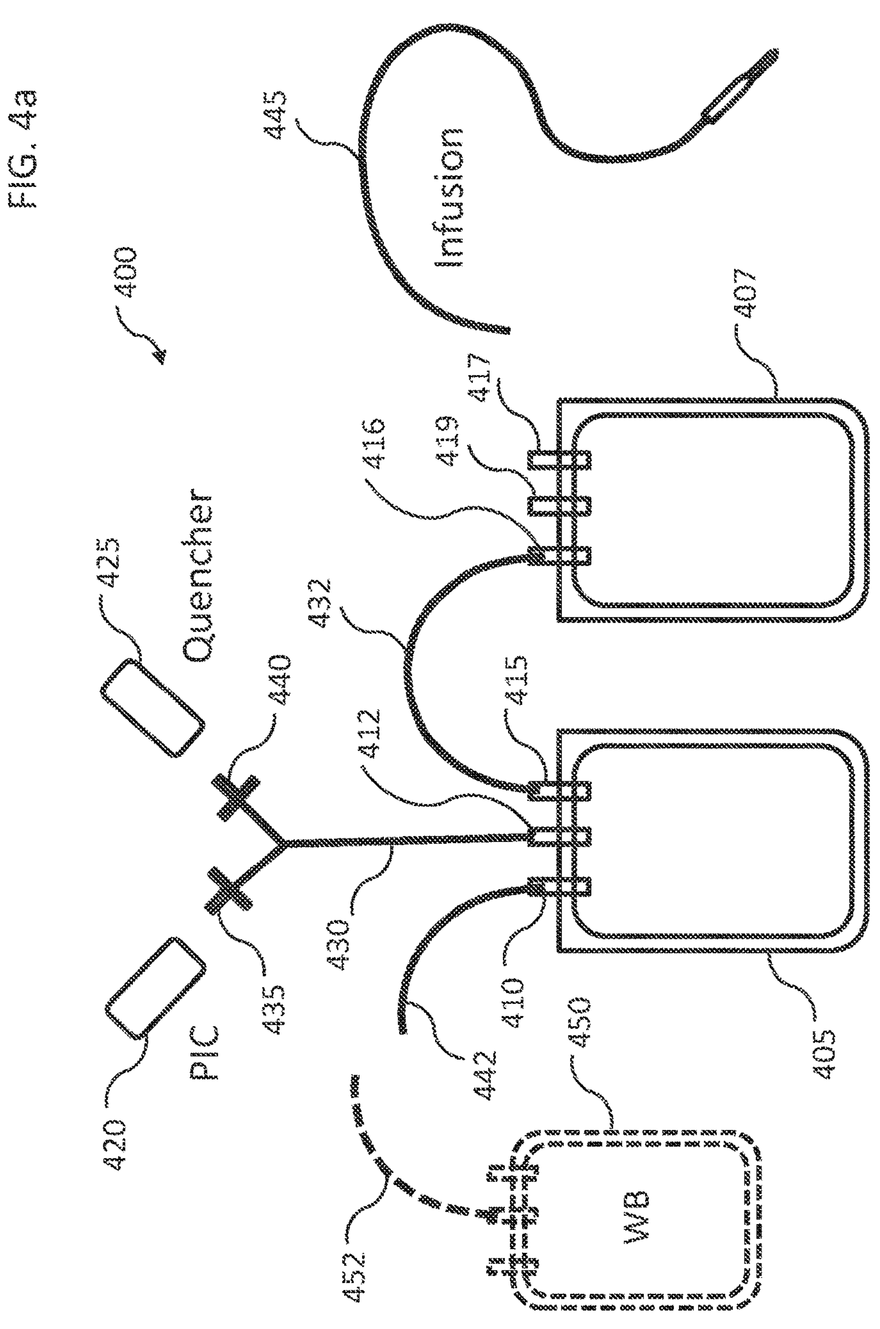
FIG. 4*a* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

The exemplary kit 400 shown in FIG. 4*a* comprises (e.g., includes): a first container 405 suitable for mixing a whole blood composition, a pathogen inactivation compound (PIC) and optionally a quencher, wherein the first container 405 comprises a first inlet 410, a second inlet 412, and a first outlet 415; a second container 407 suitable for storing a pathogen-inactivated whole blood composition, wherein the second container comprises a first inlet 416 and a first outlet 417, and an optional second outlet 419 (e.g., coupled to or configured to be coupled to a diversion pouch); a container 420 containing a pathogen inactivation compound (PIC container); a container 425 containing a quencher (quencher container); a conduit 430 coupled at one end to the first container 405 (e.g., second inlet 412 of first container 405) and configured at the other end for coupling the PIC container 420 and the quencher container 425 (e.g., to provide a fluid communication path between the first container 405 and the PIC and quencher containers 420 and 425, respectively; a conduit 432 coupling the first container 405 and the second container 407; and an optional infusion line assembly 445 for infusing a pathogen-inactivated whole blood composition into a subject. In some embodiments, conduit 430 comprises at one end (e.g., via a 2-way conduit branch): (a) a first adaptor 435 for coupling (e.g., configured to be coupled to) the PIC container 420 to the conduit, (b) a second adaptor 440 for coupling (e.g., configured to be coupled to) the quencher container 425 to the conduit, wherein the conduit (e.g., at the other end) is coupled to the second inlet 412 of the first container 405. In some embodiments, the infusion line assembly 445 is configured to be coupled to the second container 407 (e.g., first outlet 417 of the second container; by way of a spike port). The dashed lines indicate that a whole blood (WB) composition may be provided to kit 400 from or in a blood collection container 450 may be added into the first container 405 of kit 400 by coupling (e.g., sterile docking) the blood collection container (e.g., tubing 452 extending from the blood collection container) to the first inlet 410 of the first container 405 (e.g., coupling directly to first inlet 410, coupling by way of a conduit 442 extending from the first inlet 410).

Figure 4B:
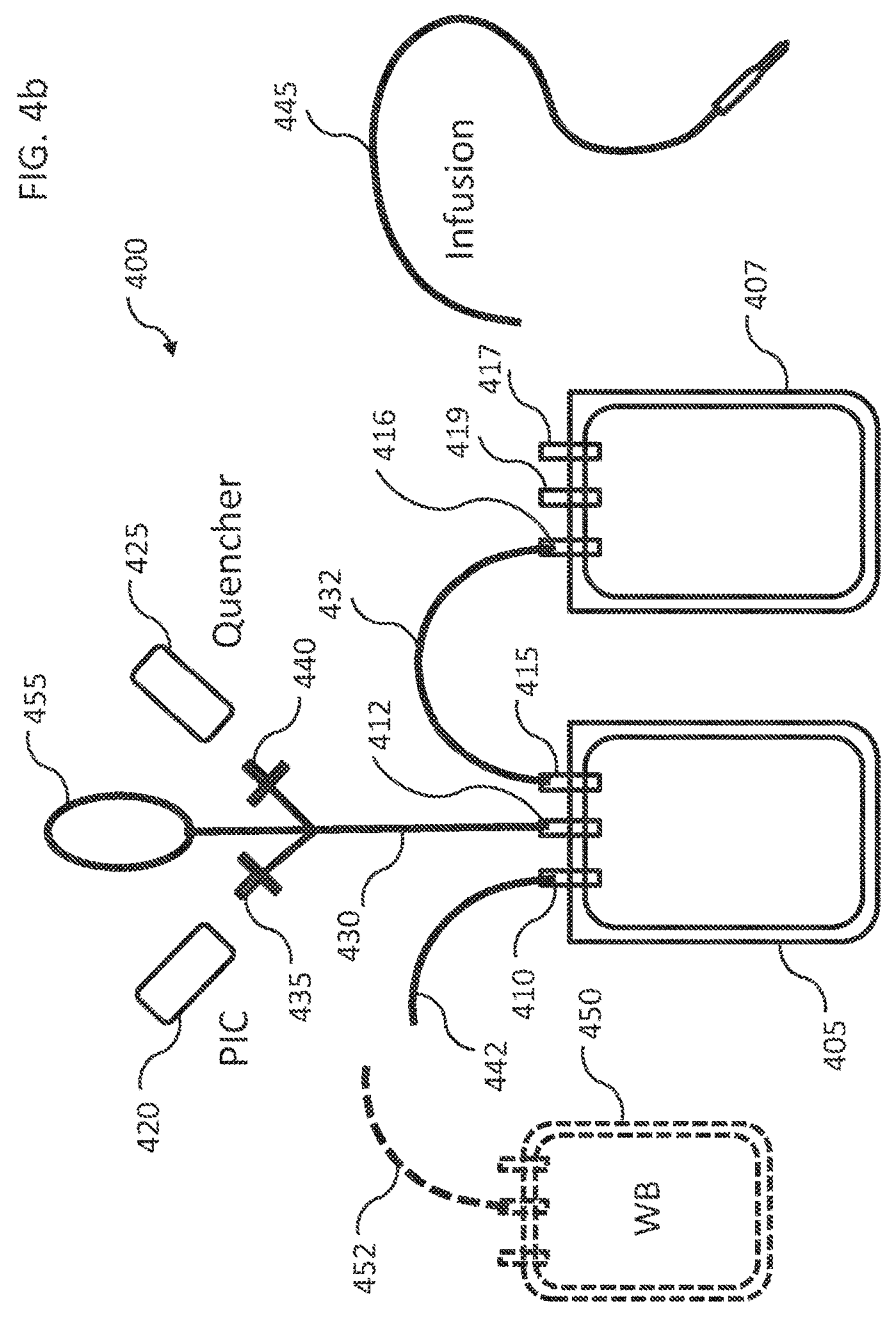
FIG. 4*b* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 4*b*. Similar to FIG. 4*a*, exemplary kit 400 comprises a first container 405 comprising a first inlet 410, a second inlet 412, and a first outlet 415; a PIC container 420; a quencher container 425; a conduit 430 coupled at one end to the first container 405 and configured at the other end for coupling the PIC container 420 and the quencher container 425; a second container 407 comprising a first inlet 416, a first outlet 417, and an optional second outlet 419; a conduit 432; an optional infusion line assembly 445; and optionally at one end of conduit 430 (e.g., via a conduit branch): (a) a first adaptor 435 for coupling the PIC container 420 to the conduit, and (b) a second adaptor 440 for coupling the quencher container 425 to the conduit. This configuration further comprises a displacement device (e.g., an air displacement device) 455 suitable for improving (e.g., increasing) the transfer of the PIC and the quencher into container 405 (e.g., through the conduit 430 and into container 405). In some embodiments, the displacement device (e.g., air displacement device) 455 is coupled to the conduit 430 (e.g., via a 3-way conduit branch) at the end of the conduit comprising the first 435 and second 440 adaptors for coupling the PIC and quencher containers, 420 and 425 respectively. Dashed lines indicate that a whole blood (WB) composition may be provided to kit 400 by way of a blood collection container 450.

Figure 4C:
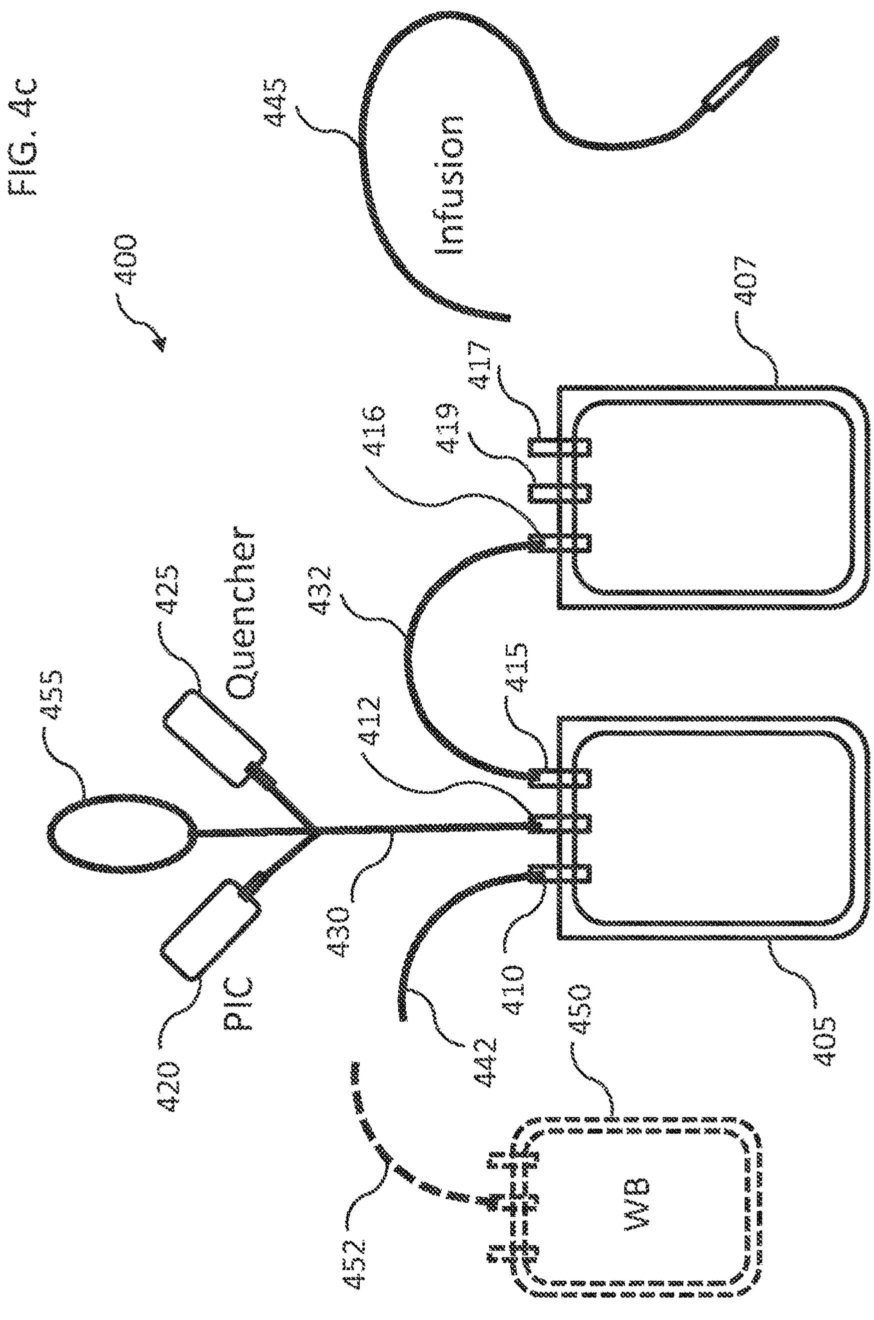
FIG. 4*c* shows an exemplary kit for use in preparing a pathogen inactivated whole blood composition in accordance with some embodiments. Dotted components depict a source container with whole blood (e.g., whole blood composition) for connecting to the kit. Also shown is an optional infusion line assembly ("Infusion"). Abbreviations: PIC, pathogen inactivation compound; WB, whole blood. Drawing not to scale.

An alternative configuration for an exemplary kit of the disclosure is shown in FIG. 4*c*. Similar to FIG. 4*b*, exemplary kit 400 comprises a first container 405 comprising a first inlet 410, a second inlet 412, and a first outlet 415; a PIC container 420; a quencher container 425; a displacement device (e.g., air displacement device) 455; a conduit 430 coupling (e.g., and providing a fluid communication path between) the first container 405 and the PIC container 420 and the quencher container 425; a second container 407 comprising a first inlet 416, a first outlet 417, and an optional second outlet 419; a conduit 432; and an optional infusion line assembly 445. This configuration comprises at one end of the conduit 430 (e.g., via conduit branch), the PIC container 420 coupled to the conduit, the quencher container 425 coupled to the conduit, and the displacement device (e.g., air displacement device) 455 coupled to the conduit suitable for improving (e.g., increasing) the transfer of the PIC and the quencher into container 405 (e.g., through the conduit 430 and into container 405). Dashed lines indicate that a whole blood (WB) composition may be provided to kit 400 by way of a blood collection container 450.

Figure 4D:
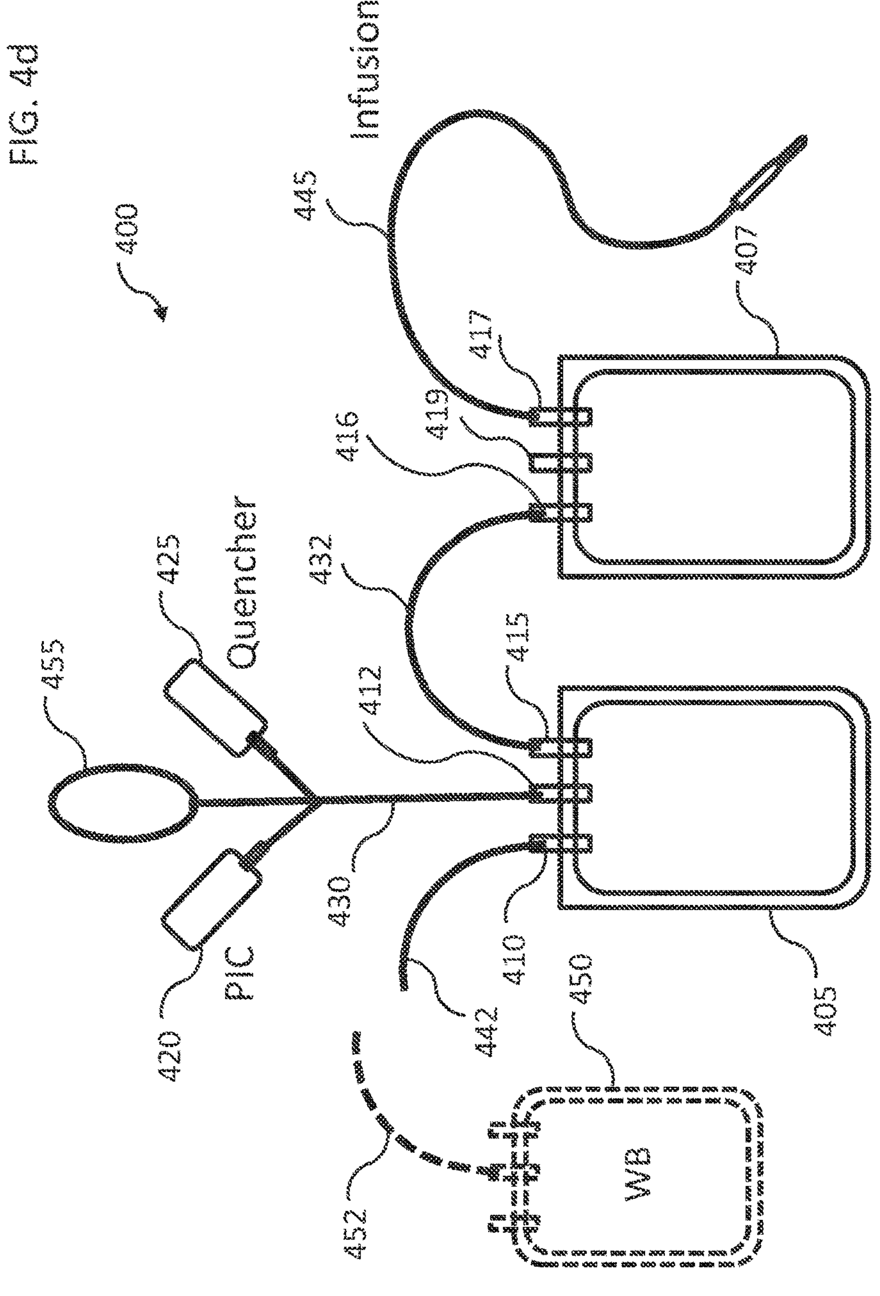
FIG. 4*d* shows an exemplary kit for use in preparing a pathogen inactivated whole blood composition in accordance with some embodiments. Dotted components depict a source container with whole blood (e.g., whole blood composition) for connecting to the kit. Abbreviations: PIC, pathogen inactivation compound; WB, whole blood. Drawing not to scale.

An alternative configuration for an exemplary kit of the disclosure is shown in FIG. 4*d*. Similar to FIG. 4*c*, exemplary kit 400 comprises a first container 405 comprising a first inlet 410, a second inlet 412, and a first outlet 415; a PIC container 420; a quencher container 425; a displacement device 455; a conduit 430 coupling (e.g., and providing a fluid communication path between) the first container 405 and the PIC container 420 and the quencher container 425; a second container 407 comprising a first inlet 416, a first outlet 417, and an optional second outlet 419; and a conduit 432. This configuration further comprises an infusion line assembly 445, wherein the infusion line assembly is coupled to the second container 407 (e.g., coupled to first outlet 417 of the second container). Dashed lines indicate that a whole blood (WB) composition may be provided to kit 400 by way of a blood collection container 450.

Figure 5A:
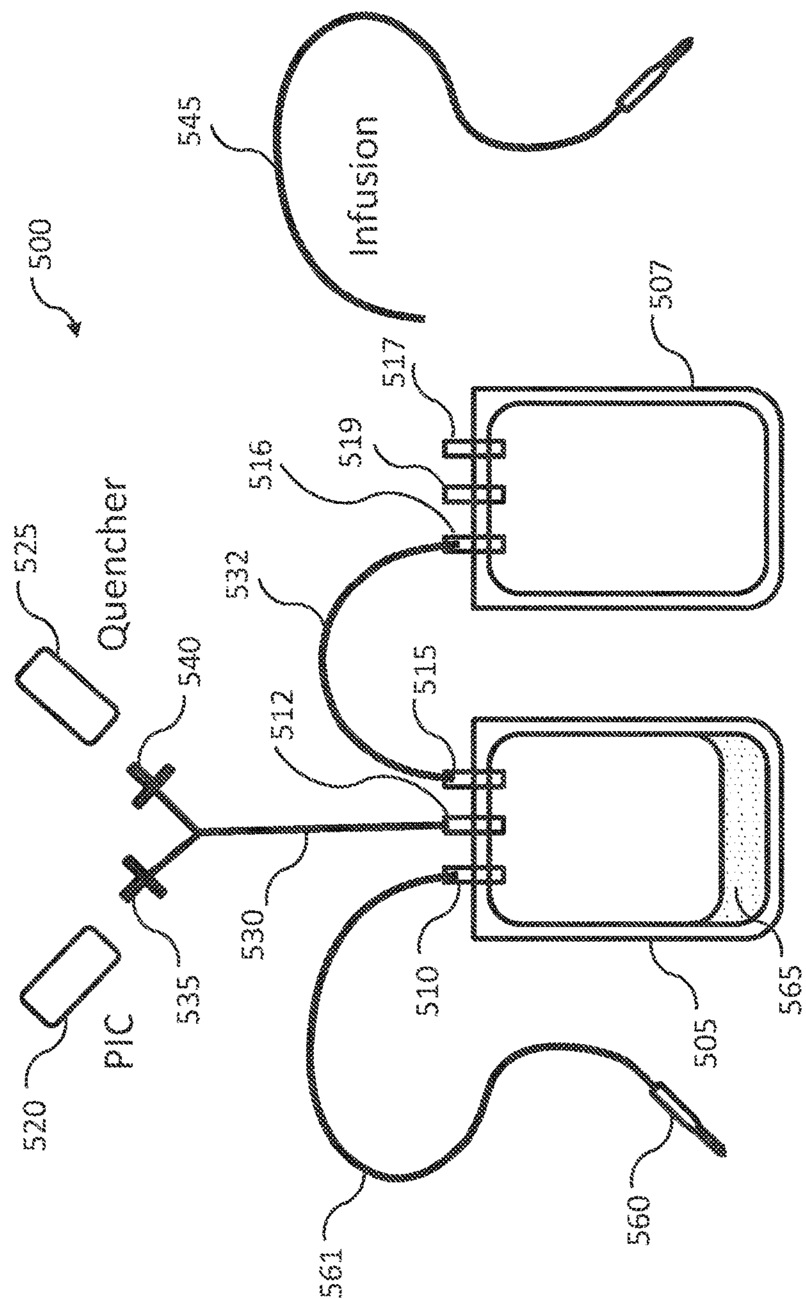
FIG. 5*a* shows an exemplary kit for use in preparing a pathogen inactivated whole blood composition in accordance with some embodiments. Also shown is an optional infusion line assembly ("Infusion"). Abbreviations: PIC, pathogen inactivation compound. Drawing not to scale.

The exemplary kit 500 shown in FIG. 5*a* comprises (e.g., includes): a first container 505 suitable for mixing a whole blood composition, a pathogen inactivation compound (PIC) and optionally a quencher, wherein the first container 505 comprises a first inlet 510, a second inlet 512, and a first outlet 515; a vascular access device 560 for drawing whole blood from a donor; a conduit 561 extending between the vascular access device 560 and the first inlet 510 of the first container; a second container 507 suitable for storing a pathogen-inactivated whole blood composition, wherein the second container 507 comprises a first inlet 516 and a first outlet 517, and an optional second outlet 519; a conduit 532 extending between the first container 505 (e.g., first outlet of the first container) and the second container 507 (e.g., first inlet of the second container); a container 520 containing a pathogen inactivation compound (PIC container); a container 525 containing a quencher (quencher container); a conduit 530 coupled at one end to the first container 505 (e.g., second inlet 512 of first container 505) and configured at the other end for coupling the PIC container 520 and the quencher container 525 (e.g., to provide a fluid communication path between the first container 505 and the PIC and quencher containers 520 and 525, respectively); and an optional infusion line assembly 545 for infusing a pathogen-inactivated whole blood composition into a subject. In some embodiments, the conduit 530 comprises at one end (e.g., via a 2-way conduit branch): (a) a first adaptor 535 for coupling (e.g., configured to be coupled to) the PIC container 520 to the conduit, and (b) a second adaptor 540 for coupling (e.g., configured to be coupled to) the quencher container 525 to the conduit. In some embodiments, the vascular access device 560 and conduit 561 together comprise a needle assembly. In some embodiments, the infusion line assembly 545 is configured to be coupled to the second container 507 (e.g., first outlet 517 of the second container; by way of a spike port). In some embodiments, container 505 contains an anticoagulant (e.g., anticoagulant solution) 565.

Figure 5B:
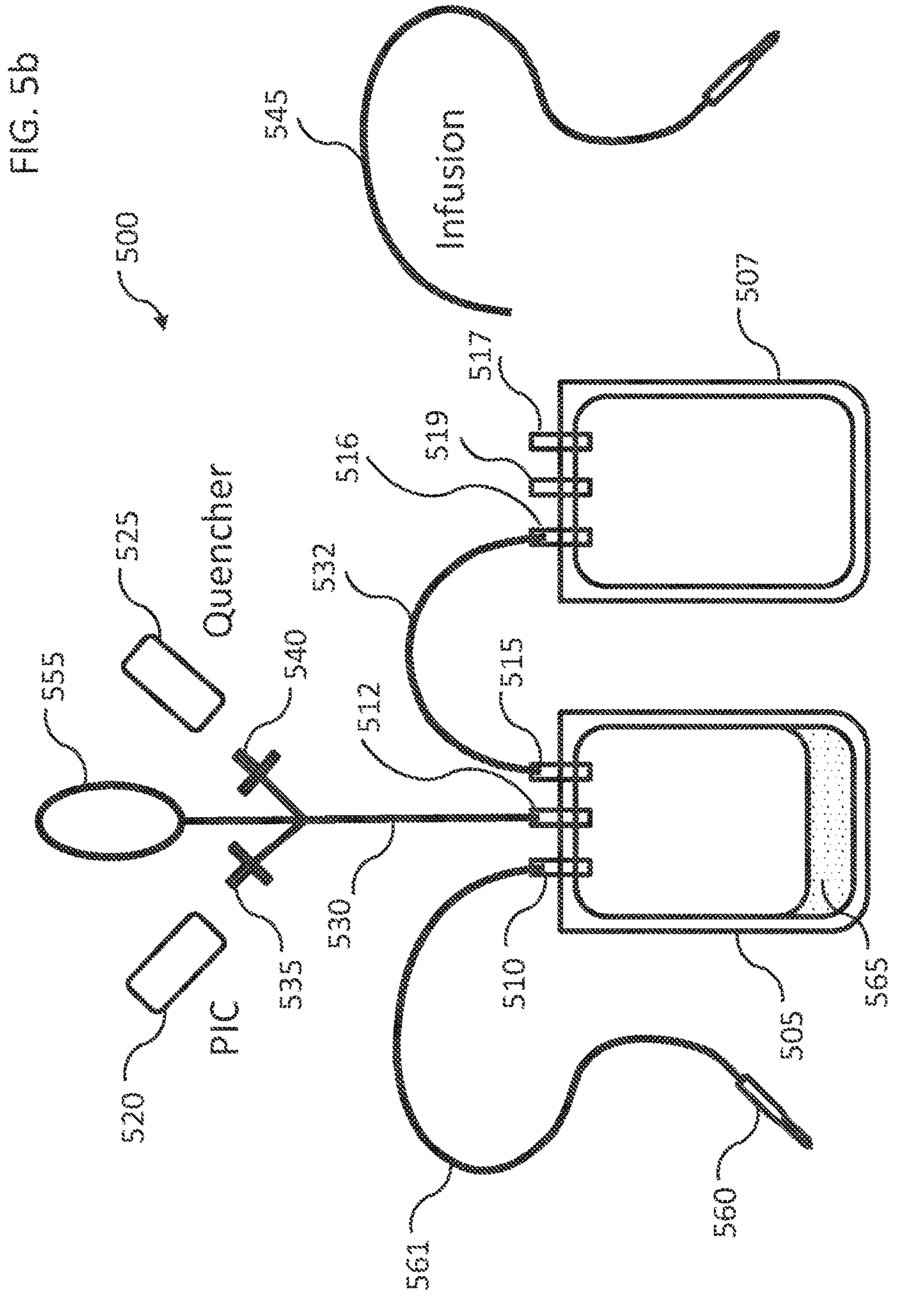
FIG. 5*b* shows an exemplary kit for use in preparing a pathogen inactivated whole blood composition in accordance with some embodiments. Also shown is an optional infusion line assembly ("Infusion"). Abbreviations: PIC, pathogen inactivation compound. Drawing not to scale.

An alternative configuration for an exemplary kit 500 of the disclosure is shown in FIG. 5*b*. Similar to FIG. 5*a*, exemplary kit 500 comprises a first container 505 comprising a first inlet 510, a second inlet 512, and a first outlet 515; a PIC container 520; a quencher container 525; a conduit 530 coupled at one end to the first container 505 and configured at the other end for coupling the PIC container 520 and the quencher container 525; a second container 507 comprising a first inlet 516, a first outlet 517, and an optional second outlet 519; a conduit 532; a vascular access device 560; a conduit 561; an optional infusion line assembly 545; and optionally at one end of conduit 530 (e.g., via a conduit branch): (a) a first adaptor 535 for coupling the PIC container 520 to the conduit, and (b) a second adaptor 540 for coupling the quencher container 525 to the conduit. This configuration further comprises a displacement device (e.g., an air displacement device) 555 suitable for improving (e.g., increasing) the transfer of the PIC and the quencher into container 505 (e.g., through the conduit 530 and into container 505). In some embodiments, the displacement device (e.g., air displacement device) 555 is coupled to the conduit 530 (e.g., via a 3-way conduit branch) at the end of the conduit comprising the first 535 and second 540 adaptors for coupling the PIC and quencher containers, 520 and 525 respectively. In some embodiments, container 505 contains an anticoagulant 565.

Figure 5C:
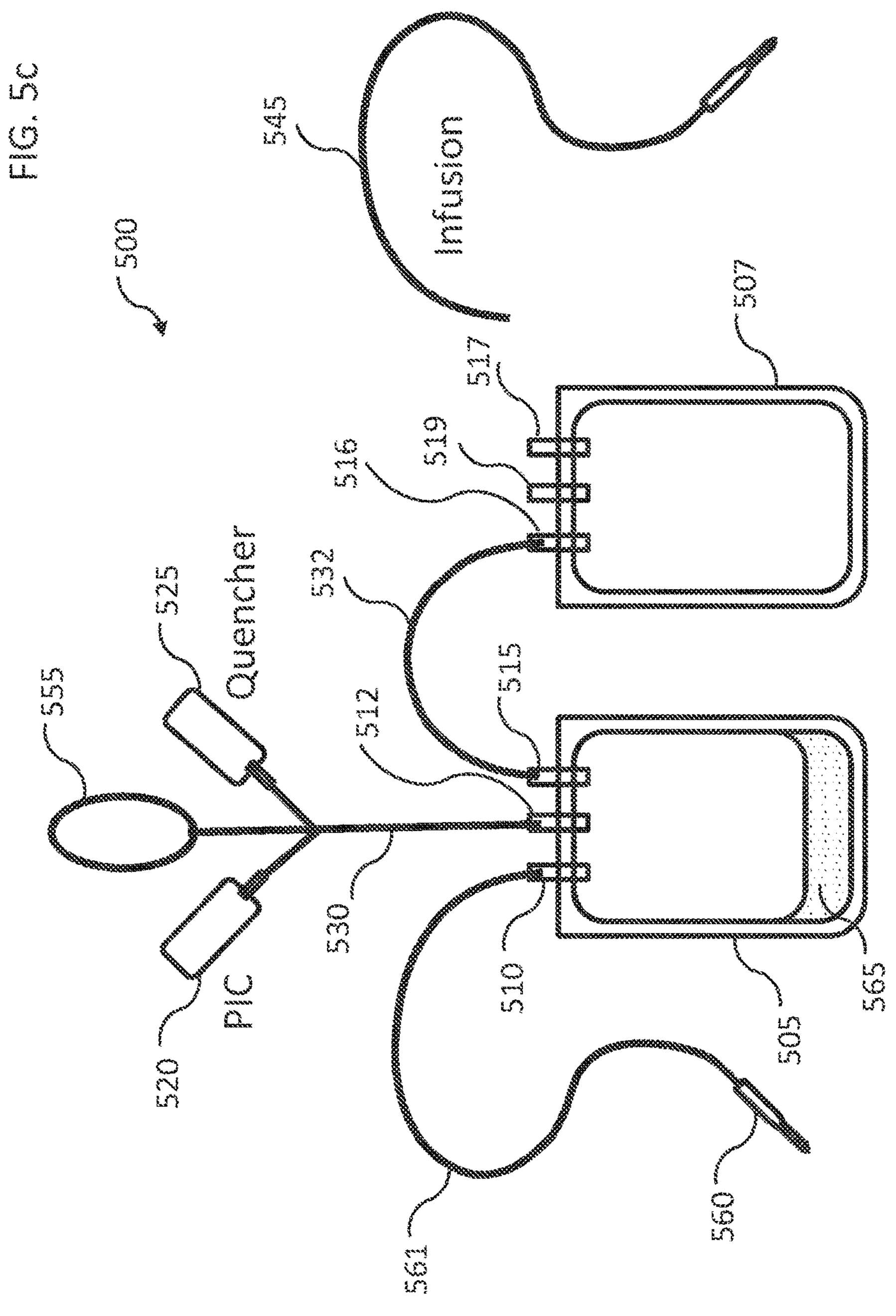
FIG. 5*c* shows an exemplary kit for use in preparing a pathogen inactivated whole blood composition in accordance with some embodiments. Also shown is an optional infusion line assembly ("Infusion"). Abbreviations: PIC, pathogen inactivation compound. Drawing not to scale.

An alternative configuration for an exemplary kit 500 of the disclosure is shown in FIG. 5*c*. Similar to FIG. 5*b*, exemplary kit 500 comprises a first container 505 comprising a first inlet 510, a second inlet 512, and a first outlet 515; a PIC container 520; a quencher container 525; a displacement device (e.g., an air displacement device) 555; a conduit 530 coupling (e.g., and providing a fluid communication path between) the first container 505 and the PIC container 520 and the quencher container 525; a second container 507 comprising a first inlet 516, a first outlet 517, and an optional second outlet 519; a conduit 532; a vascular access device 560; a conduit 561; and an optional infusion line assembly 545. This configuration comprises at one end of the conduit 530 (e.g., via conduit branch), the PIC container 520 coupled to the conduit, the quencher container 525 coupled to the conduit, and the displacement device (e.g., air displacement device) 555 coupled to the conduit suitable for improving (e.g., increasing) the transfer of the PIC and the quencher into container 505 (e.g., through the conduit 530 and into container 505). In some embodiments, container 505 contains an anticoagulant 565.

Figure 5D:
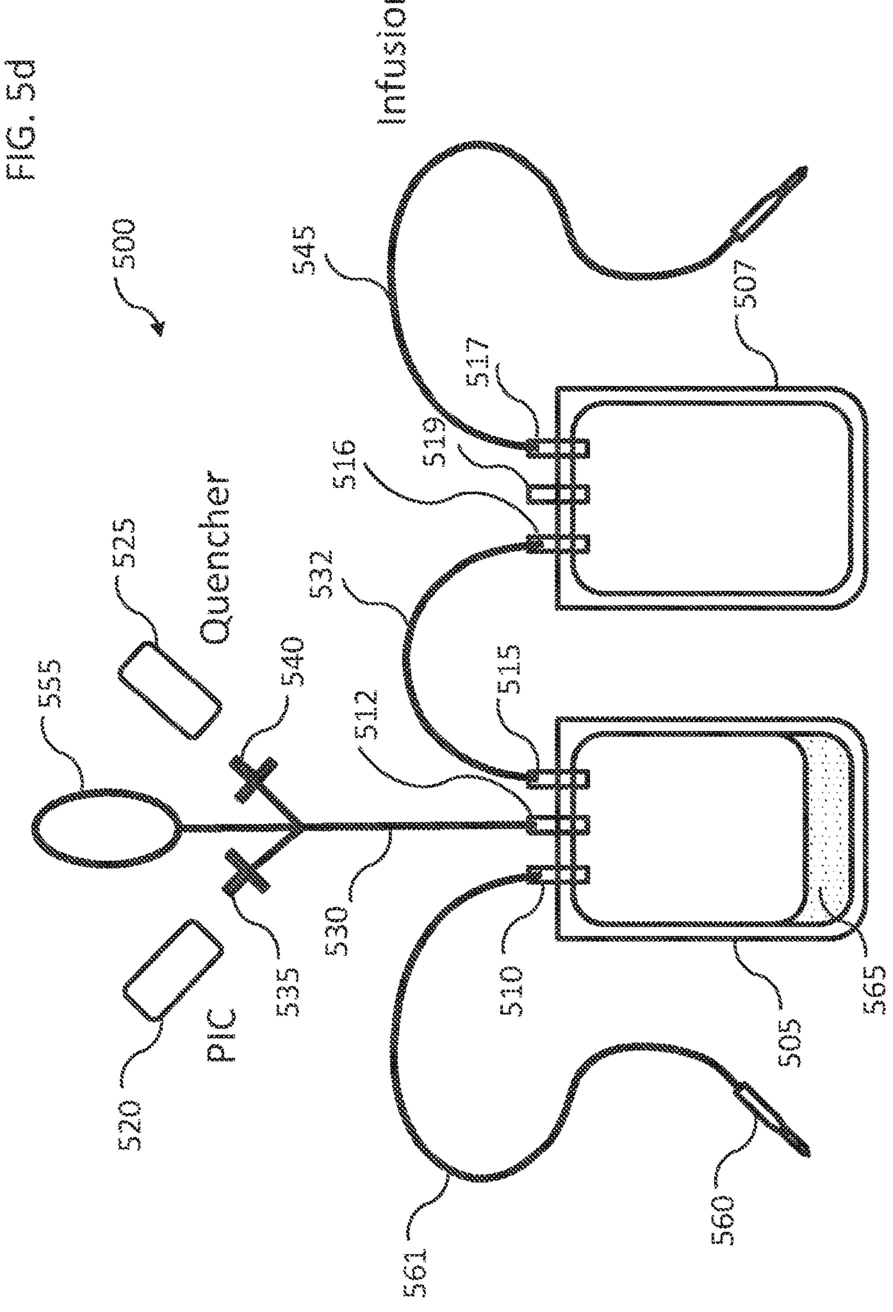
FIG. 5*d* shows an exemplary kit for use in preparing a pathogen inactivated whole blood composition in accordance with some embodiments. Abbreviations: PIC, pathogen inactivation compound. Drawing not to scale.

An alternative configuration for an exemplary kit 500 of the disclosure is shown in FIG. 5*d*. Similar to FIG. 5*b*, exemplary kit 500 comprises a first container 505 comprising a first inlet 510, a second inlet 512, and a first outlet 515; a PIC container 520; a quencher container 525; a conduit 530 coupled at one end to the first container 505 and configured at the other end for coupling the PIC container 520 and the quencher container 525; a displacement device 555; a second container 507 comprising a first inlet 516, a first outlet 517, and an optional second outlet 519; a conduit 532; a vascular access device 560; a conduit 561; an infusion line assembly 545; and optionally at one end of conduit 530 (e.g., via a conduit branch): (a) a first adaptor 535 for coupling the PIC container 520 to the conduit, and (b) a second adaptor 540 for coupling the quencher container 525 to the conduit. This configuration comprises an infusion line assembly 545, wherein the infusion line assembly is coupled to the second container 507 (e.g., coupled to first outlet 515 of the second container). In some embodiments, container 505 contains an anticoagulant 565.

Figure 5E:
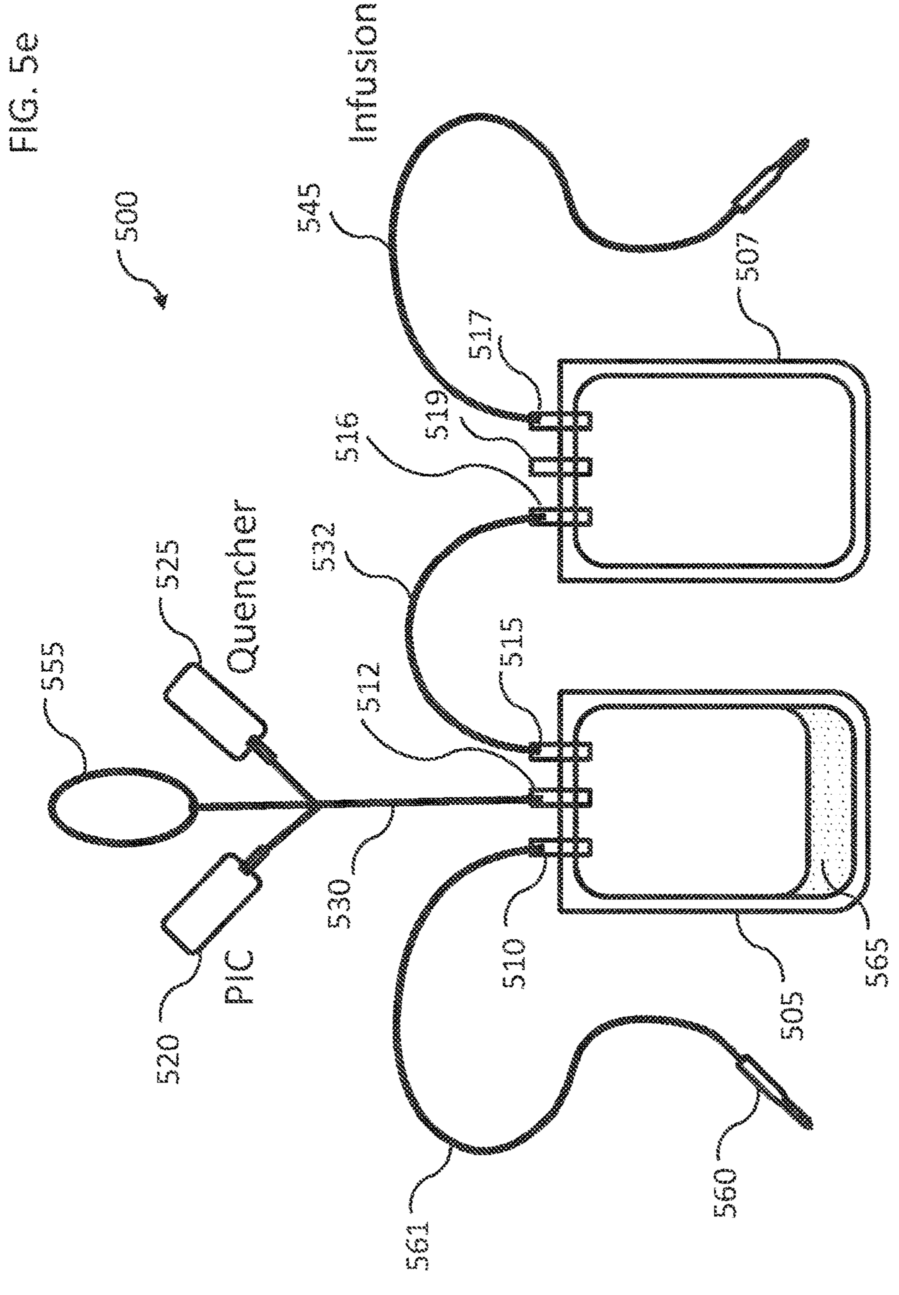
FIG. 5*e* shows an exemplary kit for use in preparing a pathogen inactivated whole blood composition in accordance with some embodiments. Abbreviations: PIC, pathogen inactivation compound. Drawing not to scale.

An alternative configuration for an exemplary kit 500 of the disclosure is shown in FIG. 5*e*. Similar to FIG. 5*c*, exemplary kit 500 comprises a first container 505 comprising a first inlet 510, a second inlet 512, and a first outlet 515; a PIC container 520; a quencher container 525; a displacement device 555; a conduit 530 coupling (e.g., and providing a fluid communication path between) the first container 505 and the PIC container 520 and the quencher container 525; a conduit 532; a second container 507 comprising a first inlet 516, a first outlet 517, and an optional second outlet 519; a vascular access device 560; a conduit 561; and an infusion line 545 coupled to container 507. In some embodiments, container 505 contains an anticoagulant 565.

Figure 5F:
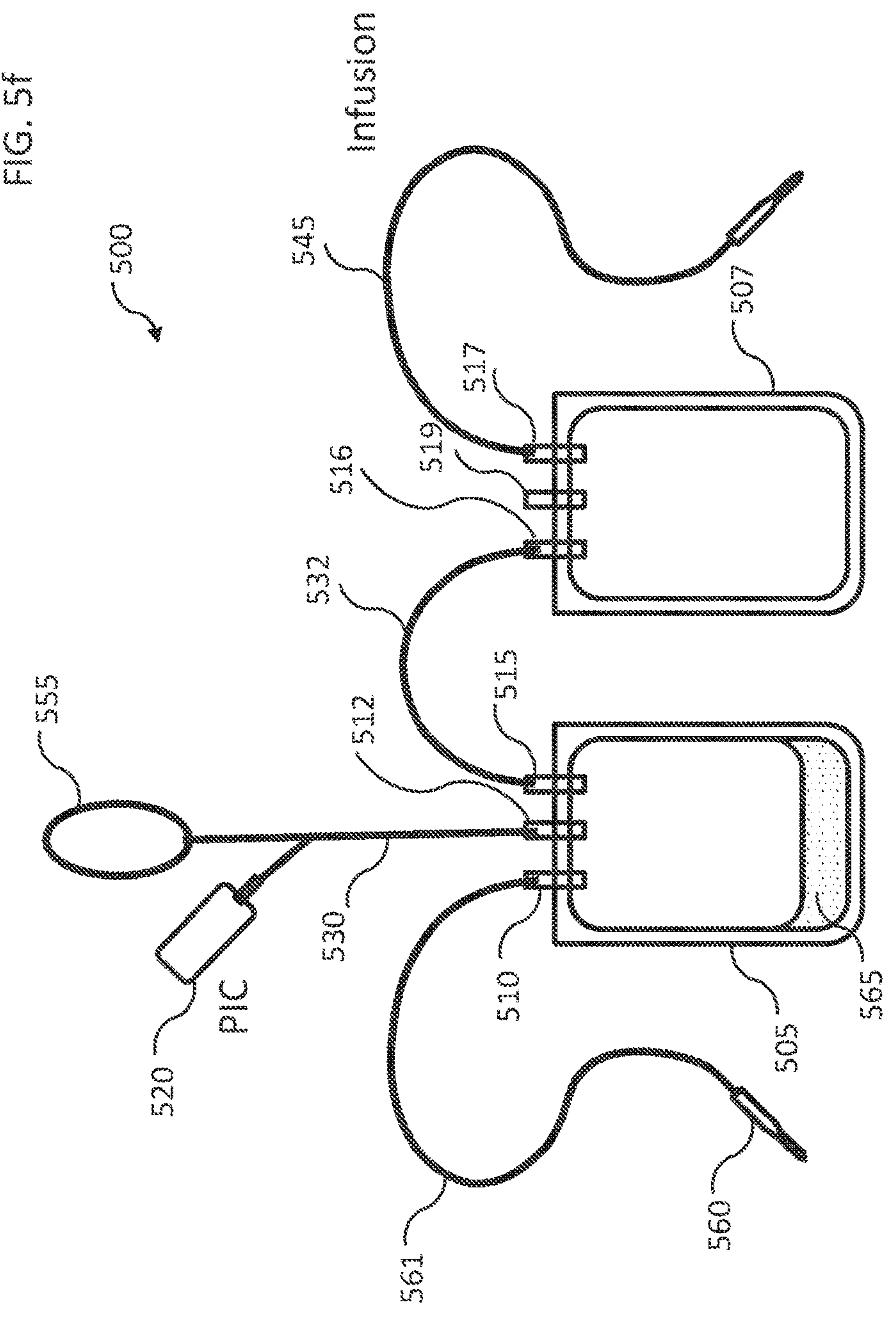
FIG. 5*f* shows an exemplary kit for use in preparing a pathogen inactivated whole blood composition in accordance with some embodiments. Abbreviations: PIC, pathogen inactivation compound. Drawing not to scale.

An alternative configuration for an exemplary kit 500 of the disclosure is shown in FIG. 5*f*. Similar to FIG. 5*e*, exemplary kit 500 comprises a first container 505 comprising a first inlet 510, a second inlet 512, and a first outlet 515; a PIC container 520; a displacement device 555; a conduit 530 coupling (e.g., and providing a fluid communication path between) the first container 505 and the PIC container 520; a conduit 532; a second container 507 comprising a first inlet 516, a first outlet 517, and an optional second outlet 519; a vascular access device 560; a conduit 561; and an infusion line assembly 545 coupled to container 507. In some embodiments, container 505 contains an anticoagulant 565.

Figure 5G:
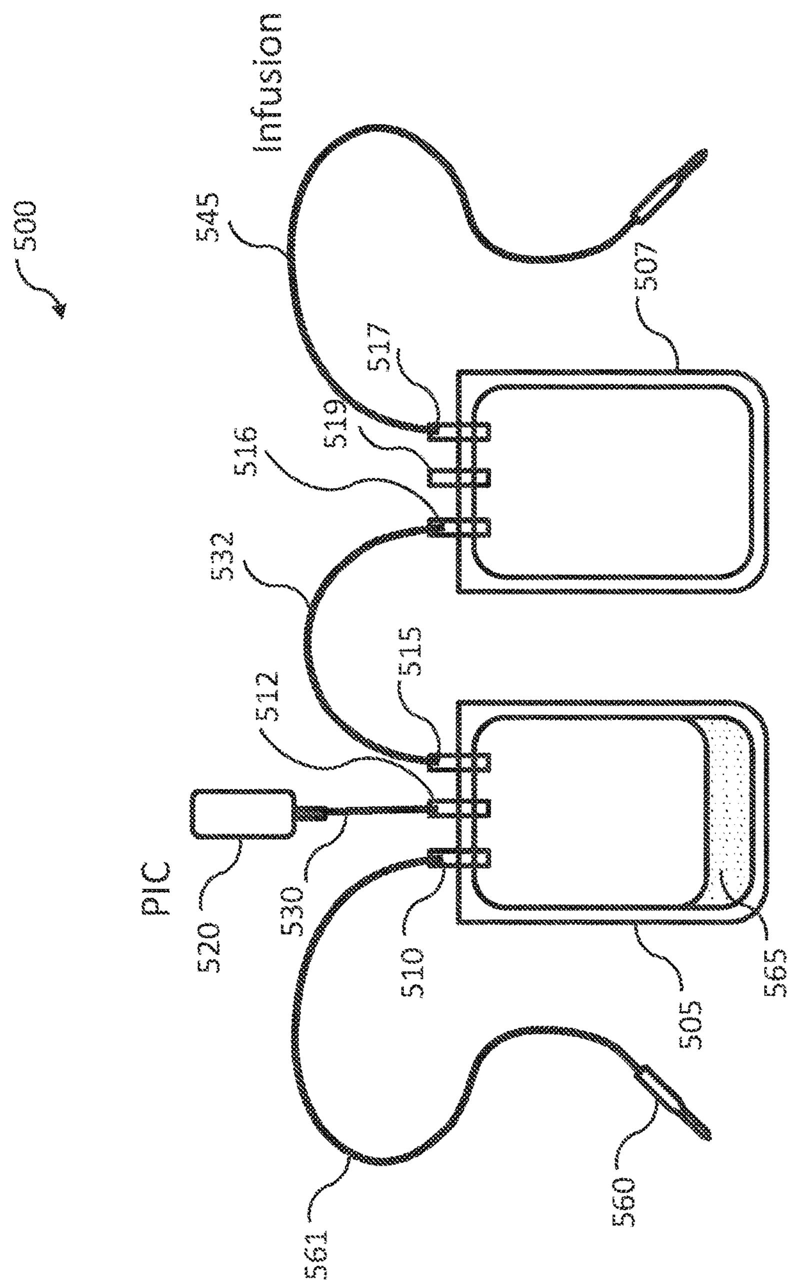
FIG. 5*g* shows an exemplary kit for use in preparing a pathogen inactivated whole blood composition in accordance with some embodiments. Abbreviations: PIC, pathogen inactivation compound. Drawing not to scale.

An alternative configuration for an exemplary kit 500 of the disclosure is shown in FIG. 5*g*. Similar to FIG. 5*f*, exemplary kit 500 comprises a first container 505 comprising a first inlet 510, a second inlet 512, and a first outlet 515; a PIC container 520; a conduit 530 coupling (e.g., and providing a fluid communication path between) the first container 505 and the PIC container 520; a conduit 532; a second container 507 comprising a first inlet 516, a first outlet 517, and an optional second outlet 519; a vascular access device 560; a conduit 561; and an infusion line assembly 545 coupled to container 507. In some embodiments, container 505 contains an anticoagulant 565.

As described herein, where conduit (e.g., tubing) is described as coupling or extending between (e.g., connecting), for example, two containers (e.g., bags) of kit (e.g., a processing set of a kit), it is understood that the conduit may be joined at some point therebetween by another component or connector of the connection between the two containers (e.g., bags). For example, a blood collection container coupled (e.g., connected) to a first container by a conduit includes wherein the conduit comprises a filter (e.g., leukoreduction filter) between the two containers, i.e. the tubing is divided by a filter such that fluid flows (e.g., sterile transfer) from one container to the other through the conduit and filter. Alternatively, or in addition, the conduit between containers allows for fluid to flow from one container to another (e.g., fluid communication path, sterile transfer), which can be blocked to prevent the flow until necessary or desired, e.g. as part of the processing the fluid in one container may be prevented from flowing to the next container until required or desired for the next step in a process (e.g., openable fluid communication path). As such an openable seal, such as a clamp, plug, valve or the like is included in or on the conduit connecting the containers, where the clamp, plug, valve or the like can be selectively opened as required, for example to transfer the fluid from one container to the next. In certain embodiments, the conduit between containers comprises a breakable seal, such as a breakable valve or frangible connector, whereupon breaking the breakable seal allows for the blood product solution to flow between the containers through the conduit. It is understood that the breakable seal is contained within the connection between containers, such that sterility of the system is maintained. It is also understood that a conduit comprising a filter, or a breakable seal, includes where the conduit may be interrupted by the filter or the seal, for example the conduit runs from one container and is connected to the filter or seal (an incoming portion of the conduit), and the conduit continues from another portion of the filter or seal to another container (an outgoing portion of the conduit). In such a configuration, fluid flows from the first container, through the incoming portion of the conduit, through the filter or seal, and through the outgoing portion of the conduit and into the other container. In certain embodiments, a coupling or connection between a conduit and an inlet or outlet (e.g., port) of a container, or the inlet or outlet itself, may comprise a breakable or pierceable seal, such as a breakable valve or frangible connector or spike port, whereupon breaking or piercing the seal allows for the blood product solution to flow (e.g., sterile transfer) between the conduit and the container.

Different containers (e.g., bags) within a pathogen inactivation processing set can be used for different steps of a process. For example, a system of containers to be used for the pathogen inactivation of a whole blood composition can include a container with pathogen inactivation compound contained within, a container with a quencher contained within, a container for receiving the unit of whole blood (e.g., whole blood donation) and a pathogen inactivation compound (e.g. first container) and a quencher, and one or more containers for containing the final whole blood product, i.e. the pathogen inactivated whole blood unit(s) (e.g., therapeutic dosage unit) that has the concentration of the pathogen inactivation compound and/or by-products thereof reduced to below a desired concentration, which is ready for use or can be stored for later use (e.g., referred to as a product bag, storage bag). Blood containers typically can be designed to hold various volumes of fluid, including, but not limited to, volumes ranging from 50 mL to 2 liters, for example having up to about 350 mL capacity, 450 mL capacity, 500 mL capacity, 600 mL capacity, 700 mL capacity, 800 mL capacity, 900 mL capacity, 1 liter capacity, up to a 1.5 liter capacity, or up to a 2 liter capacity. Each bag in the system is typically made up of a plastic material. For example, the container for containing a solution of pathogen inactivation compound can be made of a suitable plastic such as PL2411 (Baxter Healthcare), or other plastics such as polyvinyl chloride, polyolefins, ethylene vinyl acetate, ethylene vinyl acetate blended with other plastics, and the like. Suitable bag materials are discussed, for example, in PCT publication number WO 2003078023, and U.S. Pat. No. 7,025,877, the disclosures of which are hereby incorporated by reference as it relates to such bag materials and related materials. In all cases, the materials used in preparing the processing set should be sterilizable by known methods such as steam and gamma or electron beam radiation used to ensure sterility of the processing set. While these are exemplary materials for making the bags, the methods described herein are applicable to processes using any suitable bag material as would be readily available to one skilled in the art, and can also be used with containers other than bags. The bags used herein may be designed to allow for gases such as oxygen and carbon dioxide to go into and out of the blood bag, so that the blood products therein have adequate oxygen supply and carbon dioxide levels during the processing and storage.

The present disclosure also provides a method of infusing whole blood into a subject (e.g., human subject) in need thereof, comprising infusing into the subject an aforementioned pathogen-inactivated whole blood composition or an aforementioned therapeutic dosage unit of pathogen-inactivated whole blood.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects. Rather, the scope of this disclosure should be determined with reference to the appended claims.

The invention is illustrated further by the following examples, which are not to be construed as limiting the invention in scope or spirit to the specific procedures described in them.

EXAMPLES

Example 1: Preparation of Pathogen-Inactivated Whole Blood

Pathogen inactivated whole blood was prepared with the pathogen inactivation compound, amustaline, and the quencher glutathione (Henschler et al., 2011, Transfus Med Hemother 38:33-42), in a kit of the present disclosure comprising a treatment container and tubing with a 3-way branch for introducing the amustaline/GSH (e.g., a "filter set") comprising two in line filters for coupling (e.g., connecting) containers (e.g., syringes) of PIC and quencher, and the third branch coupled to (e.g., connected to) a sample diversion pouch (e.g., FIG. 3*b*). More specifically, four ABO-matched whole blood units containing anticoagulant were pooled and split into 8 half units (225 mL/half unit), added into each of eight treatment bags by connecting the pooled donor blood bag containing the whole blood to the treatment container by way of the tubing and using a tubing welder. Following transfer of the whole blood into the treatment containers, the pooled donor blood bag was removed by sealing and severing the tubing, and the filter set was sterile coupled using a tubing welder to the same input port of the treatment container via the remaining tubing. Amustaline and GSH were added to final concentrations of 0.2 mM and 2.0 mM, respectively. GSH was added first, followed by addition of amustaline, either within 5 minutes of GSH addition or after at least 15 minutes hold time, as indicated in Table 1. The mixtures were incubated at 22° C. (Units 1-4) or 25° C. (Units 5-8), with samples removed at the indicated times for analysis by liquid chromatography-mass spectrometry (LCMS) to determine the level of residual, unreacted amustaline.

TABLE 1

Residual amustaline levels (nM) in pathogen-inactivated whole blood

| Unit | GSH | 21 hr | 24 hr | 27 hr | 30 hr | 33 hr | 36 hr | 42 hr |
|---|---|---|---|---|---|---|---|---|
| 1 | >15 min | 3.50 | 2.62 | 2.27 | 2.11 | 2.61 | 1.62 | 1.30 |
| 2 | >15 min | 4.09 | 2.66 | 3.07 | 2.95 | 2.29 | 1.38 | 1.35 |
| 3 | <5 min | 3.45 | 3.04 | 3.29 | 2.67 | 2.16 | 1.73 | 1.66 |
| 4 | <5 min | 3.85 | 3.53 | 3.7 | 2.84 | 2.22 | 1.41 | 1.57 |
| 5 | >15 min | 2.91 | 2.44 | 2.55 | 2.04 | 1.76 | 1.89 | 1.62 |
| 6 | >15 min | 3.21 | 2.58 | 2.71 | 2.49 | 1.47 | 1.87 | 1.22 |
| 7 | <5 min | 3.43 | 2.86 | 2.74 | 2.34 | 1.64 | 2.28 | 1.11 |
| 8 | <5 min | 4.15 | 3.39 | 3.30 | 2.59 | 2.83 | 1.97 | 2.96 |

Additionally, 50 mL of the mixture was removed from each of Units 2 and 8 at 24 hr and divided into two 25 mL samples in separate containers to compare storage at 4° C. versus room temperature, and for evaluation of residual amustaline levels at 2, 4, 6 and 8 hours of storage under those conditions (Table 2).

TABLE 2

Residual amustaline levels (nM) in pathogen-inactivated whole blood

| Unit | Temp | 2 hr | 4 hr | 6 hr | 8 hr |
|---|---|---|---|---|---|
| 2 | RT | BLOQ | BLOQ | BLOQ | BLO |
| 8 | RT | BLOQ | BLOQ | BLOQ | BLOQ |
| 2 | 4° C. | 1.69 | 1.66 | 1.49 | 1.09 |
| 8 | 4° C. | 2.69 | 1.77 | 1.89 | 1.64 |

BLOQ = Below Limit of Quantitation (e.g., < 0.75 nM)

As shown in Table 1, residual amustaline levels ranged from 2.91 to 4.15 nM concentration at 21 hr, with further decreases to the range of 1.11 to 2.96 nM at the final 42 hr sampling time. In contrast, it was surprisingly observed that the transfer of the treatment mixtures from Units 2 and 8 to a different container at 21 hr, followed by further storage at room temperature, resulted in a decrease in residual amustaline to below the limit of quantitation (Table 2), which was not achieved by continued incubation at 22° C. or 25° C. in the treatment container for the initial Units (Table 1). Transfer and incubation at 4° C. did not yield a comparable decrease in residual amustaline (Table 2). These results suggested an effect of the transfer step and further incubation at room temperature on the level or residual amustaline.

Example 2: Preparation of Pathogen-Inactivated Whole Blood

Another study was performed to evaluate the effect of container transfer on residual levels of amustaline after pathogen-inactivation of whole blood using a 3-container kit of the present disclosure to allow for one or two transfer steps from the initial (e.g., first) container and a similar filter set as Example 1. Six ABO matched whole blood units in anticoagulant were pooled and split into six ~450 mL units transferred into the first blood bag container of the kit comprising Transfufol 3226 PVC film (Renolit), followed by severing and sealing the pooled donor blood bag, and subsequent connection by tubing welding of a filter set to the same input port (e.g., attached tubing) of the first container, for transferring amustaline and GSH into the whole blood. Amustaline and GSH were added to the whole blood units at final concentrations of 0.2 mM and 2.0 mM, respectively, followed by transfer of the mixture to the second bag (Transfufol 3226 PVC film) and incubated at 22° C. At 22 hr, samples were taken for analysis along with transfer of the mixture to the third bag (Transfufol 3226 PVC film), followed by further incubation at 22° C., with additional samples taken for analysis at 24 hr (i.e., 2 hr post-final transfer) and 26 hr (i.e., 4 hr post-final transfer).

TABLE 3

Residual amustaline levels (nM) in pathogen-inactivated whole blood

| Unit | 22 hr | 24 hr | 26 hr |
|---|---|---|---|
| 1 | 1.39 nM | BLOQ | BLOQ |
| 2 | 1.35 nM | 0.75 nM | BLOQ |
| 3 | 1.96 nM | BLOQ | BLOQ |
| 4 | 1.84 nM | BLOQ | BLOQ |
| 5 | 1.55 nM | BLOQ | BLOQ |
| 6 | 1.46 nM | BLOQ | BLOQ |

BLOQ = Below Limit of Quantitation (e.g., < 0.75 nM)

Samples were analyzed by LCMS to determine the level of residual, unreacted amustaline as previously described. As shown in Table 3, transfer of the mixture to a second bag immediately after amustaline/GSH addition to the whole blood and followed by incubation at 22° C. for 22 hr showed residual amustaline levels of 1.35 to 1.96 nM. Following transfer of the mixture to a third bag after incubation to 22 hr, followed by further incubation at 22° C. for an additional 2 hr (24 hr column) or 4 hr (26 hr column), residual amustaline levels were reduced to below 1 nM for all samples and below the limit of quantitation in all but one sample.

Example 3: Preparation of Pathogen-Inactivated Whole Blood

In another study, pathogen-inactivated whole blood was prepared using amustaline and GSH, in 1-container or 3-container kits of the present disclosure, with the 3-container kits comprising second and third bags (e.g., transfer/storage containers) from three different sources (e.g., different plastics materials). The three different transfer/storage containers included a 600 mL container, comprising Transfufol 3226 PVC film ("PVC1"), a second 600 mL container from a different manufacturer comprising Transfufol 3226 PVC film ("PVC2"), and a 750 mL container from Cerus, comprising EVA (ethylene-vinyl acetate) 1800 film ("EVA"). Six ABO-matched whole blood units in anticoagulant were pooled and split into seven units of ~450 mL each. The seven whole blood units were subjected to pathogen inactivation under conditions of no transfer step between containers (e.g., processing performed in the 1-container kit), or two transfer steps between containers (e.g., processing performed in the 3-container kits) of the indicated storage/transfer bag source (Table 4). Amustaline and GSH were added to the whole blood units as described previously by sterile docking of a filter set to the tubing of an input port of the first containers, which contained the whole blood. Unit 1 was treated with amustaline and GSH at 0.2 mM and 2.0 mM final concentrations, respectively, in the first container and incubated at 22° C., with samples taken at 18, 20, 22 and 24 hours, with no container transfers. For units 2-7, amustaline and GSH were added to the whole blood (0.2 mM and 2.0 mM final concentrations, respectively) in the first container, followed by transfer to the second container and incubation at 22° C. for 18 hours. At 18 hours, samples were taken along with transfer of the mixture to the third container and further incubation at 22° C., with additional sampling at 2 hour intervals (20, 22 and 24 hr).

TABLE 4

Residual amustaline levels (nM) in pathogen-inactivated whole blood

| Unit | Transfer Bag | Transfer* | 18 hr | 20 hr | 22 hr | 24 hr |
|---|---|---|---|---|---|---|
| 1 | N/A | No | 2.16 | 1.99 | 1.46 | 1.54 |
| 2 | PVC1 | 2x | 1.75 | 0.88 | BLOQ | BLOQ |
| 3 | PVC1 | 2x | 1.52 | 0.78 | BLOQ | BLOQ |
| 4 | PVC2 | 2x | 1.48 | 0.87 | BLOQ | BLOQ |
| 5 | PVC2 | 2x | 1.45 | 0.85 | BLOQ | BLOQ |
| 6 | EVA | 2x | 3.11 | 1.14 | BLOQ | BLOQ |
| 7 | EVA | 2x | 3.51 | 1.22 | BLOQ | BLOQ |

*No transfer = 1 bag kit; 2x transfer = 3 bag kit
BLOQ = Below Limit of Quantitation (e.g., <0.75 nM)

All samples were analyzed by LCMS to determine the level of residual, unreacted amustaline as previously described. As shown in Table 4, the level of residual amustaline at 18 hr was lowest for Units 2-5, in which the whole blood/amustaline/GSH mixture had been transferred to one of two container types in the 3-container kits prior to the 18 hr incubation, but not for a third container type (Units 6-7). Following a second transfer (i.e., to third container) at 18 hr and further incubation at 22° C., residual amustaline was less than 1 nM at the 20 hr time point (i.e., 2 hours after bag transfer) for kits with two different container types and approaching 1 nM for kits with the third container type. At 22 hr and 24 hr (i.e., incubation for 4 or 6 hours after bag transfer), the level of residual amustaline was below the limit of quantitation for all samples processed in the 3-container kits, with each of the three different container types. In contrast, the level of amustaline remained in the range of 1.54 to 1.99 nM at 20, 22 and 24 hr after processing with the 1-container set and no transfer.

Example 4: Preparation of Pathogen-Inactivated Whole Blood

Another study was performed to evaluate the preparation of pathogen-inactivated whole blood using amustaline and GSH, in 1-container, 2-container or 3-container kits of the present disclosure. Six ABO-matched whole blood units in anticoagulant were pooled and split into seven units of ~450 mL. The seven whole blood units were subjected to pathogen inactivation under one of three conditions—with no transfer step between containers, one transfer step between two containers, or two transfer steps between three containers (Table 5). Amustaline and GSH were added to the whole blood units by sterile docking of a filter set as previously described to the tubing of an input port of the first container that contained the whole blood. Unit 1 was treated with amustaline and GSH at 0.2 mM and 2.0 mM final concentrations, respectively, in the first container and incubated at 22° C., with samples taken at 20, 22, 24 and 26 hours, with no further container transfers. For units 2-4, amustaline and GSH were added to the whole blood (0.2 mM and 2.0 mM final concentrations, respectively) in the first container and incubated at 22° C. for 20 hours. A sample was taken at 20 hours, along with transfer to a second bag and further incubation at 22° C., with additional sampling at 2 hour intervals (22, 24 and 26 hr). For units 5-7, amustaline and GSH were added to the whole blood (0.2 mM and 2.0 mM final concentrations, respectively) in the first container and the mixture transferred to a second container, followed by incubation at 22° C. for 20 hours. A sample was taken at 20 hours, along with transfer to a third bag and further incubation at 22° C., with additional sampling at 2 hour intervals (22, 24 and 26 hr).

TABLE 5

Residual amustaline levels (nM) in pathogen-inactivated whole blood

| Unit | Transfer* | 20 hr | 22 hr | 24 hr | 26 hr |
|---|---|---|---|---|---|
| 1 | No | 1.47 | 1.54 | 1.39 | 1.32 |
| 2 | 1x | 1.53 | BLOQ | BLOQ | BLOQ |
| 3 | 1x | 1.65 | BLOQ | BLOQ | BLOQ |
| 4 | 1x | 1.66 | BLOQ | BLOQ | BLOQ |
| 5 | 2x | 1.53 | BLOQ | BLOQ | BLOQ |
| 6 | 2x | 1.47 | BLOQ | BLOQ | BLOQ |
| 7 | 2x | 1.46 | BLOQ | BLOQ | BLOQ |

*No transfer = 1 bag kit;
1x transfer = 2 bag kit;
2x transfer = 3 bag kit
BLOQ = Below Limit of Quantitation (e.g., < 0.75 nM)

Samples were analyzed by LCMS to determine the level of residual, unreacted amustaline as previously described. As shown in Table 5, the level of amustaline was below the limit of quantitation after PI processing of whole blood with both the 2-container and 3-container kits, while the level of amustaline remained in the range of 1.32 to 1.54 nM with the 1-container set after processing.

Example 5: Preparation of Pathogen-Inactivated Whole Blood

A further study was performed to evaluate additional conditions for the preparation of pathogen-inactivated whole blood using amustaline and GSH in 2-container kits of the present disclosure (e.g., FIG. 3*b*). Amustaline and GSH were added to the whole blood units at 0.2 mM and 2.0 mM final concentrations, respectively, in the first container. The mixtures were then incubated at 22° C. for 18, 20 or 22 hr in the first container (e.g., treatment container) before transfer to a second container, with samples taken for analysis as indicated in Table 6, up until the time point of transfer to the second container. Following transfer to the second container the mixtures were further incubated at 22° C., with sampling for analysis at 2 hr intervals as shown in Table 6.

TABLE 6

Residual amustaline levels (nM) in pathogen-inactivated whole blood

| Unit | Transfer time | 18 hr | 20 hr | 22 hr | 24 hr | 26 hr |
|---|---|---|---|---|---|---|
| 1 | 18 hr | 1.51 | 2.51 | 2.01 | 2.22 | 0.98 |
| 2 | 18 hr | 1.21 | 1.06 | 0.91 | 0.75 | BLOQ |
| 3 | 18 hr | 1.07 | 1.04 | 0.81 | BLOQ | BLOQ |
| 4 | 18 hr | 1.05 | 1.02 | 1.03 | BLOQ | BLOQ |
| 5 | 18 hr | 34.50 | 8.29 | 1.67 | 1.06 | BLOQ |
| 6 | 18 hr | 3.45 | 1.64 | 1.79 | 0.95 | BLOQ |
| 7 | 18 hr | 2.04 | 2.08 | 2.04 | 1.35 | BLOQ |
| 8 | 20 hr | N/A | 1.71 | 1.27 | 1.50 | 1.21 |
| 9 | 20 hr | N/A | 1.29 | 0.79 | BLOQ | BLOQ |
| 10 | 20 hr | N/A | 1.48 | 0.89 | 0.91 | BLOQ |
| 11 | 20 hr | N/A | 1.29 | 0.78 | 0.86 | BLOQ |
| 12 | 20 hr | N/A | 1.92 | 0.91 | 0.86 | BLOQ |
| 13 | 20 hr | N/A | 1.82 | 0.90 | 0.78 | BLOQ |
| 14 | 20 hr | N/A | ** | 1.13 | 0.95 | 0.77 |
| 15 | 22 hr | N/A | N/A | 1.52 | BLOQ | BLOQ |
| 16 | 22 hr | N/A | N/A | 1.63 | BLOQ | BLOQ |
| 17 | 22 hr | N/A | N/A | 1.78 | BLOQ | BLOQ |
| 18 | 22 hr | N/A | N/A | 2.21 | BLOQ | BLOQ |
| 19 | 22 hr | N/A | N/A | 4.29 | BLOQ | BLOQ |
| 20 | 22 hr | N/A | N/A | 2.76 | BLOQ | BLOQ |
| 21 | 22 hr | N/A | N/A | 3.27 | BLOQ | BLOQ |

BLOQ = Below Limit of Quantitation (e.g., <0.75 nM)
** Sample not available for analysis Samples were analyzed by LCMS to determine the level of residual, unreacted amustaline as previously described. As shown in Table 6, and compared to control units 1, 8 and 14, reduction of the level of amustaline to below 1 nm or further (e.g., below the limit of quantitation) after PI processing was most consistently achieved with a transfer step at 20 or 22 hr.

Example 6: Collection and Preparation of Pathogen-Inactivated Whole Blood

In some embodiments, whole blood pathogen inactivation kits of the present disclosure are designed for the collection of whole blood from a donor directly into the first container (e.g., treatment container) of a kit, eliminating the need for collecting whole blood into a donor blood bag and then connecting the donor blood bag containing the whole blood to the kit. For example, 1-container, 2-container or 3-container kits as provided herein may further comprise an integrated vascular access device, such as for example a venipuncture needle, coupled to the treatment container (e.g., containing anticoagulant) of the kit by way of one or more segments of flexible tubing (e.g., FIGS. 5*a*-5*d*). In this configuration, whole blood is drawn from a donor directly into the treatment container of the kit, with pathogen inactivation compound added, mixed with the whole blood, and incubated in the same container. A study was performed to demonstrate the feasibility of treating whole blood with amustaline and GSH directly in blood collection containers from commercially available collection sets.

More specifically, whole blood units were collected from donors and treated in either Teruflex (Terumo, BB*AGD506A2) blood collection bags (Units 2-7) or Leucoflex (MacoPharma, LQE7230LD) blood collection bags (Units 9-14) containing anticoagulant and integrated into a kit of the present disclosure. Six ABO-matched whole blood units were pooled and split into a control unit and six test units of ~450 mL each. Control units 1 and 8 used kits described in previous Examples. A filter set as previously described was sterile docked to the whole blood transfer tubing of the container that had been sealed and severed, followed by addition of amustaline and GSH to final concentrations of about 0.2 mM and 2.0 mM, respectively. GSH was added first, followed by addition of amustaline within 30 minutes. The mixtures were then incubated at 22° C. for 20 hr, with samples taken for analysis and transfer of the mixtures to the second integrally connected container for test Units 2-7 and 9-14, followed by further incubation and sampling at 2 hr intervals (i.e., 22 hr, 24 hr) for all Units as shown in Table 7.

TABLE 7

Residual amustaline levels (nM) in pathogen-inactivated whole blood

| Unit | Collection Bag | 20 hr | 22 hr | 24 hr |
|---|---|---|---|---|
| 1 | T | 2.35 | 1.61 | 1.81 |
| 2 | T | 1.29 | BLOQ | BLOQ |
| 3 | T | 1.62 | BLOQ | BLOQ |
| 4 | T | 1.53 | BLOQ | BLOQ |
| 5 | T | 1.92 | BLOQ | BLOQ |
| 6 | T | 2.12 | BLOQ | BLOQ |
| 7 | T | 2.32 | BLOQ | BLOQ |
| 8 | M | 2.62 | 1.93 | 1.85 |
| 9 | M | 1.36 | BLOQ | BLOQ |
| 10 | M | 1.32 | BLOQ | BLOQ |
| 11 | M | 1.44 | BLOQ | BLOQ |
| 12 | M | 1.34 | BLOQ | BLOQ |
| 13 | M | 1.49 | BLOQ | BLOQ |
| 14 | M | 1.40 | BLOQ | BLOQ |

BLOQ = Below Limit of Quantitation (e.g., < 0.75 nM)

Residual amustaline levels in the pathogen-inactivated whole blood preparation were analyzed by LCMS and found to be below the limit of quantitation for each of the Units transferred to the second bag at 20 hr.

In another example, a 2-container kit comprising a treatment container and a filter set (e.g., described above) for introducing the amustaline/GSH (e.g., FIG. 8*c*) is used to collect from a donor 450 mL of whole blood into the first container that contains 63 mL of anticoagulant CPDA-1 (e.g., blood:anticoagulant ratio approximately 7:1), through the first inlet port. The collection line is then closed using a medical tubing clamp and the whole blood and anticoagulant solution are mixed. The pathogen inactivation compound amustaline and the quencher GSH are next added to the whole blood in the first container through the second port, to final concentrations of about 0.2 mM and 2.0 mM, respectively. The mixture of whole blood, PIC and quencher are incubated at 22° C. for 20 hours, followed by transfer of the mixture to the second container, clamping the tubing between the first and second containers, and incubating the mixture at 22° C. for a further 2-4 hours to provide a pathogen-inactivated whole blood unit.

Residual amustaline levels in the pathogen-inactivated whole blood preparation are determined by sampling from the second container and LCMS analysis to demonstrate levels below 1 nm (e.g., below the limit of quantitation of 0.75 nM).

Example 7: Infusing Pathogen-Inactivated Whole Blood

Pathogen inactivated whole blood (e.g., ABO compatible, RhD compatible, Group O) prepared as provided herein is infused into a subject in need thereof (e.g., for trauma resuscitation), using standard transfusion methods known in the art. More specifically, in one example, a commercially available transfusion line (e.g., transfusion line assembly, with integral filter) is connected via a spike port outlet to the second container of a kit, which contains pathogen-inactivated whole blood prepared as described above. The unit of pathogen-inactivated whole blood is infused from the kit by gravity flow into a subject acutely hemorrhaging due to trauma, in accordance with accepted medical practices for such infusion. Additional units of pathogen-inactivated whole blood are infused as necessary.

Example 8: Preparation of Pathogen-Inactivated RBCs and Cryoprecipitate

Pathogen-inactivated whole blood may be used for producing blood products, such as for example, pathogen-inactivated red blood cells (RBCs), plasma and/or cryoprecipitate preparations. More specifically, in one example, a preparation of pathogen inactivated whole blood generated as previously described is subjected to centrifugation under conditions to separate RBCs and plasma. More specifically, the pathogen-inactivated whole blood unit is centrifuged at 4200 g for 10 minutes at 4° C. to separate plasma from the RBCs, followed by removal of most of the plasma layer using an expression device, and transfer to a container separate from the packed RBC concentrate. A small amount of plasma is maintained with the RBCs to yield a unit with the desired hematocrit (e.g., 60%) and the RBC unit is stored refrigerated at 1-6° C. The unit of pathogen inactivated plasma is then frozen at −30° C. for use in the preparation of cryoprecipitate.

Additionally, a study was performed to evaluate plasma and red blood cells prepared from a pathogen-inactivated whole blood composition, either shortly after the whole blood PI treatment process, or after storing the pathogen-inactivated whole blood at 4° C. prior to preparing the plasma and red blood cell components. Donor whole blood units were pooled and split into seven units (e.g., to standardize across units), and subjected to treatment conditions as follows. Unit 1 was the control and treated only with saline, while units 2-7 were treated with amustaline and GSH, at concentrations of about 0.2 mM and 2.0 mM, respectively. Following addition of the amustaline and GSH, or the saline, in the first container (bag), the units were incubated at 22° C. for 22 hours, and then transferred to the second container (bag). Sampling was done at the time of transfer, and also at 24 hours and 26 hours (2 or 4 hours post-transfer, also incubated at 22° C.), for analysis of residual amustaline, hemolysis and/or fibrinogen and Factor VIII levels. At 4 hours post-transfer (and further incubation), units 1-4 were then stored at 4° C., while units 5-7 were separated into plasma and red blood cell components by centrifugation at 3800 rpm for 6 minutes at 22° C., with SAGM additive solution then added to the red blood cell component after separation from the plasma. Plasma components from units 5-7 were then sampled for fibrinogen and Factor VIII analysis (e.g., using standard analytical methods) and the plasma components stored at 4° C. Red blood cell components from units 5-7 were sampled for residual amustaline and hemolysis, and the red blood cell components also stored at 4° C. Sampling of the plasma and red blood cell components was also done at Day 2, Day 5 and Day 7. Additionally, at Days 2, 5 and 7, samples were removed from the stored pathogen-inactivated whole blood, centrifuged to obtain plasma and red blood cells, and similarly analyzed. Residual amustaline concentrations (nM) are shown below in Table 8, and fibrinogen and Factor VIII levels are shown in Tables 9a and 9b. Hemolysis levels were within acceptable ranges and not shown. Other plasma coagulation factors and/or properties for analysis may include, for example, Factor II, Factor V, Factor VII, Factor IX, Factor X, Factor XI, PT, PTT and/or TT.

TABLE 8

Residual amustaline levels (nM) in pathogen-inactivated whole blood

| Unit | 22 hr | 24 hr | 26 hr |
|---|---|---|---|
| 2 | 1.39 | BLOQ | BLOQ |
| 3 | 1.35 | 0.75 | BLOQ |
| 4 | 1.96 | BLOQ | BLOQ |
| 5 | 1.84 | BLOQ | BLOQ |
| 6 | 1.55 | BLOQ | BLOQ |
| 7 | 1.46 | BLOQ | BLOQ |

BLOQ = Below Limit of Quantitation (e.g., < 0.75 nM)

TABLE 9a

Fibrinogen and Factor VIII in plasma from pathogen inactivate whole blood

| Unit | Day | Fibrinogen | Factor VIII |
|---|---|---|---|
| 1 | 26 hr | 257 | 86.9 |
| 5 | | 244 | 67.8 |
| 6 | | 248 | 67.8 |
| 7 | | 242 | 80.7 |
| 5 | Day 2 | 216 | 65.1 |
| 6 | | 240 | 71.3 |
| 7 | | 249 | 72.8 |
| 5 | Day 5 | 222 | 64.5 |
| 6 | | 244 | 66.4 |
| 7 | | 240 | 67.8 |
| 5 | Day 7 | 242 | 82.4 |
| 6 | | 215 | 60.7 |
| 7 | | 233 | 62 |

TABLE 9b

Fibrinogen and Factor VIII in plasma from pathogen inactivate whole blood

| Unit | Day | Fibrinogen | Factor VIII |
|---|---|---|---|
| 1 | 26 hr | 242 | 112 |
| 2 | | 242 | 67.8 |
| 3 | | 246 | 69.2 |
| 4 | | 246 | 62.6 |
| 2 | Day 2 | 246 | 71.3 |
| 3 | | 250 | 67.1 |
| 4 | | 244 | 62.6 |
| 2 | Day 5 | 246 | 77.4 |
| 3 | | 244 | 74.3 |
| 4 | | 242 | 67.8 |
| 2 | Day 7 | 244 | 67.1 |
| 3 | | 246 | 69.2 |
| 4 | | 242 | 75.1 |

For preparing cryoprecipitate, units of frozen plasma prepared from pathogen-inactivated whole blood are thawed in a temperature controlled 4° C. water bath, with a total thaw time of approximately 4 hr 30 min. The thawed units are then centrifuged for 12 minutes at 4° C. at 4200 rcf, with a slow deceleration. Cryo-reduced plasma supernatants are removed from the cryoprecipitate, while maintaining a small amount of plasma for resuspension of the cryoprecipitate. Following resuspension, the cryoprecipitate unit may be used for infusion or frozen for storage at −30° C.

Disclosed examples and embodiments disclosed herein further describe methods, kits, and compositions for preparing a pathogen-inactivated whole blood composition and other pathogen-inactivated blood product compositions, including for example pathogen-inactivated whole blood and other blood product compositions suitable for infusion into an individual. The illustrated components and steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Although embodiments have been fully described with reference to the accompanying drawings, it should be noted that various changes and modifications will be apparent to those skilled in the art. Such changes and modifications are to be understood as being included within the scope of the various embodiments as defined by the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element, it is specifically contemplated that a closed-ended term can be used in place of the open-ended term without departing from the spirit and scope of the disclosure. Recitation of ranges of values herein are merely intended to serve as a shorthand method of referring individually to each separate value falling within the range, unless otherwise indicated herein, and each separate value is incorporated into the specification as if it were individually recited herein. Reference to "about" a value or parameter herein includes (and describes) variations that are directed to that value or parameter per se. For example, description referring to "about X" includes description of "X". All methods described herein can be performed in any suitable order unless otherwise indicated herein or otherwise clearly contradicted by context. The use of any and all examples, or exemplary language (e.g., "such as") provided herein, is intended merely to better illuminate the description and does not pose a limitation on the scope of the description unless otherwise claimed. No language in the specification should be construed as indicating any non-claimed element as essential to the practice of the methods, systems and compositions disclosed herein.

Preferred embodiments are described herein. Variations of those preferred embodiments may become apparent to those working in the art upon reading the foregoing description. It is expected that skilled artisans will be able to employ such variations as appropriate, and the practice of the methods, systems and compositions described herein otherwise than as specifically described herein. Accordingly, the methods, systems and compositions described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context. The following is a list of particular embodiments of the present disclosure. The list is exemplary is it not intended to be limiting of the disclosure provided herein.

Embodiment 1. A method of preparing a pathogen inactivated whole blood composition, comprising:

(a) mixing in a first container
  (i) a whole blood composition;
  (ii) an effective amount of a pathogen inactivating compound (PIC); and
  (iii) optionally an effective amount of a quencher;
(b) incubating in the first container the mixture of the whole blood composition, the PIC and optionally the quencher, under conditions and for a time sufficient to inactivate a pathogen, if present;
(c) transferring the mixture under sterile conditions to a second container; and
(d) incubating in the second container the mixture under conditions and for a time sufficient to reduce the concentration of the PIC
  (i) to a concentration at least 25% less than the concentration of the PIC in the mixture at the time of transfer step (b);
  (ii) to a concentration at least $10^5$ fold less than the concentration of the PIC in the mixture of step (a); and/or
  (iii) to a concentration of about 1 nm or less, thereby yielding the pathogen inactivated whole blood composition.

Embodiment 2. The method of embodiment 1, wherein the concentration of the PIC in the mixture of step (a) is at least about 0.1 mM.

Embodiment 3. The method of embodiment 1 or embodiment 2, wherein the concentration of the PIC in the mixture of step (a) is about 0.1 mM to about 1.0 mM.

Embodiment 4. The method of any one of embodiments 1-3, wherein the concentration of the PIC in the mixture of step (a) is about 0.2 mM.

Embodiment 5. The method of any one of embodiments 1-4, wherein the concentration of the PIC after step (d) is less than about 2 nM.

Embodiment 6. The method of any one of embodiments 1-5, wherein the concentration of the PIC after step (d) is less than about 1 nM.

Embodiment 7. The method of any one of embodiments 1-6, wherein the PIC comprises a functional group which is, or which forms, a reactive electrophilic group.

Embodiment 8. The method of embodiment 7, wherein the functional group is selected from the group consisting of a mustard, a mustard intermediate, and a mustard equivalent.

Embodiment 9. The method of embodiment 7 or embodiment 8, wherein the functional group is, or is capable of forming, an aziridinium ion.

Embodiment 10. The method of any one of embodiments 1-9, wherein the reactive electrophilic group is capable of reacting with nucleic acids.

Embodiment 11. The method of any one of embodiments 1-10, wherein the PIC comprises a nucleic acid binding ligand.

Embodiment 12. The method of embodiment 11, wherein the nucleic acid binding ligand is an intercalator.

Embodiment 13. The method of embodiment 12, wherein the intercalator is an acridine.

Embodiment 14. The method of any one of embodiments 11-13, wherein the PIC comprises a frangible linker linking the functional group and the nucleic acid binding ligand.

Embodiment 15. The method of any one of embodiments 1-14, wherein the PIC is β-alanine, N-(acridin-9-yl), 2-[bis(2-chloroethyl)amino]ethyl ester.

Embodiment 16. The method of any one of embodiments 1-15, wherein step (a) comprises mixing in the first container a whole blood composition, an effective amount of a PIC, and an effective amount of a quencher.

Embodiment 17. Embodiment The method of embodiment 16, wherein the concentration of the quencher in the mixture of step (a) is at least about 1 mM.

Embodiment 18. The method of embodiment 16 or embodiment 17, wherein the concentration of the quencher in the mixture of step (a) is about 1 mM to about 10 mM.

Embodiment 19. The method of any one of embodiments 16-18, wherein the concentration of the quencher in the mixture of step (a) is about 2 mM.

Embodiment 20. The method of any one of embodiments 16-19, wherein the concentration of the PIC in the mixture of step (a) is about 0.2 mM and the concentration of the quencher in the mixture of step (a) is about 2 mM.

Embodiment 21. The method of any one of embodiments 16-20, wherein the quencher comprises a thiol group, wherein the thiol is capable of reacting with the reactive electrophilic group of the pathogen-inactivating compound.

Embodiment 22. The method of any one of embodiments 16-21, wherein the quencher comprises cysteine or a derivative of cysteine.

Embodiment 23. The method of any one of embodiments 16-22, wherein the quencher is glutathione or a pharmaceutically acceptable salt thereof.

Embodiment 24. The method of any one of embodiments 16-23, wherein the quencher is glutathione monosodium salt.

Embodiment 25. The method of any one of embodiments 1-24, wherein the mixture of step (a) further comprises an anticoagulant.

Embodiment 26. The method of any one of embodiments 1-25, wherein the whole blood composition further comprises an anticoagulant.

Embodiment 27. The method of any one of embodiments 1-25, wherein the first container contains an anticoagulant and the whole blood composition is mixed with the anticoagulant in the first container.

Embodiment 28. The method of any one of embodiments 1-27, wherein the whole blood composition has a volume of about 250 mL to about 700 mL.

Embodiment 29. The method of any one of embodiment 25-28, wherein the ratio of anticoagulant to whole blood in the whole blood composition is about 1:5 to about 1:9.

Embodiment 30. The method of any one of embodiments 1-29, wherein the whole blood composition is added into the first container through a first inlet of the first container.

Embodiment 31. The method of any one of embodiments 1-30, wherein the whole blood composition is added into the first container from a donor collection container containing the whole blood composition.

Embodiment 32. The method of any one of embodiments 1-30, wherein the whole blood composition is added into the first container by collecting the whole blood composition from a whole blood donor into the first container.

Embodiment 33. The method of embodiment 32, wherein the whole blood composition is collected from a whole blood donor into the first container through a first conduit extending between a vascular access device and a first inlet of the first container and providing a fluid communication path for transferring the whole blood composition from the vascular access device into the first container.

Embodiment 34. The method of any one of embodiments 1-33, wherein the PIC and optionally the quencher are added into the first container through a first inlet of the first container.

Embodiment 35. The method of any one of embodiments 1-33, wherein the PIC and optionally the quencher are added into the first container through a second inlet of the first container.

Embodiment 36. The method of embodiment 34 or embodiment 35, wherein the PIC and optionally the quencher are added into the first container through a conduit extending between a container containing the PIC (PIC container) and optionally a container containing the quencher (quencher container) and an inlet of the first container, and providing a fluid communication path for transferring the PIC from the PIC container and optionally for transferring the quencher from the optional quencher container, into the first container.

Embodiment 37. The method of embodiment 36, wherein the PIC and the quencher are added into the first container through a conduit extending between the PIC container and the quencher container and an inlet of the first container, and wherein the conduit comprises at one end: (a) a first adaptor for coupling the PIC container to the conduit, (b) a second adaptor for coupling the quencher container to the conduit, and optionally (c) an air displacement device for increasing the transfer of the PIC and the quencher through the conduit and into the first container.

Embodiment 38. The method of any one of embodiments 1-37, wherein the incubating step (b) is about 2 hours to about 24 hours.

Embodiment 39. The method of embodiment 38, wherein the incubating step (b) is about 18 hours to about 22 hours.

Embodiment 40. The method of any one of embodiments 1-39, wherein the incubating step (b) is at room temperature.

Embodiment 41. The method of any one of embodiments 1-40, wherein the transferring step (c) is through a conduit extending between the first container to the second container.

Embodiment 42. The method of embodiment 41, wherein the conduit connects a first outlet of the first container to a first inlet of the second container.

Embodiment 43. The method of any one of embodiments 1-42, wherein the incubating step (d) is about 1 hour to about 8 hours.

Embodiment 44. The method of embodiment 43, wherein the incubating step (d) is about 2 hours to about 4 hours.

Embodiment 45. The method of any one of embodiments 1-44, wherein the incubating step (d) is at room temperature.

Embodiment 46. The method of any one of embodiments 1-45, further comprising transferring the pathogen-inactivated whole blood composition from the second container to a third container.

Embodiment 47. The method of any one of embodiments 1-46, further comprising (e) storing the pathogen inactivated whole blood composition at about 2-6° C.

Embodiment 48. The method of any one of embodiments 1-47, wherein the pathogen-inactivated whole blood composition is suitable for infusion.

Embodiment 49. The method of any one of embodiments 1-48, further comprising separating the pathogen-inactivated whole blood composition into one or more of a red blood cell composition, a plasma composition, or a platelet composition.

Embodiment 50. The method of any one of embodiments 1-49, further comprising separating the pathogen-inactivated whole blood composition into a plasma composition, and preparing a cryoprecipitate composition from the plasma composition.

Embodiment 51. A pathogen-inactivated whole blood composition prepared by the method of any one of embodiments 1-48.

Embodiment 52. The pathogen-inactivated whole blood composition of embodiment 51, wherein the pathogen-inactivated whole blood composition is suitable for infusion.

Embodiment 53. A red blood cell composition prepared by the method of embodiment 49.

Embodiment 54. A cryoprecipitate composition prepared by the method of embodiment 50.

Embodiment 55. A method of infusing a pathogen-inactivated whole blood composition into a subject in need thereof, the method comprising infusing into the subject a pathogen-inactivated whole blood composition prepared by the method of any one of embodiments 1-48 or a pathogen-inactivated whole blood composition of embodiment 51 or embodiment 52.

Embodiment 56. The method of embodiment 55, wherein the method comprises coupling an infusion line to a first outlet of the second container and infusing the pathogen-inactivated whole blood composition into the subject.

Embodiment 57. A kit for preparing a pathogen-inactivated whole blood composition, comprising:

(a) a vascular access device for drawing whole blood from a donor;

(b) a first container suitable for mixing the whole blood and a pathogen inactivating compound (PIC), wherein the first container comprises at least a first inlet and a first outlet;

(c) a first conduit extending between the vascular access device and the first inlet of the first container and providing a fluid communication path for transferring the whole blood from the vascular access device into the first container; and (d) a container containing a pathogen inactivating compound (PIC container).

Embodiment 58. The kit of embodiment 57, wherein the PIC container is configured to be coupled by a fluid communication path to the first inlet of the first container.

Embodiment 59. The kit of embodiment 58, wherein the PIC container is configured to be coupled to the first conduit.

Embodiment 60. The kit of embodiment 57, wherein the first container comprises a second inlet and the PIC container is configured to be coupled by a fluid communication path to the second inlet of the first container.

Embodiment 61. The kit of any one of embodiments 57-60, further comprising a container containing a quencher (quencher container).

Embodiment 62. The kit of embodiment 61, wherein the quencher container is configured to be coupled by a fluid communication path to the first inlet of the first container.

Embodiment 63. The kit of embodiment 62, wherein the quencher container is configured to be coupled to the first conduit.

Embodiment 64. The kit of embodiment 61, wherein the quencher container is configured to be coupled by a fluid communication path to the second inlet of the first container.

Embodiment 65. The kit of any one of embodiments 60-64, wherein the PIC container and the quencher container are the same container.

Embodiment 66. The kit of any one of embodiments 60-65, further comprising a second conduit wherein the second conduit comprises at one end at least one adaptor for coupling the PIC container and/or the quencher container to the second conduit.

Embodiment 67. The kit of embodiment 66, wherein the second conduit comprises at one end a first adaptor for coupling the PIC container to the second conduit and a second adaptor for coupling the quencher container to the second conduit.

Embodiment 68. The kit of any one of embodiments 60-65, further comprising a second conduit wherein the second conduit is coupled at one end to the PIC container and/or the quencher container.

Embodiment 69. The kit of any one of embodiments 66-68, wherein the second conduit is configured to be coupled to the first container, providing a fluid communication path between the PIC container and/or quencher container and the first container.

Embodiment 70. The kit of embodiment 69, wherein the second conduit is configured to be coupled to the first inlet of the first container.

Embodiment 71. The kit of embodiment 69 or embodiment 70, wherein the second conduit is coupled to the second inlet of the first container.

Embodiment 72. The kit of any one of embodiments 66-68, wherein the second conduit is configured to be coupled to the first conduit, providing a fluid communication path between the PIC container and/or quencher container and the first container.

Embodiment 73. The kit of any one of embodiments 66-72, further comprising an air displacement device for increasing the transfer of the PIC and/or the quencher through the second conduit and into the first container.

Embodiment 74. The kit of any one of embodiments 57-73, wherein the first container contains an anticoagulant.

Embodiment 75. The kit of any one of embodiments 57-74, further comprising a second container suitable for storing a pathogen-inactivated whole blood composition, wherein the second container comprises at least a first inlet and a first outlet.

Embodiment 76. The kit of embodiment 75, further comprising a third conduit extending between the first outlet of the first container and the first inlet of the second container and providing a fluid communication path for transferring a mixture comprising a whole blood composition and a PIC from the first container into the second container.

Embodiment 77. The kit of embodiment 75 or embodiment 76, wherein the kit comprises a third container suitable for storing a pathogen-inactivated whole blood composition, wherein the third container comprises at least a first inlet and a first outlet, and wherein the kit further comprises a fourth conduit extending between the first outlet of the second container and the first inlet of the third container and providing a fluid communication path for transferring a mixture comprising a whole blood composition and a PIC from the second container into the third container.

Embodiment 78. Embodiment The kit of any one of embodiments 1-77, further comprising an infusion line for infusing the pathogen-inactivated whole blood composition into a subject, wherein the infusion line comprises a second vascular access device and an infusion line conduit extending between the first outlet of the second container and the second vascular access device, wherein the infusion line conduit provides a fluid communication path for sterilely transferring the pathogen-inactivated whole blood composition from the second container to the vascular access device.

Embodiment 79. Embodiment A kit for preparing a pathogen-inactivated whole blood composition, comprising:

(a) a first container suitable for mixing a whole blood composition, a pathogen inactivating compound (PIC) and a quencher, wherein the first container comprises at least a first inlet and a first outlet;

(b) a second container suitable for storing a pathogen-inactivated whole blood composition, wherein the second container comprises at least a first inlet and a first outlet;

(c) a container containing a pathogen inactivating compound (PIC container);

(d) a container containing a quencher (quencher container);

(e) a first conduit, wherein the first conduit at one end is coupled to or configured to be coupled to a PIC container and a quencher container, and wherein the first conduit further comprises an air displacement device for increasing the transfer of the PIC and the quencher through the first conduit; and (f) a second conduit extending between the first container and the second container and providing a fluid communication path for transferring the whole blood composition from the first container to the second container.

Embodiment 80. The kit of embodiment 79, wherein the first conduit further comprises at least one adaptor for coupling the second conduit to a PIC container and a quencher container.

Embodiment 81. The kit of embodiment 80, wherein the first conduit comprises a first adaptor for coupling a PIC container to the first conduit and a second adaptor for coupling a quencher container to the first conduit.

Embodiment 82. The kit of any one of embodiments 79-81, wherein the first conduit is coupled to a PIC container and a quencher container.

Embodiment 83. The kit of any one of embodiments 79-82, wherein the PIC container and the quencher container are the same container.

Embodiment 84. The kit of any one of embodiments 79-83, wherein the first conduit is configured to be coupled to the first container, providing a fluid communication path between the PIC container and quencher container and the first container.

Embodiment 85. The kit of embodiment 83, wherein the first conduit is configured to be coupled to an inlet of the first container.

Embodiment 86. The kit of any one of embodiments 79-85, further comprising a vascular access device for drawing whole blood from a donor and third conduit extending between the vascular access device and the first inlet of the first container and providing a fluid communication path for transferring the whole blood from the vascular access device into the first container.

Embodiment 87. The kit of embodiment 86, wherein the first container further comprises a second inlet, and wherein the first conduit is configured to be coupled to the second inlet of the first container.

Embodiment 88. The kit of embodiment 86, wherein the first conduit is configured to be coupled to the third conduit, providing a fluid communication path between the PIC container and quencher container and the first container.

Embodiment 89. The kit of any one of embodiments 79-88, wherein the first container contains an anticoagulant.

Embodiment 90. The kit of any one of embodiments 79-89, wherein the kit comprises a third container suitable for storing a pathogen-inactivated whole blood composition, wherein the third container comprises (e.g., includes) at a first inlet and a first outlet, and wherein the kit further comprises a fourth conduit extending between the first outlet of the second container and the first inlet of the third container and providing a fluid communication path for transferring (e.g., under sterile conditions) the whole blood composition from the second container into the third container.

Embodiment 91. The kit of any one of embodiments 79-90, further comprising an infusion line for infusing the pathogen-inactivated whole blood composition into a subject, wherein the infusion line comprises a second vascular access device and an infusion line conduit extending between the first outlet of the second container and the second vascular access device, wherein the infusion line conduit provides a fluid communication path for sterilely transferring the pathogen-inactivated whole blood composition from the second container to the vascular access device.

What is claimed is:

1. A kit for preparing a pathogen-inactivated whole blood composition, comprising:

(a) a vascular access device for drawing whole blood from a donor;

(b) a first container suitable for mixing the whole blood and a pathogen inactivation compound (PIC), wherein the first container comprises at least a first inlet and a first outlet;

(c) a first conduit extending between the vascular access device and the first container and providing a fluid communication path for transferring the whole blood from the donor into the first container;

(d) a container containing a pathogen inactivation compound (PIC container);

(e) a second conduit, wherein the second conduit is coupled or configured to be coupled at one end to the PIC container, wherein the second conduit is coupled to the first container, configured to be coupled to the first container, or configured to be coupled to the first conduit, thereby providing a fluid communication path between the PIC container and the first container; wherein the second conduit further comprises a displacement device suitable for increasing transfer of the PIC into the first container; wherein the displacement device displaces air from the displacement device to facilitate the transfer of the PIC, and wherein the displacement device is separate from the PIC container; and (f) an infusion line assembly for infusing the pathogen-inactivated whole blood composition into a subject, wherein the infusion line assembly comprises a second vascular access device and an infusion line conduit that is coupled or configured to be coupled to a container of the kit.

2. The kit of claim 1, wherein the PIC container is configured to be coupled by a fluid communication path to the first container.

3. The kit of claim 2, wherein the PIC container is configured to be coupled to the first conduit.

4. The kit of claim 1, wherein the PIC container is coupled by a fluid communication path to the first container.

5. The kit of claim 1, further comprising a container containing a quencher (quencher container).

6. The kit of claim 5, wherein the quencher container is configured to be coupled by a fluid communication path to the first container.

7. The kit of claim 6, wherein the quencher container is configured to be coupled to the first conduit.

8. The kit of claim 5, wherein the quencher container is coupled by a fluid communication path to the first container.

9. The kit of claim 5, wherein the second conduit comprises at one end at least one adaptor for coupling the quencher container to the second conduit.

10. The kit of claim 1, wherein the second conduit comprises at one end at least one adaptor for coupling the PIC container to the second conduit.

11. The kit of claim 10, wherein the second conduit comprises at one end a first adaptor for coupling a PIC container to the second conduit and a second adaptor for coupling a quencher container to the second conduit.

12. The kit of claim 1, wherein the first container contains an anticoagulant.

13. The kit of claim 1, further comprising a second container suitable for storing a pathogen-inactivated whole blood composition, wherein the second container comprises at least a first inlet and a first outlet.

14. The kit of claim 13, further comprising a third conduit extending between the first container and the second container and providing a fluid communication path for transferring a mixture comprising a whole blood composition and a PIC from the first container into the second container.

15. The kit of claim 13, wherein the kit comprises a third container suitable for storing a pathogen-inactivated whole blood composition, wherein the third container comprises at least a first inlet and a first outlet, and wherein the kit further comprises a fourth conduit extending between the second container and the third container and providing a fluid communication path for transferring a mixture comprising a whole blood composition and a PIC from the second container into the third container.

16. The kit of claim 13, wherein the infusion line assembly is coupled to the second container.

17. The kit of claim 16, wherein the infusion line conduit extends between the first outlet of the second container and the second vascular access device, and wherein the infusion line conduit provides a fluid communication path for sterilely transferring the pathogen-inactivated whole blood composition from the second container to the vascular access device.

18. The kit of claim 13, wherein the infusion line assembly is configured to be coupled to the second container.

19. The kit of claim 1, wherein the first container further comprises a second inlet and the PIC container is coupled or configured to be coupled by a fluid communication path to the second inlet of the first container.

20. The kit of claim 1, wherein the second conduit is coupled to the first container.

21. The kit of claim 1, wherein the second conduit is configured to be coupled to the first conduit, providing a fluid communication path between the PIC container and the first container.

22. The kit of claim 1, wherein the infusion line assembly is configured to be coupled to a first container, a second container or a third container.

23. The kit of claim 1, wherein the displacement device is a sample diversion pouch.

24. The kit of claim 23, wherein the displacement device is an air pillow or sampling pouch.

25. A kit for preparing a pathogen-inactivated whole blood composition, comprising:

(a) a first container suitable for mixing a whole blood composition, a pathogen inactivation compound (PIC) and a quencher, wherein the first container comprises at least a first inlet and a first outlet;

(b) a second container suitable for storing a pathogen-inactivated whole blood composition, wherein the second container comprises at least a first inlet and a first outlet;

(c) a container containing a pathogen inactivation compound (PIC container);

(d) a container containing a quencher (quencher container);

(e) a first conduit, wherein the first conduit at one end is coupled to or configured to be coupled to the PIC container and the quencher container, wherein the first conduit further comprises a displacement device suitable for increasing the transfer of the PIC and the quencher into the first container, wherein the displacement device displaces air from the displacement device to facilitate the transfer of the PIC and the quencher, and wherein the displacement device is separate from the PIC container and the quencher container;

(f) a second conduit extending between the first container and the second container and providing a fluid communication path for transferring the whole blood composition from the first container to the second container; and (g) an infusion line assembly for infusing the pathogen-inactivated whole blood composition into a subject, wherein the infusion line assembly comprises a vascular access device and an infusion line conduit that is coupled or configured to be coupled to a container of the kit.

26. The kit of claim 25, wherein the first conduit is coupled or configured to be coupled to the first container, providing a fluid communication path between the PIC container and the quencher container and the first container.

27. The kit of claim 26, wherein the first conduit is configured to be coupled to an inlet of the first container.

28. The kit of claim 26, wherein the first conduit is coupled to an inlet of the first container.

29. The kit of claim 25, further comprising a second vascular access device for drawing whole blood from a donor and a third conduit extending between the second vascular access device and the first inlet of the first container and providing a fluid communication path for transferring the whole blood from the donor into the first container.

30. The kit of claim 29, wherein the first conduit is configured to be coupled to the third conduit, providing a fluid communication path between the PIC container and the quencher container and the first container.

31. The kit of claim 25, wherein the first container contains an anticoagulant.

32. The kit of claim 25, wherein the kit comprises a third container suitable for storing a pathogen-inactivated whole blood composition, wherein the third container comprises a first inlet and a first outlet, and wherein the kit further comprises a fourth conduit extending between the second container and the third container and providing a fluid communication path for transferring the whole blood composition from the second container into the third container.

33. The kit of claim 25, wherein the first conduit further comprises at least one adaptor for coupling the first conduit to the PIC container and the quencher container.

34. The kit of claim 33, wherein the first conduit comprises a first adaptor for coupling the PIC container to the first conduit and a second adaptor for coupling the quencher container to the first conduit.

35. The kit of claim 25, wherein the first conduit is coupled to the PIC container and the quencher container.

36. The kit of claim 25, wherein the first container further comprises a second inlet, and wherein the first conduit is coupled or configured to be coupled to the second inlet of the first container.

37. The kit of claim 25, wherein the infusion line assembly is configured to be coupled to a first container, a second container or a third container.

38. The kit of claim 25, wherein the infusion line assembly is coupled to the second container.

39. The kit of claim 25, wherein the infusion line conduit extends between the first outlet of the second container and the vascular access device of the infusion line assembly, wherein the infusion line conduit provides a fluid communication path for sterilely transferring the pathogen-inactivated whole blood composition from the second container to the vascular access device.

40. The kit of claim 25, wherein the displacement device is a sample diversion pouch.

41. The kit of claim 40, wherein the displacement device is an air pillow or sampling pouch.

42. The kit of claim 25, wherein the PIC container and the quencher container are the same container.

43. The kit of claim 25, wherein the infusion line assembly is configured to be coupled to the second container.

* * * * *